(12) United States Patent
Ali et al.

(10) Patent No.: US 8,518,963 B2
(45) Date of Patent: *Aug. 27, 2013

(54) THERAPEUTIC POLYMERIC NANOPARTICLE COMPOSITIONS WITH HIGH GLASS TRANSITION TEMPERATURE OR HIGH MOLECULAR WEIGHT COPOLYMERS

(75) Inventors: Mir Mukkaram Ali, Woburn, MA (US); Abhimanyu Sabnis, Arlington, MA (US); David Dewitt, Allston, MA (US); Greg Troiano, Pembroke, MA (US); James Wright, Lexington, MA (US); Maria Figueiredo, Somerville, MA (US); Michael Figa, Allston, MA (US); Christina Van Geen Hoven, Cambridge, MA (US); Young-Ho Song, Natick, MA (US); Jason Auer, Cambridge, MA (US); Tarikh Christopher Campbell, Boston, MA (US)

(73) Assignee: BIND Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,036

(22) Filed: Feb. 13, 2012

(65) Prior Publication Data

US 2012/0140790 A1    Jun. 7, 2012

Related U.S. Application Data

(63) Continuation of application No. 12/968,625, filed on Dec. 15, 2010.

(60) Provisional application No. 61/286,559, filed on Dec. 15, 2009, provisional application No. 61/286,831, filed on Dec. 16, 2009, provisional application No. 61/286,897, filed on Dec. 16, 2009, provisional application No. 61/306,729, filed on Feb. 22, 2010, provisional application No. 61/405,778, filed on Oct. 22, 2010.

(51) Int. Cl.
*A61K 9/50* (2006.01)
*A61K 31/44* (2006.01)

(52) U.S. Cl.
USPC .................................. 514/283; 424/501

(58) Field of Classification Search
None
See application file for complete search history.

(56) References Cited

U.S. PATENT DOCUMENTS

| | | |
|---|---|---|
| 5,302,401 A | 4/1994 | Liversidge et al. |
| 5,543,158 A | 8/1996 | Gref et al. |
| 5,578,325 A | 11/1996 | Domb et al. |
| 5,766,635 A | 6/1998 | Spenleuhauer et al. |
| 6,007,845 A | 12/1999 | Domb et al. |
| 6,136,846 A | 10/2000 | Rubinfeld et al. |
| 6,139,870 A | 10/2000 | Verrecchia |
| 6,201,072 B1 | 3/2001 | Rathi et al. |
| 6,254,890 B1 | 7/2001 | Hirosue et al. |
| 6,265,609 B1 | 7/2001 | Jackson et al. |
| 6,346,274 B1 | 2/2002 | Koll et al. |
| 6,395,718 B1 | 5/2002 | Slusher et al. |
| 6,528,499 B1 | 3/2003 | Kozikowski et al. |
| 6,841,547 B2 | 1/2005 | Brown et al. |
| 6,875,886 B2 | 4/2005 | Frangioni |
| 6,890,950 B2 | 5/2005 | Boothman et al. |
| 6,902,743 B1 | 6/2005 | Setterstrom et al. |
| 6,916,788 B2 | 7/2005 | Seo et al. |
| 7,422,902 B1 | 9/2008 | Wheeler et al. |
| 8,003,128 B2 | 8/2011 | Kreuter et al. |
| 8,034,765 B2 | 10/2011 | De et al. |
| 8,206,747 B2 | 6/2012 | Zale et al. |
| 8,211,473 B2 | 7/2012 | Troiano et al. |
| 8,318,208 B1 | 11/2012 | Zale et al. |
| 8,318,211 B2 | 11/2012 | Zale et al. |
| 8,357,401 B2 | 1/2013 | Troiano et al. |
| 2002/0045582 A1 | 4/2002 | Margolin et al. |
| 2002/0119916 A1 | 8/2002 | Hassan |
| 2003/0068377 A1 | 4/2003 | Fowers et al. |
| 2003/0143184 A1 | 7/2003 | Seo et al. |
| 2003/0232887 A1 | 12/2003 | Johnson et al. |
| 2003/0235619 A1 | 12/2003 | Allen et al. |
| 2004/0054190 A1 | 3/2004 | Pomper et al. |
| 2004/0071768 A1 | 4/2004 | Sarris et al. |
| 2004/0086544 A1 | 5/2004 | Bezemer et al. |
| 2004/0185170 A1 | 9/2004 | Chungi et al. |
| 2004/0219224 A1 | 11/2004 | Yakovlevsky et al. |
| 2004/0220081 A1 | 11/2004 | Kreitz et al. |
| 2004/0247624 A1 | 12/2004 | Unger et al. |

(Continued)

FOREIGN PATENT DOCUMENTS

| | | |
|---|---|---|
| CN | 101053553 A | 10/2007 |
| EP | 0805678 A1 | 11/1997 |

(Continued)

OTHER PUBLICATIONS

Gill et. al., Modulated Differential Scanning Calorimetry, Journal of Thermal Analysis, vol. 40 p. 931-939, 1993.*

(Continued)

*Primary Examiner* — Christina Bradley
*Assistant Examiner* — Jeanette Lieb
(74) *Attorney, Agent, or Firm* — Goodwin Procter LLP

(57) ABSTRACT

The present disclosure relates in part to pharmaceutical compositions comprising polymeric nanoparticles having certain glass transition temperatures. Other aspects of the invention include methods of making such nanoparticles.

12 Claims, 19 Drawing Sheets

(56) References Cited

U.S. PATENT DOCUMENTS

| | | |
|---|---|---|
| 2004/0247680 A1 | 12/2004 | Farokhzad et al. |
| 2005/0037075 A1 | 2/2005 | Farokhzad et al. |
| 2005/0037086 A1 | 2/2005 | Tyo et al. |
| 2005/0123617 A1 | 6/2005 | Chang et al. |
| 2005/0136258 A1 | 6/2005 | Nie et al. |
| 2005/0142205 A1 | 6/2005 | Rashba-Step et al. |
| 2005/0256071 A1 | 11/2005 | Davis |
| 2005/0266067 A1 | 12/2005 | Sengupta et al. |
| 2006/0002852 A1 | 1/2006 | Saltzman et al. |
| 2006/0002971 A1 | 1/2006 | Saltzman et al. |
| 2006/0057219 A1 | 3/2006 | Nagasaki et al. |
| 2006/0110460 A1 | 5/2006 | Ferret et al. |
| 2006/0165987 A1 | 7/2006 | Hildgen et al. |
| 2007/0031402 A1 | 2/2007 | Zhang et al. |
| 2007/0041901 A1 | 2/2007 | Diener et al. |
| 2007/0043066 A1 | 2/2007 | Sum et al. |
| 2007/0053845 A1 | 3/2007 | Sengupta et al. |
| 2007/0154554 A1 | 7/2007 | Burgermeister et al. |
| 2008/0057102 A1 | 3/2008 | Roorda |
| 2008/0081074 A1 | 4/2008 | Gu et al. |
| 2008/0124400 A1 | 5/2008 | Liggins et al. |
| 2008/0193381 A1 | 8/2008 | Babich et al. |
| 2008/0267876 A1* | 10/2008 | Benita et al. .............. 424/9.1 |
| 2009/0053293 A1 | 2/2009 | Liang et al. |
| 2009/0053315 A1 | 2/2009 | Brough et al. |
| 2009/0061009 A1 | 3/2009 | Schwarz et al. |
| 2009/0061010 A1 | 3/2009 | Zale et al. |
| 2009/0074753 A1 | 3/2009 | Lynch |
| 2009/0074828 A1 | 3/2009 | Alexis et al. |
| 2009/0155349 A1 | 6/2009 | Heller et al. |
| 2009/0170753 A1 | 7/2009 | Welz et al. |
| 2009/0306120 A1 | 12/2009 | Lim et al. |
| 2009/0317479 A1 | 12/2009 | Ishihara et al. |
| 2010/0008998 A1 | 1/2010 | Kang et al. |
| 2010/0015050 A1 | 1/2010 | Panyam et al. |
| 2010/0040537 A1 | 2/2010 | Gu et al. |
| 2010/0068285 A1 | 3/2010 | Zale et al. |
| 2010/0068286 A1 | 3/2010 | Troiano et al. |
| 2010/0069426 A1 | 3/2010 | Zale et al. |
| 2010/0087337 A1 | 4/2010 | Dewitt |
| 2010/0104645 A1 | 4/2010 | Ali et al. |
| 2010/0104655 A1 | 4/2010 | Zale et al. |
| 2010/0166866 A1 | 7/2010 | Fischer et al. |
| 2010/0216804 A1 | 8/2010 | Zale et al. |
| 2010/0226986 A1 | 9/2010 | Grayson et al. |
| 2010/0266491 A1 | 10/2010 | Farokhzad et al. |
| 2010/0303723 A1 | 12/2010 | Farokhzad et al. |
| 2010/0303900 A1 | 12/2010 | Ramstack et al. |
| 2010/0316725 A1 | 12/2010 | Ryde et al. |
| 2011/0159079 A1 | 6/2011 | Li et al. |
| 2011/0217377 A1 | 9/2011 | Zale et al. |
| 2011/0224288 A1 | 9/2011 | Zale et al. |
| 2011/0274759 A1 | 11/2011 | Troiano et al. |
| 2011/0275704 A1 | 11/2011 | Troiano et al. |
| 2011/0294717 A1 | 12/2011 | Ali et al. |
| 2012/0004293 A1 | 1/2012 | Zale et al. |
| 2012/0027820 A1 | 2/2012 | Troiano et al. |
| 2012/0140790 A1 | 6/2012 | Ali et al. |
| 2012/0276162 A1 | 11/2012 | Zale et al. |

FOREIGN PATENT DOCUMENTS

| | | |
|---|---|---|
| EP | 1985309 A1 | 10/2008 |
| EP | 2106806 A1 | 10/2009 |
| KR | 10-0418916 | 3/2002 |
| KR | 20020041712 A | 6/2002 |
| WO | WO-0000222 A1 | 1/2000 |
| WO | WO-03055469 A1 | 7/2003 |
| WO | WO-03/086369 A2 | 10/2003 |
| WO | WO-2004084871 A1 | 10/2004 |
| WO | WO-2005/046572 A2 | 5/2005 |
| WO | WO-2006/093991 A1 | 9/2006 |
| WO | WO-2007/024323 A2 | 3/2007 |
| WO | WO-2007/028341 A1 | 3/2007 |
| WO | WO-2007/034479 A2 | 3/2007 |
| WO | WO-2007/074604 A1 | 7/2007 |
| WO | WO-2007110152 A2 | 10/2007 |
| WO | WO-2007/133807 A2 | 11/2007 |
| WO | WO-2008/019142 A2 | 2/2008 |
| WO | WO-2008/058192 A2 | 5/2008 |
| WO | WO-2008/105773 A2 | 9/2008 |
| WO | WO-2008/121949 A1 | 10/2008 |
| WO | WO-2008/124632 A1 | 10/2008 |
| WO | WO-2008/124634 A1 | 10/2008 |
| WO | WO-2008/124639 A2 | 10/2008 |
| WO | WO-2008/139804 A1 | 11/2008 |
| WO | WO-2009/070302 A1 | 6/2009 |
| WO | WO-2010/005721 A2 | 1/2010 |
| WO | WO-2010/005723 A2 | 1/2010 |
| WO | WO-2010/005725 A2 | 1/2010 |
| WO | WO-2010/005726 A2 | 1/2010 |
| WO | WO-2010/068866 A2 | 6/2010 |
| WO | WO-2010/075072 A2 | 7/2010 |
| WO | WO-2010/114768 A1 | 10/2010 |
| WO | WO-2010/114770 A1 | 10/2010 |
| WO | WO-2011/072218 A2 | 6/2011 |
| WO | WO-2011/084513 A2 | 7/2011 |
| WO | WO-2011/084518 A2 | 7/2011 |
| WO | WO-2011/084521 A2 | 7/2011 |
| WO | WO-2011/119995 A2 | 9/2011 |
| WO | WO-2012054923 A2 | 4/2012 |
| WO | WO-2012166923 A2 | 12/2012 |

OTHER PUBLICATIONS

Jean-Christoph Olivier, Drug Transport to Brain with Targeted Nanoparticles, The American Society for Experimental Neurotherapuetics, Inc. vol. 2, p. 108-119, Jan. 2005.*

Omelczuk and McGinity (The Influence of Polymer Glass Transition Temperature and Molecular Weight on Drug Release from Tablets Containing Poly(DL-lactic AcidPharmacuetical Research, vol. 9, No. 1, p. 26-32 1992.*

Olivier Drug Transport to Brain with Targeted Nanoparticles, The American Society for Experimental Neurotherapuetics, Inc. vol. 2, p. 108-119 (Jan. 2005).*

Omelczuk and McGinty, The Influence of Polymer Glass Transition Temperature and Molecular Weight on Drug Release from Tablets Containing Poly(DL-lactic Acid, Pharmaceutical Research vol. 9, No. 1, p. 26-32, (1992).*

Gill et. al (Modulated Differential Scanning Calorimetry, Journal of Thermal Analysis, vol. 40 p. 931-939, 1993.*

Olivier, Drug Transport to Brain with Targeted Nanoparticles, The American Society for Experimental Neurotherapuetics, Inc. vol. 2, p. 108-119, (Jan. 2005).*

Omelczuk and McGinity, The Influence of Polymer Glass Transition Temperature and Molecular Weight on Drug Release from Tablets Containing Poly(DL-lactic Acid, Pharmaceutical Research vol. 9, No. 1, p. 26-32, 1992.*

Abdelwahed et al., "Freeze-Drying of Nanoparticles: Formulation, Process and Storage Considerations," *Adv. Drug Deliv. Rev.* (2006) 58:1688-1713.

Abizaid et al., "Sirolimus-eluting Stents Inhibits Neointimal Hyperplasia in Diabetic Patients," *Eur. Heart J.* (2006) 25:104-112.

Adams et al, "Amphiphilic Block Copolymers for Drug Delivery", *J. Pharm. Sci.* (2003) 92, 1343-1355.

Barinka et al., "Interactions Between Human Glutamate Carboxypeptidase II and Urea-Based Inhibitors: Structural Characterization," *J. Med. Chem.* (2008) 51:7737-7743.

Barinka et al., Structural Insight into the Pharmacophore Pocket of Human Glutamate Carboxypeptidase II, *J. Med. Chem.* (2007) 50:3267-3273.

Blindt et al., "A Novel Drug-Eluting Stent Coated with an Integrin-Binding Cyclic Arg-Gly-Asp Peptide Inhibits Neointimal Hyperplasia by Recruiting Endothelial Progenitor Cells," *J. Amer. Coll. Cardiol.* (2006) 47(9):1786-1795.

Caliceti et al., "Effective Protein Release Form PEG/PLA Nano-Particles Produced by Compressed Gas Anti-Solvent Precipitation Techniques," *Journal of Controlled Release*, (2004) 94:195-205.

Chandran, et al., "Characterization of a Targeted Nanoparticle Functionalized with a Urea-Based Inhibitor of Prostate-Specific Membrane Antigen (PSMA)," *Cancer Biol. Ther.* (2008) 7:4:1-9.

Chen et al., "Radiohalogenated Prostate-Specific Membrane Antigen (PSMA)-Based Ureas as Imaging Agents for Prostate Cancer," *J. Med. Chem.* (2008) 51(24):7933-7943.

Cheng et al. "Formulation of Functionalized PLGA-PEG Nanoparticles for in Vivo Targeted Drug Delivery" *Biomaterials* (2007) 28:869-879.

Dancey et al., "Therapeutic Targets mTOR and Related Pathways," *Cancer Biol. Ther.* (2006) 5:9: 1065-1073.

Davaran et al., "Preparation and in Vitro Evaluation of Linear and Star-branched PLGA Nanoparticles for Insulin Delivery," *J. Bioact. Compat. Polym.* (2008) 115-131.

De Jaeghere et al., "Freeze-Drying and Lypopreservation of Diblock and Triblock Poly(Lactic Acid)-Poly(Ethylene Oxide) (PLA-PEO) Copolymer Nanoparticles," *Phar. Dev. Tech.* (2000) 5: 473-483.

De Jaeghere et al., "Formulation and Lyoprotection of Poly (Lactic Acid-*Co*-Ethylene Oxide) Nanoparticles: Influence on Physical Stability and in Vitro Cell Uptake," *Pharm. Res.* (1999).

Eurasian Search Report for Application No. EA201170038, dated Jul. 8, 2011.

Extended European Search Report for Application No. EP 09794913.5 mailed Jul. 8, 2011.

Extended European Search Report for Application No. EP 09794915.0, mailed Jan. 25, 2012.

Ewesuedo et al., "Chapter 1: Systemically Administered Drugs." *Drug delivery systems in Cancer Therapy*, Ed. D.M. Brown. Totowa:Humana, (2003) 3-14.

Farokhzad et al., "Nanoparticle-Aptamer Bioconjugates: A New Approach for Targeting Prostate Cancer Cells," *Cancer Res.* (Nov. 1, 2004) 64:7668-7672.

Farokhzad et al., "Targeted Nanoparticle-Aptamer Bioconjugates for Cancer Chemotherapy in Vivo," *Proc. Natl. Acad. Sci. USA* (2006) 103,16:6315-6320.

Foss et al., "Radiolabeled Small-Molecule Ligands for Prostate-Specific Membrane Antigen: in Vivo Imaging in Experimental Models of Prostate Cancer," *Clin. Cancer Res.* (2005)11(11):4022-4028.

Foss, Poster Session: Novel Probes and Activation Strategies, Part 3, "Synthesis and Validation of a Novel Small-Molecule Fluorescent Probe for PSMA Expression in Human Tumor Neovasculature," *4th Annual Meeting for the Society for Molecular Imaging*, (Sep. 7-10, 2005.).

Gao et al., "In Vivo Cancer Targeting and Imaging with Semiconductor Quantum Dots," *Nat. Biotechnol.*, (2004) 22, 8: 969-976.

Govender et al., "Defining the Drug Incorporation Properties of PLA-PEG Nanoparticles," *Int. J. Pharm.* (2000) 199:95-110.

Gref et al., "Development and Characterization of CyA-loaded Poly(lactic acid)-poly(ethylene glycol)PEG Micro- and Nanoparticles. Comparison with Conventional PLA Particulate Carriers." *Eur. J. Pharm. Biopharm.* (2001) 51:111-118.

Gref, Ruxandra, et al., "Biodegradable Long-Circulating Polymeric Nanospheres," *Science* (1994) 263:1600-1603.

Gu et al. "Precise Engineering of Targeted Nanoparticles by Using Self-Assembled Biointegrated Block Copolymers," *Proc. Natl. Acad. Sci. USA* (2008) 105:2586-2591.

Heald et al., "Poly(lactic acid)-Poly(ethylene oxide) (PLA-PEG) Nanoparticles: NMR Studies of the Central Solidlike PLA Core and the Liquid PEG Corona," *Langmuir* (2002) 18:3669-3675.

Hederstrom et al., "Purification and Surface Modification of Polymeric Nanoparticles for Medical Applications" Master's Thesis. SINTEF Materials and Chemistry, Trondheim, Norway, Mar. 3, 2008.

Heldmann et al., "Paclitaxel Stent Coating Inhibits Neointimal Hyperplasia at 4 weeks in a Porcine Model of Coronary Restenosis," *Circulation* (2001) 103:2289-2295.

Humblet et al., "An HPLC/Mass Spectrometry Platform for the Development of Multimodality Contrast Agents and Targeted Therapeutics: Prostate-Specific Membrane Antigen Small Molecule Derivatives," *Contrast Med. Mol. Imaging* (2006) 1:196-211.

Humblet et al., "High-Affinity Near-Infrared Fluorescent Small-Molecule Contrast Agents for in Vivo Imaging of Prostate-Specific Membrane Antigen," *Mol. Imaging* ( 2005) 4:448-462.

International Search Report for Application No. PCT/US08/13158 dated Jan. 20, 2009 and mailed Feb. 17, 2009.

International Search Report for Application No. PCT/US08/58873 dated Aug. 15, 2008 and mailed Aug. 28, 2008.

International Search Report for Application No. PCT/US09/47513 dated Jan. 18, 2010 and mailed Jan. 18, 2010.

International Search Report for Application No. PCT/US09/47517 dated Feb. 25, 2010 and mailed Mar. 2, 2010.

International Search Report for Application No. PCT/US09/47518 dated Mar. 5, 2010 and mailed Mar. 5, 2010.

International Search Report for Application No. PCT/US09/67672 dated Aug. 20, 2010 and mailed Aug. 23, 2010.

International Search Report for Application No. PCT/US09/68028 dated Aug. 9, 2010 and mailed Aug. 23, 2010.

International Search Report for Application No. PCT/US10/59879 dated Aug. 30, 2011 and mailed Aug. 30, 2011.

International Search Report for Application No. PCT/US10/60564 dated Sep. 29, 2011 and mailed Sep. 29, 2011.

International Search Report for Application No. PCT/US10/60570 dated Aug. 25, 2011 and mailed Aug. 25, 2011.

International Search Report for Application No. PCT/US10/60575 dated Aug. 25, 2011 and mailed Aug. 25, 2011.

Japaprakash et al., "Design and Synthesis of a PSMA Inhibitor-Doxorubicin Conjugate for Targeted Prostate Cancer Therapy," *ChemMedChem* (2006) 1:299-302.

Jiang et al., "Preparation of PLA and PLGA Nanoparticles by Binary Organic Solvent Diffusion Method," *J. Cent. South Univ. Technol.*, (2003) 10, 3:202-206.

Koziara et al. "Blood Compatibility of Cetyl Alcohol/Polysorbate-Based Nanoparticles." *Pharm. Res.* (2005) 22,11:1821-1828.

Kozikowski et al., Design of Remarkably Simple, Yet Potent Urea-Based Inhibitors of Glutamate Carboxypeptidase II (NAALADase), *J. Med. Chem.* (2001) 44:298-301.

Kozikowski et al., "Synthesis of Urea-Based Inhibitors as Active Site Probes of Glutamate Carboxypeptidase II: Efficacy as Analgesic Agents," *J. Med. Chem.* (2004) 47:1729-1738.

Kwon et al., "Long Acting Porous Microparticle for Pulmonary Protein Delivery," *Inter. J. Pharm.* (2007) 333:5-9.

Maresca et al., "A Series of Halogenated Heterodimeric Inhibitors of Prostate Specific Membrane Antigen (PSMA) as Radiolabeled Probes for Targeting Prostate Cancer," *J. Med. Chem.* (2009) 52(2):347-57.

Mease et al., "N-[N-[(S)-1,3-Dicarboxypropyl] Carbamoyl]-4-[$^{18}$F] Fluorobenzyl-L-Cysteine, [$^{18}$F] DCFBC: A New Imaging Probe for Prostate Cancer," *Clin. Cancer Res.* (2008) 14, 10:3036-3043.

Misra et al., "Production of Multimeric Prostate-Specific Membrance Antigen Small-Molecule Radiotracers Using a Solid-Phase $^{99m}$Tc Preloading Strategy," *J. Nuclear Med.*, (2007) 48, 8: 1379-1389.

Murugesan et al., Pegylated Poly(lactide-co-glycolide) (PLGA) Nanoparticulate Delivery of Docetaxel: Synthesis of Diblock Copolymers, Optimization of Preparation Variables on Formulation Characteristics and in Vitro Release Studies. *J. Biomed. Nanotechnol.* (2007) 3:52-60.

Musumeci et al., "Lyoprotected Nanosphere Formulations for Paclitaxel Controlled Delivery," *J. Nanosci. Nanotechnol.* (2006) 6:1-8.

Ojer et al., "Spray-Drying of Poly(anhydride) Nanoparticles for Drug/Antigen Delivery," *J. Drug. Del. Sci Tech.* (2010) 20:353-359.

Oliver et al., "Conformational and SAR Analysis of NAALADase and PSMA Inhibitors," *Biorg. Med. Chem.* (2003) 11:4455-4461.

Omelczuk et al., The Influence of Polymer Glass Transition Temperature and Molecular Weight on Drug Release from Tablets Containing Poly(DL-lactic acid). *Pharm. Res.* (1992) 9(1):26-32.

Pomper, Martin G., Russell H. Morgan Department of Radiology and Radiological Science, Johns Hopkins University, "New Developments in Molecular Imaging of Prostate Cancer," Topical Symposium on: Advanced Molecular Imaging Techniques in the Detection, Diagnosis, Therapy, and Follow-up of Prostate Cancer, Palazzo Barberini, Rome, Dec. 6, 2005.

Pourcelle et al., "PCL-PEG-Based Nanoparticles Grafted with GRGDS Peptide: Preparation and Surface Analysis by XPS," *Biomacromolecules* 8 (2007) 3977-3983.

Pulkkinen et al., "Three-Step Tumor Targeting of Paclitaxel Using Biotinylated PLA-PEG Nanoparticles and Avidin-Biotin Technology: Formulation Development and in Vitro Anticancer Activity," *Eur. J. Pharm. Biopharm.* (2008) 70:66-74.

Riley et al. "Colloidal Stability and Drug Incorporation Aspects of Micellar-like PLA-PEG Nanoparticles," *Colloids Surf. B: Biointer.* (1999) 16:147-59.

Sapra et al., "Ligand-Targeted Liposomal Anticancer Drugs," *Prog. Lipid Res.* (2003) 42:439-462.

Sweetman, "Martindale: The Complete Drug Reference," 33rd ed., 2002, Pharmaceutical Press, entry for Docetaxel, p. 534.

Tamilvanan et al., "Manufacturing Techniques and Excipients Used During the Design of Biodegradable Polymer-based Microspheres Containing Therapeutic Peptide/Protein for Parenteral Controlled Drug Delivery" *PDA J. Pharm. Sci. Tech.* 62 (2008) 125-154.

Tang, Hailun, et al., "Prostate Targeting Ligands Based on N-Acetylated α-Linked Acidic Dipeptidase," Biochem. Biophys. Res. Comm. 307 (2003), pp. 8-14.

Tobio, M. et al., "Stealth PLA-PEG Nanoparticles as Protein Carriers for Nasal Administration," *Pharm. Res.* (1998) 15, 2:270-275.

Vicari et al., "Paclitaxel Loading in PLGA Nanospheres Affected the in Vitro Drug Cell Accumulation and Antiproliferative Activity," *BMC Cancer* (2008) 8:212.

Yamamoto et al., "Long-Crculating Poly(ehtylene glycol)-Poly(D,L-lactide) Block Copolymer Micelles with Modulated Surface Charge," *J. Control. Release* (2001) 77:27-38.

Zhang et al., "Neointimal Hyperplasia Persists at Six Months after Siroli Mus-Eluting Stent Implantation in Diabetic Porcine," *Cardiovasc. Diabetol.* (2007) 6, 16:1-7.

Zhou et al., "NAAG Peptidase Inhibitors and Their Potential for Diagnosis and Therapy," *Nature Rev. Drug Discov.* (2005) 4:1015-1026.

Bilati, et al. "Nanoprecipitation Versus Emulsion-based Techniques for the Encapsulation of Proteins Into Biodegradable Nanoparticles and Process-related Stability Issues," *AAPS PharmSciTech.* (2005) 6(4):E594-E604.

Eurasian Search Report for Application No. EA 201170039, dated Nov. 21, 2011.

Extended European Search Report for Application No. 09835578.7, dated May 18, 2012.

Feng et al., "Nanoparticles of Biodegradable Polymers for Clinical Administration of Paclitaxel," *Curr. Med. Chem.* (2004) 11:413-424.

Hrkach et al., "Preclinical Development and Clinical Translation of a PSMA-Targeted Docetaxel Nanoparticle with a Differentiated Pharmacological Profile," *Sci. Transl. Med.* (2012) 4:1-11.

International Search Report for Application No. PCT/US11/057498 dated May 9, 2012 and mailed May 10, 2012.

Lyseng-Williamson et al. "Docetaxel a Review of its Use in Metastatic Breast Cancer," *Drugs* (2005) 65(17):2513-16.

Olivier, "Drug Transport to Brain with Targeted Nanoparticles," *Neurotherapeutics* (2005) 2:108-119.

Fournier et al., "Experimental Studies and Preliminary Clinical Trial of Vinorelbine-loaded Polymeric Bioresorbable Implants for the Local Treatment of Solid Tumors," Cancer Research. (1991) 51: 5384-5391.

International Search Report for PCT/US09/47515 dated Jan. 18, 2010 and mailed Jan. 19, 2010.

Musumeci et al., "PLA/PLGA nanoparticles for sustained release of docetaxel," International Journal of Pharmaceutics (2006) 325:172-179.

Senthilkumar et al., "Long Circulating PEGylated Poly(D,L-lactide-co-glycolide) Nanoparticulate Delivery of Docetaxel to Solid Tumors," *J. Drug Target.* (2008) 424-435.

Galsky et al., "Cabazitaxel," *Nature Reviews.* (2010) 9:677-678.

International Search Report for Application No. PCT/US2012/040215 dated Nov. 16, 2012 and mailed Nov. 16, 2012.

Peracchia, et al., "PEG-coated nanospheres from amphiphilic diblock and multiblock copolymers: Investigation of their drug encapsulation and release characteristics," *Journal of Controlled Release.* (1996) 46:223-231.

* cited by examiner

THERAPEUTIC POLYMERIC NANOPARTICLE COMPOSITIONS WITH HIGH GLASS TRANSITION TEMPERATURE OR HIGH MOLECULAR WEIGHT COPOLYMERS

RELATED APPLICATIONS

This application is a continuation of U.S. Ser. No. 12/968,625 filed Dec. 15, 2010, which in turn claims the benefit of and priority to U.S. Ser. No. 61/286,559 filed Dec. 15, 2009, U.S. Ser. No. 61/306,729 filed Feb. 22, 2010, U.S. Ser. No. 61/405,778 filed Oct. 22, 2010, U.S. Ser. No. 61/286,831 filed Dec. 16, 2009, and U.S. Ser. No. 61/286,897 filed Dec. 16, 2009, each of which is hereby incorporated by reference in its entirety.

BACKGROUND

Systems that deliver certain drugs to a patient (e.g., targeted to a particular tissue or cell type or targeted to a specific diseased tissue but not normal tissue), or that control release of drugs has long been recognized as beneficial. For example, therapeutics that include an active drug and that are capable of locating in a particular tissue or cell type e.g., a specific diseased tissue, may reduce the amount of the drug in tissues of the body that do not require treatment. This is particularly important when treating a condition such as cancer where it is desirable that a cytotoxic dose of the drug is delivered to cancer cells without killing the surrounding non-cancerous tissue. Further, such therapeutics may reduce the undesirable and sometimes life threatening side effects common in anticancer therapy. For example, nanoparticle therapeutics may, due the small size, evade recognition within the body allowing for targeted and controlled delivery while e.g., remaining stable for an effective amount of time.

Therapeutics that offer such therapy and/or controlled release and/or targeted therapy also must be able to deliver an effective amount of drug. It can be a challenge to prepare nanoparticle systems that have an appropriate amount of drug associated with each nanoparticle, while keeping the size of the nanoparticles small enough to have advantageous delivery properties. For example, while it is desirable to load a nanoparticle with a high quantity of therapeutic agent, nanoparticle preparations that use a drug load that is too high will result in nanoparticles that are too large for practical therapeutic use. Further, it may be desirable for therapeutic nanoparticles to remain stable so as to e.g. substantially limit rapid or immediate release of the therapeutic agent.

Accordingly, a need exists for new nanoparticle formulations and methods of making such nanoparticles and compositions, that can deliver therapeutic levels of drugs to treat diseases such as cancer, while also reducing patient side effects.

SUMMARY

In one aspect, the disclosure provides a pharmaceutical aqueous suspension comprising a plurality of nanoparticles, having a glass transition temperature between about 37° C. and about 50° C., wherein each of the nanoparticles comprises a therapeutic agent and a block copolymer having at least one hydrophobic portion and at least one hydrophilic portion. The therapeutic agent may be a taxane agent, such as docetaxel. The hydrophobic portion may be selected, for example, from poly(D,L-lactic) acid and poly(lactic acid-co-glycolic acid). The hydrophilic portion may be, for example, poly(ethylene)glycol. The nanoparticles may further comprise poly(D,L-lactic) acid or poly(lactic) acid-co-poly(glycolic) acid.

In an embodiment, provided herein is a pharmaceutical aqueous suspension comprising a plurality of fast release biocompatible, therapeutic nanoparticles having a glass transition temperature between about 37° C. and about 38° C., wherein each of the nanoparticles comprises a therapeutic agent and a block copolymer having at least one hydrophobic portion and at least one hydrophilic portion. Such nanoparticles may release about 70% to about 100% of the therapeutic agent at four hours in an in vitro dissolution test.

In another embodiment, provided herein is a pharmaceutical aqueous suspension comprising a plurality of moderate release biocompatible, therapeutic nanoparticles having a glass transition temperature between about 39° C. and about 41° C., wherein each of the nanoparticles comprises a therapeutic agent and a block copolymer having at least one hydrophobic portion and at least one hydrophilic portion. Such therapeutic nanoparticles may release between about 50% to about 70% of the therapeutic agent at four hours in an in vitro dissolution test.

In another embodiment, a pharmaceutical aqueous suspension is provided that comprises a plurality of slow release biocompatible, therapeutic nanoparticles having a glass transition temperature between about 42° C. and about 50° C., wherein each of the nanoparticles comprises a therapeutic agent and a block copolymer having at least one hydrophobic portion and at least one hydrophilic portion. Such a therapeutic nanoparticle may release about 50% or less of the therapeutic agent at four hours in an in vitro dissolution test.

In one embodiment, disclosed nanoparticles may comprise about 0.1 to about 35, or 0.2 to about 20 weight percent of a therapeutic agent; about 10 to about 99 weight percent poly(D,L-lactic) acid-block-poly(ethylene)glycol copolymer or poly(lactic)-co-poly(glycolic) acid-block-poly(ethylene)glycol copolymer; and about 0 to about 75 weight percent, or about 0 to about 50 weight percent, poly(D,L-lactic) acid or poly(lactic) acid-co-poly(glycolic) acid. In another embodiment, the poly(D,L-lactic) acid portion of the copolymer has a number average molecular weight of about 16 kDa, and the poly(ethylene)glycol portion of the copolymer has a number average molecular weight of about 5 kDa. In an embodiment, the poly(D,L-lactic) acid has a number average molecular weight of about 8.5 kDa. In another embodiment, the poly(D,L-lactic) acid has a number molecular weight of about 75 kDa.

In one embodiment, the nanoparticle glass transition temperature, e.g. in a disclosed aqueous solution, may be about 37° C. to about 39° C., or about 37° C. to about 38° C. In another embodiment, an aqueous suspension of nanoparticles may have a glass transition temperature that may be about 39° C. to about 41° C., or may be about 42° C. to about 50° C. (e.g. about 41-45° C., e.g. for slow release particles). The glass transition temperature may be measured by Heat Flux Differential Scanning calorimetry or Power Compensation Differential Scanning calorimetry.

In one embodiment, the disclosed nanoparticles release less than about 50% of the therapeutic agent as determined in an in vitro dissolution test at a 4 hour time point (or optionally at a 1, 2, 8 or 24 hour time point). In another embodiment, the nanoparticles release between about 50 to about 70% of the therapeutic agent as determined in an in vitro dissolution test at a 4 hour time point (or optionally at a 1, 2, 8 or 24 hour time point). In another embodiment, the nanoparticles release between about 70 to about 100% of the therapeutic agent as determined in an in vitro dissolution test at a 4 hour time point (or optionally at a 1, 2, 8 or 24 hour time point).

In another aspect, the disclosure provides a method for determining the drug release rate of a therapeutic polymeric nanoparticle composition, comprising: a) providing at least one first plurality of polymeric nanoparticles comprising a first therapeutic agent, a first block copolymer having at least one hydrophobic portion and at least one hydrophilic portion, and optionally poly(D,L-lactic) acid or poly(lactic) acid-co-poly(glycolic) acid; b) determining the nanoparticle glass transition temperature for the at least one first plurality of polymeric nanoparticles; c) determining the drug release rate from the at least one first plurality of polymeric nanoparticles; and d) determining the correlation between the nanoparticle glass transition temperature and the drug release rate for the at least one first plurality of polymeric nanoparticles.

A method for screening nanoparticle suspensions is also provided, comprising: i) providing a suspension comprising a first plurality of polymeric nanoparticles, wherein the nanoparticles each comprise a therapeutic agent, a block copolymer having at least one hydrophobic portion and at least one hydrophilic portion, and a homopolymer selected from poly (D,L-lactic) acid or poly(lactic) acid-co-poly(glycolic) acid; ii) determining the glass transition temperature for the suspension; iii) increasing or decreasing the amount of the homopolymer in the first plurality of polymeric nanoparticles; and iv) repeating steps i)-iii) until a suspension with a desired glass transition temperature is achieved.

A method for screening nanoparticle suspensions to identify a suspension having a specific release rate is provided, comprising: a) separately preparing a plurality of suspensions having nanoparticles comprising a therapeutic agent, a block copolymer having at least one hydrophobic portion and at least one hydrophilic portion, and optionally a homopolymer selected from poly(D,L-lactic) acid or poly(lactic) acid-co-poly(glycolic) acid; wherein each suspension is in a separate compartment, each suspension comprises a pre-determined molecular weight of the block copolymer and if present, a pre-determined molecular weight of the homopolymer; b) determining the glass transition temperature of each of the suspensions; c) identifying the suspension having a pre-determined glass transition temperature.

BRIEF DESCRIPTION OF THE DRAWINGS

FIG. 2A shows particle formation and hardening (upstream processing). FIG. 2B shows particle work up and purification (downstream processing).

DETAILED DESCRIPTION

Figure 1:
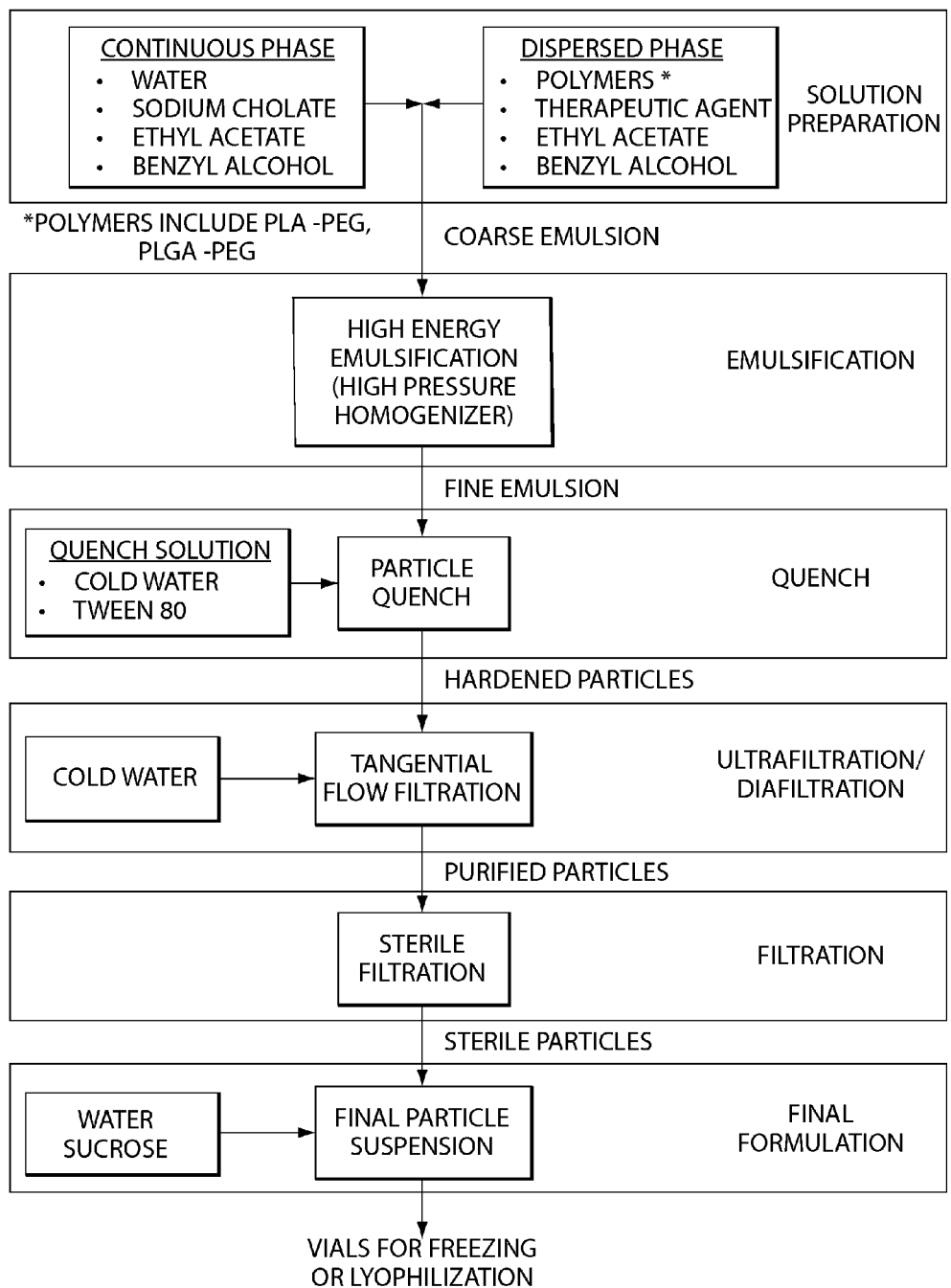
FIG. 1 is a flow chart for an emulsion process for forming disclosed nanoparticles.

At least in part, this disclosure relates to fast releasing biocompatible, therapeutic nanoparticles having a glass transition temperature between about 37° C. and about 38° C., and/or pharmaceutical aqueous suspensions that include a plurality of moderate releasing biocompatible, therapeutic nanoparticles having a glass transition temperature between about 39° C. and about 41° C., and/or slow releasing pharmaceutical aqueous suspensions that include a plurality of biocompatible, therapeutic nanoparticles having a glass transition temperature between about 42° C. and about 50° C. (or about 42 to about 45° C.). Disclosed nanoparticles include a therapeutic agent and may include a block copolymer having at least one hydrophobic portion and at least one hydrophilic portion.

For example, provided herein is a pharmaceutical aqueous suspension comprising a plurality of fast release biocompatible, therapeutic nanoparticles having a glass transition temperature between about 37° C. and about 38° C., wherein each of the nanoparticles comprises a therapeutic agent and a block copolymer having at least one hydrophobic portion and at least one hydrophilic portion wherein the nanoparticles release about 70% to about 100% of the therapeutic agent at four hours in an in vitro dissolution test. Also provided herein is a pharmaceutical aqueous suspension comprising a plurality of moderate release biocompatible, therapeutic nanoparticles having a glass transition temperature between about 39° C. and about 41° C., wherein each of the nanoparticles comprises a therapeutic agent and a block copolymer having at least one hydrophobic portion and at least one hydrophilic portion, and wherein the nanoparticles release between about 50% to about 70% of the therapeutic agent at four hours in an in vitro dissolution test. In another embodiment, a pharmaceutical aqueous suspension is provided that comprises a plurality of slow release biocompatible, therapeutic nanoparticles having a glass transition temperature between about 42° C. and about 50° C., wherein each of the nanoparticles comprises a therapeutic agent and a block copolymer having at least one hydrophobic portion and at least one hydrophilic portion, wherein the nanoparticles release about 50% or less of the therapeutic agent at four hours in an in vitro dissolution test. Such dissolution tests are well known in the art. One such representative test is exemplified below in Example 7. For example, a dissolution test may include placing the suspension 2.5% wt hydroxypropyl cyclodextrin phosphate buffer saline, (e.g. 0.01 M phosphate buffered saline) for 1, 4, 8, 12 days or more.

In general, disclosed compositions may include nanoparticles that include an active agent.

Disclosed nanoparticles may include about 0.1 to about 40 weight percent, 0.2 to about 35 weight percent, about 3 to about 40 weight percent, about 5 to about 30 weight percent, 10 to about 30 weight percent, 15 to 25 weight percent, or even about 4 to about 25 weight percent of an active agent, such as antineoplastic agent, e.g., a taxane agent (for example, docetaxel).

Nanoparticles disclosed herein include one, two, three or more biocompatible and/or biodegradable polymers, such as described herein. For example, a contemplated nanoparticle may include about 10 to about 99 weight percent of one or more block co-polymers that include a biodegradable polymer and polyethylene glycol, and about 0 to about 50 weight percent, or about 0 to about 75 weight percent of a biodegradable homopolymer, e.g. PLA.

Exemplary therapeutic nanoparticles may include about 40 to about 99, or about 50 to about 90 weight percent poly (lactic) acid-poly(ethylene)glycol copolymer or about 40 to about 80 weight percent poly(lactic) acid-poly(ethylene)glycol copolymer. Such poly(lactic) acid-block-poly(ethylene) glycol copolymer may include poly(lactic acid) having a number average molecular weight of about 15 to 20 kDa (or for example about 15 to about 100 kDa, e.g., about 15 to about 80 kDa), and poly(ethylene)glycol having a number average molecular weight of about 2 to about 10 kDa, for example, about 4 to about 6 kDa. For example, a disclosed therapeutic nanoparticle may include about 70 to about 90 weight percent PLA-PEG and about 15 to about 25 weight percent active agent, or about 30 to about 50 weight percent PLA-PEG, about 30 to about 50 weight percent (or about 30 to about 75 weight percent) PLA or PLGA, and about 15 to about 25 weight percent active agent. Such PLA ((poly)lactic acid) may have a number average molecular weight of about 5 to about 10 kDa. Such PLGA (poly lactic-co-glycolic acid) may have a number average molecular weight of about 8 to about 12 kDa.

In other embodiments, nanoparticles disclosed herein include one or more biocompatible and/or biodegradable polymers, for example, a high molecular weight diblock poly (lactic) acid-poly(ethylene)glycol copolymer or a high molecular weight diblock poly(lactic)-co-poly(glycolic) acid-poly(ethylene)glycol copolymer. For example, a diblock poly(lactic) acid-poly(ethylene)glycol copolymer comprises poly(lactic) acid may have a number average molecule weight of about 30 kDa to about 90 kDa, or about 40 kDa to about 90 kDa. In another embodiment, a diblock poly(lactic)-co-poly(glycolic) acid-poly(ethylene)glycol copolymer comprises poly(lactic)-co-poly(glycolic) acid having a number average molecule weight of about 30 kDa to about 90 kDa, or about 40 kDa to about 90 kDa. For example, a contemplated nanoparticle may include about 0.1 to about 40 weight percent of a therapeutic agent and about 10 to about 90 weight percent a diblock poly(lactic) acid-poly(ethylene)glycol copolymer, wherein the diblock poly(lactic) acid-poly (ethylene)glycol copolymer comprises poly(lactic) acid having a number average molecule weight of about 30 kDa to about 90 kDa, or about 40 kDa to about 90 kDa. In one embodiment, the poly(lactic) acid has a number average molecule weight of about 30 kDa. In another embodiment, the poly(lactic) acid has a number average molecule weight of about 50 kDa to about 80 kDa, or about 70 kDa to about 85 kDa. In yet another embodiment, the poly(lactic) acid has a number average molecule weight of about 50 kDa. In some embodiments, the diblock poly(lactic) acid-poly(ethylene) glycol copolymer or the diblock poly(lactic)-co-poly(glycolic) acid-poly(ethylene)glycol copolymer comprises poly (ethylene)glycol having a molecular weight of about 4 kDa to about 6 kDa, or about 4 kDa to about 12 kDa. For example, the poly(ethylene)glycol may have a number average molecule weight of about 5 kDa or 10 kDa.

Disclosed nanoparticles may optionally include about 1 to about 50 weight percent or about 1 to about 70 weight percent poly(lactic) acid or poly(lactic) acid-co-poly (glycolic) acid (which does not include PEG, e.g a homopolymer of PLA), or may optionally include about 1 to about 75 weight percent, or about 10 to about 50 weight percent or about 30 to about 50 weight percent poly(lactic) acid or poly(lactic) acid-co-poly (glycolic) acid. In an embodiment, disclosed nanoparticles may include two polymers, e.g. PLA-PEG and PLA, in a weight ratio of about 40:60 to about 60:40, or about 30:50 to about 50:30, e.g, about 50:50.

Such substantially homopolymeric poly(lactic) or poly(lactic)-co-poly(glycolic) acid may have a weight average molecular weight of about 4.5 to about 130 kDa, for example, about 20 to about 30 kDa, or about 100 to about 130 kDa. Such homopolymeric PLA may have a number average molecule weight of about 4.5 to about 90 kDa, or about 4.5 to about 12 kDa, about 5.5 to about 7 kDa (e.g. about 6.5 kDa), about 15 to about 30 kDa, or about 60 to about 90 kDa. Exemplary homopolymeric PLA may have a number average molecular weight of about 70 or 80 kDa or a weight average molecular weight of about 124 kD. As is known in the art, molecular weight of polymers can be related to an inherent viscosity. In some embodiments, homopolymer PLA may have an inherent viscosity of about 0.2 to about 0.4, e.g. about 0.4; in other embodiments, PLA may have an inherent viscosity of about 0.6 to about 0.8. Exemplary PLGA may have a number average molecular weight of about 8 to about 12 kDa.

For example, provided herein is a biocompatible, therapeutic polymeric nanoparticle comprising about 0.1 to about 40 weight percent of a therapeutic agent; and about 10 to about 90, or about 10 to about 99, or about 70 to about 99 weight percent biocompatible polymer, wherein the biocompatible polymer is selected from the group consisting of a) a diblock poly(lactic) acid-poly(ethylene)glycol copolymer, wherein the diblock poly(lactic) acid-poly(ethylene)glycol copolymer comprises poly(lactic) acid having a number average molecule weight of about 30 kDa to about 90 kDa; and b) a diblock poly(lactic)-co-poly(glycolic) acid-poly(ethylene)glycol copolymer, wherein the diblock poly(lactic)-co-poly(glycolic) acid-poly(ethylene)glycol copolymer comprises poly(lactic)-co-poly(glycolic) acid having a number average molecule weight of about 30 kDa to about 90 kDa. The diblock poly(lactic) acid-poly(ethylene)glycol copolymer or the diblock poly(lactic)-co-poly(glycolic) acid-poly(ethylene)glycol copolymer may include poly(ethylene)glycol having a molecular weight of about 4 kDa to about 12 kDa, for example, a diblock poly(lactic) acid-poly(ethylene)glycol copolymer may include, poly(lactic) acid having a number average molecular weight of about 30 kDa and poly(ethylene)glycol having a number average molecular weight of about 5 kDa, or may include poly(lactic) acid having a number average molecular weight of about 50 kDa to about 80 kDa and poly(ethylene)glycol having a number average molecular weight of about 5 kDa or 10 kDa, e.g., poly(lactic) acid having a number average molecular weight of about 50 kDa and poly(ethylene)glycol having a number average molecular weight of about 5 kDa.

In one embodiment, disclosed therapeutic nanoparticles may include a targeting ligand, e.g., a low-molecular weight PSMA ligand effective for the treatment of a disease or disorder, such as prostate cancer, in a subject in need thereof. In certain embodiments, the low-molecular weight ligand is conjugated to a polymer, and the nanoparticle comprises a certain ratio of ligand-conjugated polymer (e.g., PLA-PEG-Ligand) to non-functionalized polymer (e.g., PLA-PEG or PLGA-PEG). The nanoparticle can have an optimized ratio of these two polymers such that an effective amount of ligand is associated with the nanoparticle for treatment of a disease or disorder, such as cancer.

In some embodiments, disclosed nanoparticles may further comprise about 0.2 to about 10 weight percent PLA-PEG functionalized with a targeting ligand such as disclosed herein, and/or may include about 0.2 to about 10 weight percent poly (lactic) acid-co poly (glycolic) acid block-PEG-functionalized with a targeting ligand. Such a targeting ligand may be, in some embodiments, covalently bound to the PEG, for example, bound to the PEG via an alkylene linker, e.g., PLA-PEG-alkylene-ligand. For example, a disclosed nanoparticle may include about 0.2 to about 10 mole percent PLA-PEG-ligand or poly (lactic) acid-co poly (glycolic) acid-PEG-ligand.)

In some embodiments, disclosed therapeutic particles and/or compositions include targeting or imaging agents such as dyes, for example Evans blue dye. Such dyes may be bound to or associated with a therapeutic particle, or disclosed compositions may include such dyes. For example, Evans blue dye may be used, which may bind or associate with albumin, e.g. plasma albumin.

Disclosed nanoparticles may have a substantially spherical (i.e., the particles generally appear to be spherical), or non-spherical configuration. For instance, the particles, upon swelling or shrinkage, may adopt a non-spherical configuration.

Disclosed nanoparticles may have a characteristic dimension of less than about 1 micrometer, where the characteristic dimension of a particle is the diameter of a perfect sphere having the same volume as the particle. For example, the particle can have a characteristic dimension of the particle can be less than about 300 nm, less than about 200 nm, less than about 150 nm, less than about 100 nm, less than about 50 nm, less than about 30 nm, less than about 10 nm, less than about 3 nm, or less than about 1 nm in some cases. In particular embodiments, disclosed nanoparticles may have a diameter of about 70 nm to about 250 nm, or about 70 nm to about 180 nm, about 80 nm to about 170 nm, about 80 nm to about 130 nm.

In one set of embodiments, the particles can have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety (i.e., a low-molecular weight ligand) of a polymeric conjugate of the present invention, may be present in both the interior and the surface of the particle, but at a higher concentration on the surface than in the interior of the particle, although in some cases, the concentration in the interior of the particle may be essentially nonzero, i.e., there is a detectable amount of the compound present in the interior of the particle.

In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload can thus be contained within the interior of the particle, which can shelter it from the external environment surrounding the particle (or vice versa). For instance, a drug or other payload contained within a particle administered to a subject will be protected from a subject's body, and the body may also be substantially isolated from the drug for at least a period of time.

Disclosed nanoparticles may be stable, for example in a solution that may contain a saccharide, for at least about 24 hours, about 2 days, 3 days, about 4 days or at least about 5 days at room temperature, or at 25° C.

Nanoparticles disclosed herein may have controlled release properties, e.g., may be capable of delivering an amount of active agent to a patient, e.g., to specific site in a patient, over an extended period of time, e.g. over 1 day, 1 week, or more.

DEFINITIONS

"Treating" includes any effect, e.g., lessening, reducing, modulating, or eliminating, that results in the improvement of the condition, disease, disorder and the like.

"Pharmaceutically or pharmacologically acceptable" describes molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

"Individual," "patient," or "subject" are used interchangeably and include any animal, including mammals, such as mice, rats, other rodents, rabbits, dogs, cats, swine, cattle, sheep, horses, or primates, and most preferably humans. The compounds and compositions of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound or composition that will elicit the biological or medical response of a tissue, system, animal or human that is being sought by the researcher, veterinarian, medical doctor or other clinician. The compounds and compositions of the invention are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts, such as calcium, magnesium, sodium, lithium, zinc, potassium, and iron salts Polymers In some embodiments, the nanoparticles disclosed herein include a matrix of polymers and a therapeutic agent.

Contemplated herein are nanoparticles comprising polymers, for example, copolymers. Various molecular weights of polymers are contemplated herein, for example, the weight of a polymer may influence particle degradation rate, solubility, water uptake, and drug release kinetics. The molecular weight of the polymer can be adjusted such that the particle biodegrades in the subject being treated within a reasonable period of time (ranging from a few hours to 1-2 weeks, 3-4 weeks, 5-6 weeks, 7-8 weeks, etc.) For example, a disclosed particle may comprise a copolymer of PLA and PEG or PLGA and PEG, wherein the PLA or PLGA portion may have a number average molecule weight of about 30 kDa to about 90 kDa or about 40 kDa to about 90 kDa, and the PEG portion may have a molecular weight of about 4 kDa to about 6 kDa. In an exemplary embodiment, the PLA or the PLGA portion may have a number average molecule weight of 30 kDa, 50 kDa, 65 kDa, or 80 kDa. The PEG portion may have a molecular weight of about 5 kDa, about 6, 7, 8, or 9 kDa, or about 10 kDa.

Disclosed nanoparticles may include one or more polymers, e.g. a first polymer that may be a co-polymer, e.g. a diblock co-polymer, and optionally a polymer that may be for example a homopolymer. In some embodiments, disclosed nanoparticles include a matrix of polymers. Disclosed therapeutic nanoparticles may include a therapeutic agent that can be associated with the surface of, encapsulated within, surrounded by, and/or dispersed throughout a polymeric matrix.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, a contemplated copolymer (e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a high molecular weight polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly (glycerol sebacate), polyglycolide, polylactide, PLGA, PLA, polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic)-co-poly(glycolic) acid, poly (lactic acid-co-glycolic acid), and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids or polyanhydrides.

In other embodiments, contemplated polyesters for use in disclosed nanoparticles may be diblock copolymers, e.g., PEGylated polymers and copolymers (containing poly(ethylene glycol) repeat units) such as of lactide and glycolide (e.g., PEGylated PLA, PEGylated PGA, PEGylated PLGA), PEGylated poly(caprolactone), and derivatives thereof. For example, a "PEGylated" polymer may assist in the control of inflammation and/or immunogenicity (i.e., the ability to provoke an immune response) and/or lower the rate of clearance from the circulatory system via the reticuloendothelial system (RES), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly (ethylene glycol) repeat units may increase plasma half-life of the polymer (e.g., copolymer, e.g., block copolymer), for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS(N-hydroxysuccinimide) to react a polymer to a PEG group terminating in an amine, by ring opening polymerization techniques (ROMP), or the like.

Other contemplated polymers that may form part of a disclosed nanoparticle may include poly(ortho ester) PEGylated poly(ortho ester), polylysine, PEGylated polylysine, poly (ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof. In other embodiments, polymers can be degradable polyesters bearing cationic side chains. Examples of these polyesters include poly(L-lactide-co-L-lysine), poly (serine ester), poly(4-hydroxy-L-proline ester).

In other embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

PLGA contemplated for use as described herein can be characterized by a lactic acid:glycolic acid ratio of e.g., approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., a PLGA block copolymer or PLGA-PEG block copolymer), may be selected to optimize for various parameters such as water uptake, therapeutic agent release and/or polymer degradation kinetics can be optimized. In other embodiments, the end group of a PLA polymer chain may be a carboxylic acid group, an amine group, or a capped end group with e.g., a long chain alkyl group or cholesterol.

Targeting Moieties

Provided herein are nanoparticles that may include an optional targeting moiety, i.e., a moiety able to bind to or otherwise associate with a biological entity, for example, a membrane component, a cell surface receptor, prostate specific membrane antigen, or the like. A targeting moiety present on the surface of the particle may allow the particle to become localized at a particular targeting site, for instance, a tumor, a disease site, a tissue, an organ, a type of cell, etc. As such, the nanoparticle may then be "target specific." The drug or other payload may then, in some cases, be released from the particle and allowed to interact locally with the particular targeting site.

For example, a targeting portion may cause the particles to become localized to a tumor (e.g., a solid tumor) a disease site, a tissue, an organ, a type of cell, etc. within the body of a subject, depending on the targeting moiety used. For example, a low-molecular weight PSMA ligand may become localized to a solid tumor, e.g., breast or prostate tumors or cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

For example, a contemplated low-molecular weight PSMA ligand that, e.g., may be conjugated to a disclosed copolymer (and thus form, in some embodiments, part of a disclosed nanoparticle) may be represented by:

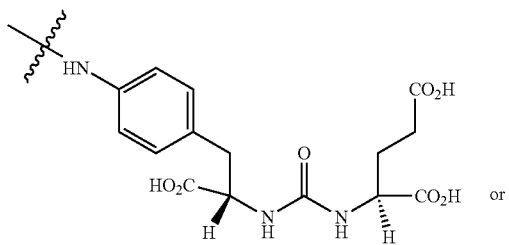 or

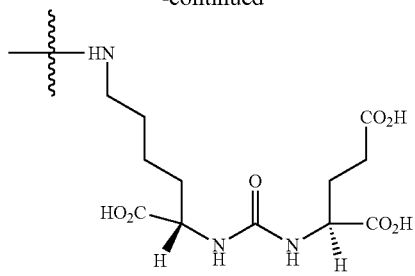

and enantiomers, stereoisomers, rotamers, tautomers, diastereomers, or racemates thereof.

Therapeutic Agents

According to the present invention, any agents including, for example, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered by the disclosed nanoparticles. Exemplary agents to be delivered in accordance with the present invention include, but are not limited to, small molecules (e.g. cytotoxic agents), nucleic acids (e.g., siRNA, RNAi, and mircoRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., breast, lung, or prostate cancer).

The active agent or drug may be a therapeutic agent such as mTor inhibitors (e.g., sirolimus, temsirolimus, or everolimus), vinca alkaloids (e.g. vinorelbine or vincristine), a diterpene derivative, a taxane (e.g. paclitaxel or its derivatives such as DHA-paclitaxel or PG-paxlitaxelor, or docetaxel), a boronate ester or peptide boronic acid compound (e.g. bortezomib), a cardiovascular agent (e.g. a diuretic, a vasodilator, angiotensin converting enzyme, a beta blocker, an aldosterone antagonist, or a blood thinner), a corticosteroid (e.g. budensonide, fluocinonide, triamcinolone, mometasone, amcinonide, halcinonide, ciclesonide, beclomethansone), an antimetabolite or antifolate agent (e.g. methotrexate), a chemotherapeutic agent (e.g. epothilone B), a nitrogen mustard agent (e.g. bendamustine), or the active agent or drug may be an siRNA.

In one set of embodiments, the payload is a drug or a combination of more than one drug. Such particles may be useful, for example, in embodiments where a targeting moiety may be used to direct a particle containing a drug to a particular localized location within a subject, e.g., to allow localized delivery of the drug to occur. Exemplary therapeutic agents include chemotherapeutic agents such as doxorubicin (adriamycin), gemcitabine (gemzar), daunorubicin, procarbazine, mitomycin, cytarabine, etoposide, methotrexate, 5-fluorouracil (5-FU), vinca alkaloids such as vinblastine, vinoelbine, vindesine, or vincristine; bleomycin, taxanes such as paclitaxel (taxol) or docetaxel (taxotere), mTOR inhibitors such as sirolimus, temsirolimus, or everolimus, aldesleukin, asparaginase, boronate esters or peptide boronic acid compounds such as bortezomib, busulfan, carboplatin, cladribine, camptothecin, CPT-11, 10-hydroxy-7-ethylcamptothecin (SN38), dacarbazine, S—I capecitabine, ftorafur, 5' deoxyfluorouridine, UFT, eniluracil, deoxycytidine, 5-azacytosine, 5-azadeoxycytosine, allopurinol, 2-chloroadenosine, trimetrexate, aminopterin, methylene-10-deazaminopterin (MDAM), oxaplatin, picoplatin, tetraplatin, satraplatin, platinum-DACH, ormaplatin, CI-973, JM-216, epirubicin, etoposide phosphate, 9-aminocamptothecin, 10,11-methylenedioxycamptothecin, karenitecin, 9-nitrocamptothecin, TAS 103, L-phenylalanine mustard, ifosphamidemefosphamide, perfosfamide, trophosphamide carmustine, semustine, bendamustine, epothilones A-E, tomudex, 6-mercaptopurine, 6-thioguanine, amsacrine, karenitecin, acyclovir, valacyclovir, ganciclovir, amantadine, rimantadine, lamivudine, zidovudine, bevacizumab, trastuzumab, rituximab, budesonide, and combinations thereof, or the therapeutic agent may be an siRNA.

In some embodiments, contemplated nanoparticles do not include a taxane (e.g. do not include docetaxel). In other embodiments, contemplated nanoparticles do not include a vinca alkaloid or a mTOR inhibitor.

Non-limiting examples of potentially suitable drugs include anti-cancer agents, including, for example, docetaxel, mitoxantrone, and mitoxantrone hydrochloride. In another embodiment, the payload may be an anti-cancer drug such as 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizdng morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cyclosporine, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C uihibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone Bl, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine or vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

In an embodiment, an active agent may (or may not be) conjugated to e.g. a disclosed hydrophobic polymer that forms part of a disclosed nanoparticle, e.g an active agent may be conjugated (e.g. covalently bound, e.g. directly or through a linking moiety) to PLA or PGLA, or a PLA or PLGA portion of a copolymer such as PLA-PEG or PLGA-PEG.

Preparation of Nanoparticles

In some embodiments, disclosed nanoparticles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethysulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Figure 2A:
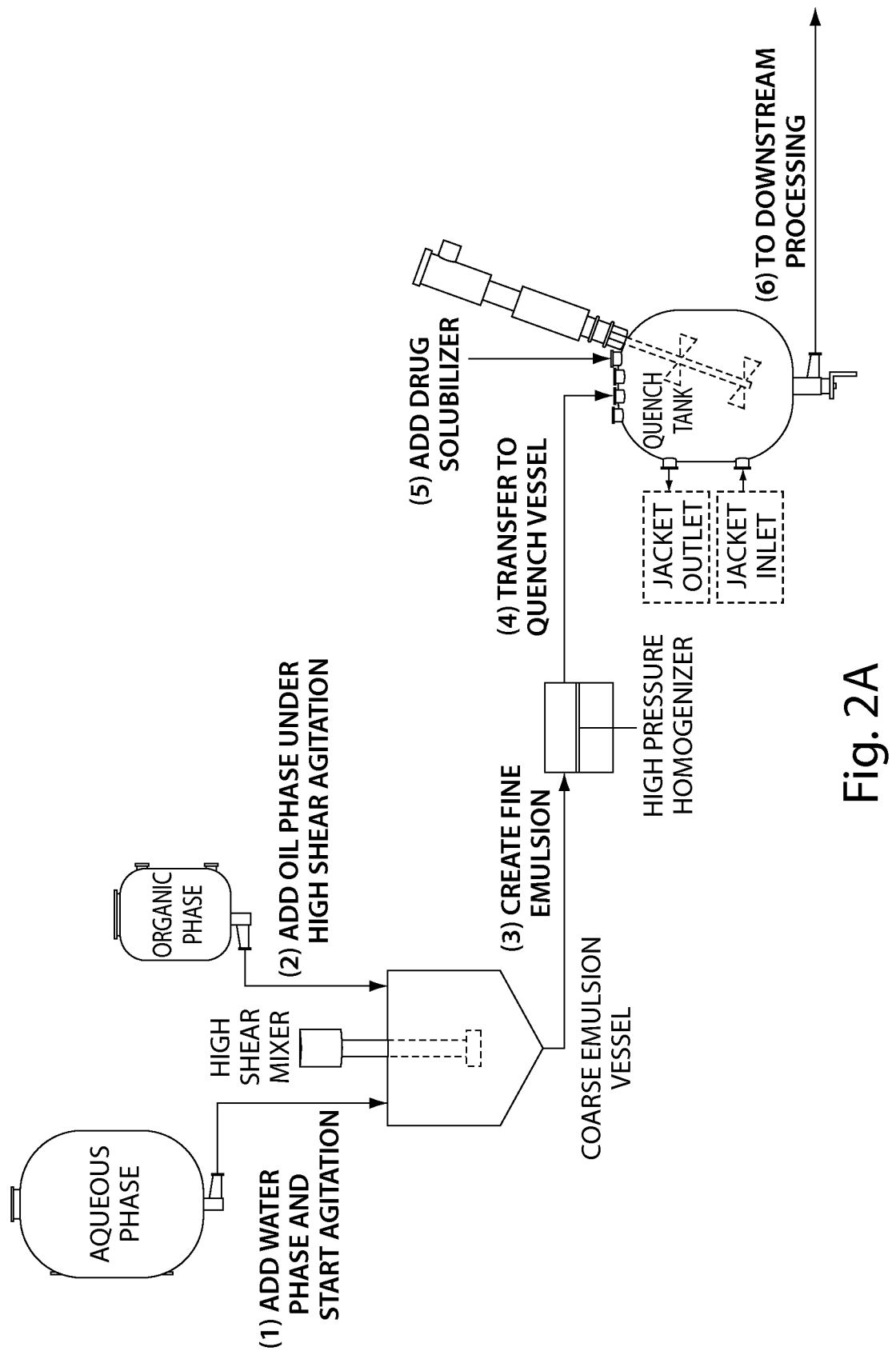
FIGS. 2A and 2B are flow diagrams for a disclosed emulsion process.
Figure 2B:
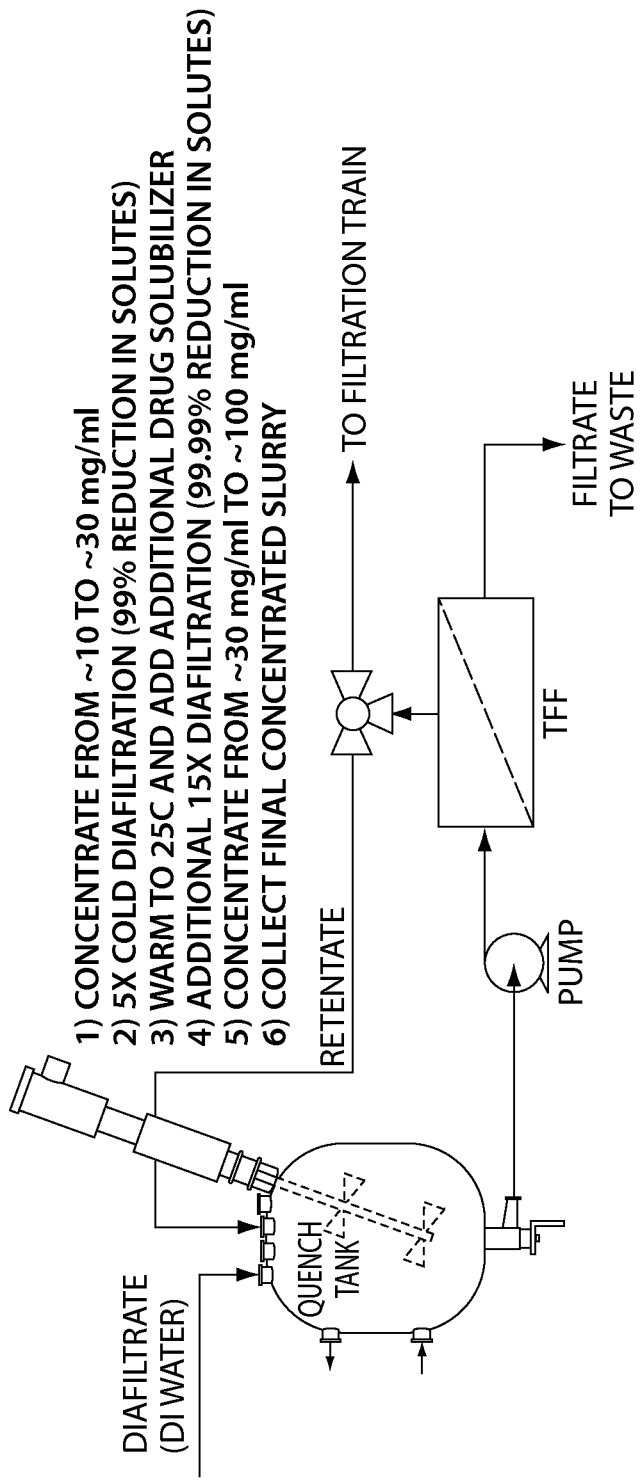

In another embodiment, a nanoemulsion process is provided, such as the process represented in FIGS. 1, 2A, and 2B. For example, a therapeutic agent, a first polymer (for example, a diblock co-polymer such as PLA-PEG or PLGA-PEG) and an optional second polymer (e.g., (PL(G)A-PEG or PLA), with an organic solution to form a first organic phase. Such first phase may include about 5 to about 50% weight solids, e.g about 5 to about 40% solids, or about 10 to about 30% solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or the like, and combinations thereof. In an embodiment, the organic phase may include benzyl alcohol, ethyl acetate, and combinations thereof. The second phase can be between about 1 and 50 weight %, e.g., about 5-40 weight %, solids. The aqueous solution can be water, optionally in combination with one or more of sodium cholate, ethyl acetate, polyvinyl acetate and benzyl alcohol.

For example, the oil or organic phase may use a solvent that is only partially miscible with the nonsolvent (water). Therefore, when mixed at a low enough ratio and/or when using water pre-saturated with the organic solvents, the oil phase remains liquid. The oil phase may bee emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate and pre-saturated with ethyl acetate and benzyl alcohol.

Emulsifying the second phase to form an emulsion phase may be performed in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer, e.g., by using 1, 2, 3 or more passes through a homogenizer. For example, when a high pressure homogenizer is used, the pressure used may be about 1000 to about 8000 psi, about 2000 to about 4000 psi 4000 to about 8000 psi, or about 4000 to about 5000 psi, e.g., about 2000, 2500, 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. Quenching may be performed at least partially at a temperature of about 5° C. or less. For example, water used in the quenching may be at a temperature that is less that room temperature (e.g., about 0 to about 10° C., or about 0 to about 5° C.).

In some embodiments, not all of the therapeutic agent (e.g., docetaxel) is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, or sodium cholate. For example, Tween-80 may added to the quenched nanoparticle suspension to solubilize the free drug and prevent the formation of drug crystals. In some embodiments, a ratio of drug solubilizer to therapeutic agent (e.g., docetaxel) is about 100:1 to about 10:1.

The solubilized phase may be filtered to recover the nanoparticles. For example, ultrafiltration membranes may be used to concentrate the nanoparticle suspension and substantially eliminate organic solvent, free drug, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g., about 0 to about 5° C., or 0 to about 10° C.) may added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. For example, filtering may include processing about 1 to about 6 diavolumes at about 0 to about 5° C., and processing at least one diavolume (e.g., about 1 to about 3 or about 1-2 diavolumes) at about 20 to about 30° C.

After purifying and concentrating the nanoparticle suspension, the particles may be passed through one, two or more sterilizing and/or depth filters, for example, using ~0.2 μm depth pre-filter.

In another embodiment of preparing nanoparticles, an organic phase is formed composed of a mixture of a therapeutic agent, e.g., docetaxel, and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. The quench:emulsion ratio is approximately 8.5:1. Then a solution of Tween (e.g., Tween 80) is added to the quench to achieve approximately 2% Tween overall. This serves to dissolve free, unencapsulated drug. The nanoparticles are then isolated through either centrifugation or ultrafiltration/diafiltration.

It will be appreciated that the amounts of polymer and therapeutic or active agent that are used in the preparation of the formulation may differ from a final formulation. For example, some active agent may not become completely incorporated in a nanoparticle and such free therapeutic agent may be e.g., filtered away.

Pharmaceutical Compositions

Nanoparticles disclosed herein may be combined with pharmaceutical acceptable carriers to form a pharmaceutical composition, according to another aspect of the disclosure. As would be appreciated by one of skill in this art, the carriers may be chosen based on the route of administration as described below, the location of the target issue, the drug being delivered, the time course of delivery of the drug, etc.

The pharmaceutical compositions of this disclosure can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present disclosure are administered to a subject in need thereof systemically, e.g., parenterally, or by IV infusion or injection.

In some embodiments, a composition suitable for freezing is contemplated, including nanoparticles disclosed herein and a solution suitable for freezing, e.g., a sucrose and/or a salt solution is added to the nanoparticle suspension. The sucrose may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water is about 3-30%/10-30%/50-90% (w/w/w) or about 5-10%/10-15%/80-90% (w/w/w). For example, such solution may include nanoparticles as disclosed herein, about 5% to about 20% by weight sucrose and an ionic halide such as sodium chloride, in a concentration of about 10-100 mM.

Compositions and Methods of Treatment

Nanoparticles disclosed herein may be combined with pharmaceutical acceptable carriers to form a pharmaceutical composition. As would be appreciated by one of skill in this art, the carriers may be chosen based on the route of administration as described below, the location of the target issue, the drug being delivered, the time course of delivery of the drug, etc.

The pharmaceutical compositions and particles disclosed herein can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, disclosed nanoparticles may be administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Disclosed nanoparticles may be formulated in dosage unit form for ease of administration and uniformity of dosage. The expression "dosage unit form" as used herein refers to a physically discrete unit of nanoparticle appropriate for the patient to be treated. For any nanoparticle, the therapeutically effective dose can be estimated initially either in cell culture assays or in animal models, usually mice, rabbits, dogs, or pigs. An animal model may also be used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an exemplary embodiment, a pharmaceutical composition is disclosed that includes a plurality of nanoparticles each comprising a therapeutic agent and a pharmaceutically acceptable excipient.

In some embodiments, a composition suitable for freezing is contemplated, including nanoparticles disclosed herein and a solution suitable for freezing, e.g., a sugar (e.g. sucrose) solution is added to a nanoparticle suspension. The sucrose may, e.g., act as a cryoprotectant to prevent the particles from aggregating upon freezing. For example, provided herein is a nanoparticle formulation comprising a plurality of disclosed nanoparticles, sucrose and water; wherein, for example, the nanoparticles/sucrose/water are present at about 5-10%/10-15%/80-90% (w/w/w).

In some embodiments, therapeutic particles disclosed herein may be used to treat, alleviate, ameliorate, relieve, delay onset of, inhibit progression of, reduce severity of, and/or reduce incidence of one or more symptoms or features of a disease, disorder, and/or condition. For example, disclosed therapeutic particles, that include taxane, e.g., docetaxel, may be used to treat cancers such as breast, lung, or prostate cancer in a patient in need thereof. Other types of tumors and cancer cells to be treated with therapeutic particles of the present invention include all types of solid tumors, such as those which are associated with the following types of cancers: lung, squamous cell carcinoma of the head and neck (SCCHN), pancreatic, colon, rectal, esophageal, prostate, breast, ovarian carcinoma, renal carcinoma, lymphoma and melanoma. The tumor can be associated with cancers of (i.e., located in) the oral cavity and pharynx, the digestive system, the respiratory system, bones and joints (e.g., bony metastases), soft tissue, the skin (e.g., melanoma), breast, the genital system, the urinary system, the eye and orbit, the brain and nervous system (e.g., glioma), or the endocrine system (e.g., thyroid) and is not necessarily the primary tumor. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, non-small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system.

Disclosed methods for the treatment of cancer (e.g. breast or prostate cancer) may comprise administering a therapeutically effective amount of the disclosed therapeutic particles to a subject in need thereof, in such amounts and for such time as is necessary to achieve the desired result. In certain embodiments of the present invention a "therapeutically effective amount" is that amount effective for treating, alleviating, ameliorating, relieving, delaying onset of, inhibiting progression of, reducing severity of, and/or reducing incidence of one or more symptoms or features of e.g. a cancer being treated.

In some embodiments, disclosed therapeutic nanoparticles that include epothilone, e.g. epothilone B may be used to treat cancers such as breast, prostate, colon, glioblastoma, acute lymphoblastic leukemia, osteosarcoma, non-Hodgkin's lymphoma, or lung cancer such a non-small cell lung cancer, in a patient in need thereof.

In other embodiments, disclosed therapeutic nanoparticles that include a corticosteroid such as budesonide may be used to treat asthma, osteoarthritis, dermatitis, and inflammatory disorders such as inflammatory bowel disease, ulcerative colitis, and/or Crohn's disease (treatment of cancers such as colon cancer is also contemplated.)

Drug Release Rate

This disclosure relates in part to a method for predicting and controlling the rate of drug release from nanoparticles by measurement of the glass transition temperature ($T_g$) of drug loaded nanoparticles in aqueous suspension. For example, measurement under suspension conditions may be needed to manipulate the chemical composition and physical properties of the nanoparticle in the blood stream upon IV administration. Nanoparticle formulations can also be designed to exhibit desired drug release rates based upon the $T_g$ of nanoparticles.

The glass transition temperature ($T_g$) of drug bearing nanoparticles in aqueous suspension may be an indicator of the drug release characteristics of the nanoparticle. Identification of nanoparticle suspension $T_g$ allows for its use as a predictor of drug release properties, enables rational design of nanoparticulate polymer and drug formulations that possess desired drug release rates, and additionally allows rapid screening of formulations to identify high value targets for further investigation.

Forming nanoparticles using an emulsion process typically yields an amorphous solid dispersion of drug in polymer. Depending on its chemical structure, the polymer may partially crystallize; however, often the lack of stereo-regularity of repeating units along the polymer chain causes the polymer to adopt an amorphous state. This rigid glassy state is similar to that obtained by cooling a polymer melt. The melt phase is characterized by rubber like properties. The transition to the glassy state is accompanied by changes in the polymer material properties including hardness, Young's modulus, and heat capacity. Several techniques that monitor changes in these properties can be used to determine the temperature (or temperature range) over which this rubber to glass transition, known as the glass transition temperature ($T_g$), occurs. The $T_g$ can be, for example, dependent upon the purity of the polymer. For example, the presence of small molecules, such as drug molecules or active agents, solvent or non-solvent molecules (i.e., water), in nanoparticles can affect the $T_g$ of the polymer, e.g., high surface to volume ratio of nanoparticles may contribute to the water content of the polymer phase. The $T_g$ of polymeric nanoparticles in an aqueous suspension may be distinctly different from that of a mesoscopic polymer-drug mixture of the same chemical composition or that of drug-bearing nanoparticles in dry powder form.

Drug within the nanoparticles may be molecularly dispersed or may form nanocrystals of dimensions smaller than those of the polymer nanoparticle. In both instances, the diffusional-based release of drug from the nanoparticle is dependent upon its transport through the polymer matrix and into the surrounding aqueous phase. As such, the drug's intrinsic solubility in the polymer matrix, its diffusion coefficient, the diffusion path length, viscosity as well as temperature of the polymer matrix can be factors in the rate of drug release from the nanoparticles. For example, upon intravenous injection, nanoparticles may quickly equilibrate to physiological temperature (37° C.) and therefore, the material properties of the polymer matrix at this temperature can influence the rate of drug release. Drug diffusion across the polymer and its release from the nanoparticle can be slower if the polymeric matrix is in a rigid glassy state at 37° C., and relatively faster if the polymer matrix is in a rubbery state at this temperature. That is, under physiological conditions, nanoparticles that possess a $T_g$ at or below 37° C. may release drug at a faster rate than those possessing a $T_g$ above 37° C.

For example, nanoparticles comprising PLA-PEG and low molecular weight PLA (e.g., 6.5 kDa PLA) have a lower $T_g$ than nanoparticles comprising PLA-PEG alone. Addition of high molecular weight PLA (e.g., 75 kDa PLA) to nanoparticles containing PLA-PEG raises the $T_g$ above that of nanoparticles comprising PLA-PEG alone. By varying the type and amount of homopolymer, such as PLA, in a nanoparticle composition, the $T_g$ can be altered which then directly affects the rate of drug release from the nanoparticles. Similarly, the Tg of the nanoparticles that include diblock copolymers (e.g. PLA-PEG) only is typically a function of the mlar mas of the core forming block (e.g. PLA). Glass transition temperatures of the polymeric components of nanoparticles may be used to select compositions that impart a range of thermal characteristics to particles and enables prediction of their drug release properties.

This disclosure relates in part to methods for screening polymer and drug systems to identify combinations that have the necessary thermal characteristics (glass transition temperatures) associated with a desired drug release profile. By assaying the $T_g$ of a given nanoparticle composition, the drug release rate of the nanoparticles can be predicted. Screening based on $T_g$, or $T_b$, the temperature at which the nanoparticle glass transition begins, can rapidly identify nanoparticle polymer combinations that release drug at a desired rate. In combination with a high throughput means of nanoparticle fabrication, this disclosure allows for rapid screening of polymer and drug combinations to arrive at a select number of systems that can then be subjected to traditional more detailed drug release studies.

For example, analysis of drug loaded nanoparticles by Differential Scanning calorimetry (DSC) under aqueous suspension conditions demonstrates the correlation between drug release rate and nanoparticle glass transition temperature. DSC is a technique in which the heat flow rate into a substance and a reference is measured as a function of temperature while the substance and reference are subjected to a controlled temperature program. DSC techniques include Heat Flux DSC and Power Compensation DSC. In Heat Flux DSC, the instrument consists of a single cell containing reference and sample holders separated by a bridge that acts as a heat-leak. This assembly sits within a heating block or furnace that is a constant temperature body. Thermocouples in thermal contact with the sample and reference platforms measure the temperatures of the sample pan and reference pan while the heating block temperature is increased (heating cycle) or decreased (cooling cycle) at a given rate, for example 10° C./minute. The experimental output consists of the temperature differential (or heat flow differential in Watt/gram) between the sample and reference pans plotted against the heating block temperature. In contrast, in Power Compensation DSC, the instrument consists of two separate but identical furnaces, one housing the sample and the other the reference. In this case, the power differential necessary to maintain the two furnaces at constant temperature serves as the basis for differential heat flow. The experimental output is analogous to that in Heat Flux DSC.

The glass transition temperatures of nanoparticles in aqueous suspension can also be determined using Modulated Differential Scanning calorimetry (MDSC). In this technique, a sinusoidal temperature modulation is overlaid on a linear heating or cooling rate. This is combined with a mathematical procedure separates the total heat flow (similar to what is observed in conventional DSC) into reversing and non-reversing heat flow components. The reversing heat flow component derives from the heat capacity of the sample as well as events that respond directly to changes in the ramp rate and are reversing at the time and temperature at which they are observed. In other words, events (e.g., glass transition temperature) that are fast enough to be reversing on the time scale of the sinusoidal temperature modulation will contribute to this signal. Events that do not respond to changes in ramp rate (e.g., enthalpic relaxation at the glass transition temperature) are observed in the non-reversing heat flow component. By separating the reversing and non-reversing heat flow components of the total heat flow, MDSC allows the separation of glass transition events from enthalpic relaxation events. Thus, unlike conventional DSC, with MDSC accurate determination of the glass transition temperature of samples that exhibit strong enthalpic relaxations at the glass transition temperature becomes possible. For example, when nanoparticle suspensions are analyzed using MDSC and the reversing heat flow component plotted against sample temperature, the curves may appear similar to those observed in conventional DSC (total heat flow curves versus sample temperature), confirming that the transitions observed by conventional DSC are glass transition events rather than ethalpic relaxations.

The rate of drug release can be measured using an in vitro dissolution (i.e., suspension and centrifugation) technique. Nanoparticles are suspended in a release medium, such as hydroxypropyl βCD (Trapsol) in PBS. After a period of time, the suspension is centrifuged, and a sample of the medium from the upper part of the centrifuged suspension is withdrawn without causing turbulence to avoid re-suspending the nanoparticle pellet at the centrifuge tube bottom. The sample is then analyzed by HPLC to determine the amount of drug released from the nanoparticles.

In one aspect, the disclosure provides a pharmaceutical aqueous suspension comprising a plurality of nanoparticles, having a glass transition temperature between about 37° C. and about 50° C., wherein each of the nanoparticles comprises a therapeutic agent and a block copolymer having at least one hydrophobic portion and at least one hydrophilic portion.

The hydrophobic portion may be selected from poly(D,L-lactic) acid and poly(lactic acid-co-glycolic acid). The hydrophilic portion may be poly(ethylene)glycol. The nanoparticles may further comprise poly(D,L-lactic) acid or poly(lactic) acid-co-poly(glycolic) acid.

In one embodiment, the nanoparticles may comprise about 0.2 to about 35 weight percent of a therapeutic agent; about 10 to about 99 weight percent poly(D,L-lactic) acid-block-poly(ethylene)glycol copolymer or poly(lactic)-co-poly(glycolic) acid-block-poly(ethylene)glycol copolymer; and about 0 to about 50 or 0 to about 75 weight percent poly(D,L-lactic) acid or poly(lactic) acid-co-poly(glycolic) acid. In another embodiment, the poly(D,L-lactic) acid portion of the copolymer has a number average molecular weight of about 16 kDa, and the poly(ethylene)glycol portion of the copolymer has a number average molecular weight of about 5 kDa. In another embodiment, the poly(D,L-lactic) acid portion of the copolymer has a number average molecular weight of about 50 kDa, and the poly(ethylene)glycol portion of the copolymer has a number average molecular weight of about 5 kDa. In an embodiment, the poly(D,L-lactic) acid has a number average molecular weight of about 6.5 kDa. In another embodiment, the poly(D,L-lactic) acid has a number average molecular weight of about 75 kDa.

In one embodiment, a provided aqueous suspension of nanoparticles has a glass transition temperature may be about 37° C. to about 39° C., 37° C. to about 39.5° C., 39.5° C. to about 41° C., about 42° C. to about 50° C., or about 42° C. to about 44° C. In another embodiment, an aqueous suspension of nanoparticles may have a glass transition temperature that may be about 37° C. to about 38° C. In some embodiments, provided nanoparticles or suspensions do not include nanoparticles or suspensions having a glass transition temperature of 40° C., or 39.5° C. to about 41° C. The term "about" in the context of glass transition temperature generally means±0.5° C. The glass transition temperature may be measured by Heat Flux Differential Scanning calorimetry, Power Compensation Differential Scanning calorimetry, and/or Modulated DSC.

In one embodiment, disclosed nanoparticles release less than about 50% of the therapeutic agent as determined in an in vitro dissolution test at a 4 hour time point. In another embodiment, the nanoparticles release between about 50 to about 70% of the therapeutic agent as determined in an in vitro dissolution test at a 4 hour time point. In another embodiment, the nanoparticles release between about 70 to about 100% of the therapeutic agent as determined in an in vitro dissolution test at a 4 hour time point.

In another aspect, the disclosure provides a method for determining the drug release rate of a therapeutic polymeric nanoparticle composition, comprising:

a) providing at least one first plurality of polymeric nanoparticles comprising a first therapeutic agent, a first block copolymer having at least one hydrophobic portion and at least one hydrophilic portion, and optionally poly(D,L-lactic) acid or poly(lactic) acid-co-poly(glycolic) acid;

b) determining the nanoparticle glass transition temperature for the at least one first plurality of polymeric nanoparticles;

c) determining the drug release rate from the at least one first plurality of polymeric nanoparticles; and d) determining the correlation between the nanoparticle glass transition temperature and the drug release rate for the at least one first plurality of polymeric nanoparticles.

In an embodiment, the method for determining the drug release rate of a therapeutic polymeric nanoparticle composition further comprises:

e) providing at least one second plurality of polymeric nanoparticles comprising a second therapeutic agent, a second block copolymer having at least one hydrophobic portion and at least one hydrophilic portion, and optionally poly(D,L-lactic) acid or poly(lactic) acid-co-poly(glycolic) acid, wherein the second therapeutic agent and second block copolymer may be the same or different as the first therapeutic agent and first block copolymer;

f) determining the nanoparticle glass transition temperature for the at least one second plurality of polymeric nanoparticles; and g) predicting the drug release rate for the at least one second plurality of polymeric nanoparticles based on the nanoparticle glass transition temperature for the at least one second plurality of polymeric nanoparticles and the correlation determined in step d).

In another embodiment, the method for determining the drug release rate of a therapeutic polymeric nanoparticle composition further comprises confirming the predicted drug release rate from the at least one second plurality of polymeric nanoparticles using an in vitro dissolution test.

The first and/or second therapeutic agent may be a taxane agent, such as docetaxel.

In one embodiment, the hydrophobic portions of the first and second block copolymers can each be selected from poly(D,L-lactic) acid and poly(lactic acid-co-glycolic acid). In an embodiment, the hydrophilic portions of the first and second block copolymers can each be poly(ethylene)glycol. In one embodiment, the first and/or second block copolymer may comprise about 0.2 to about 35 weight percent of a therapeutic agent; about 10 to about 99 weight percent poly (D,L-lactic) acid-block-poly(ethylene)glycol copolymer or poly(lactic)-co-poly(glycolic) acid-block-poly(ethylene) glycol copolymer; and about 0 to about 50 weight percent poly(D,L-lactic) acid or poly(lactic) acid-co-poly(glycolic) acid. In an embodiment, the poly(D,L-lactic) acid portion of the first and/or second block copolymer may have a number average molecular weight of about 16 kDa or about 50 kDa, and the poly(ethylene)glycol portion of the first and/or second block copolymer may have a weight average molecular weight of about 5 kDa. In another embodiment, the poly(D, L-lactic) acid may have a number average molecular weight of about 8.5 kDa. In one embodiment, the poly(D,L-lactic) acid may have a number average molecular weight of about 75 kDa. In an embodiment, the poly(D,L-lactic) acid portion of the first and/or second block copolymer may have a number average molecular weight of about 50 kDa, and the poly (ethylene)glycol portion of the first and/or second block copolymer may have a number average molecular weight of about 5 kDa.

Also provided herein is a method for screening nanoparticle suspensions (e.g. to identify a predetermined release rate of a therapeutic agent), comprising:

i) providing a suspension comprising a first plurality of polymeric nanoparticles, wherein the nanoparticles each comprise a therapeutic agent, a block copolymer having at least one hydrophobic portion and at least one hydrophilic portion, and a homopolymer selected from poly(D,L-lactic) acid or poly(lactic) acid-co-poly(glycolic) acid;

ii) determining the glass transition temperature for the suspension;

iii) increasing or decreasing the amount of the homopolymer in the first plurality of polymeric nanoparticles; and iv) repeating steps i)-iii) until a suspension with a desired glass transition temperature is achieved.

For example, provided herein is a method for screening nanoparticle suspensions to identify a suspension having a specific release rate, comprising:

a) separately preparing a plurality of suspensions having nanoparticles comprising a therapeutic agent, a block copolymer having at least one hydrophobic portion and at least one hydrophilic portion, and optionally a homopolymer selected from poly(D,L-lactic) acid or poly(lactic) acid-co-poly(glycolic) acid; wherein each suspension is in a separate compartment, each suspension comprises a pre-determined molecular weight of the block copolymer and if present, a pre-determined molecular weight of the homopolymer;

b) determining the glass transition temperature of each of the suspensions;

c) identifying the suspension having a pre-determined glass transition temperature.

EXAMPLES

The invention now being generally described, it will be more readily understood by reference to the following examples which are included merely for purposes of illustration of certain aspects and embodiments of the present invention, and are not intended to limit the invention in any way.

Example 1

Preparation of PLA-PEG

The synthesis is accomplished by ring opening polymerization of d,l-lactide with α-hydroxy-ω-methoxypoly(ethylene glycol) as the macro-initiator, and performed at an elevated temperature using Tin (II) 2-Ethyl hexanoate as a catalyst, as shown below (PEG Mn≈5,000 Da; PLA Mn≈16,000 Da; PEG-PLA $M_n$≈21,000 Da)

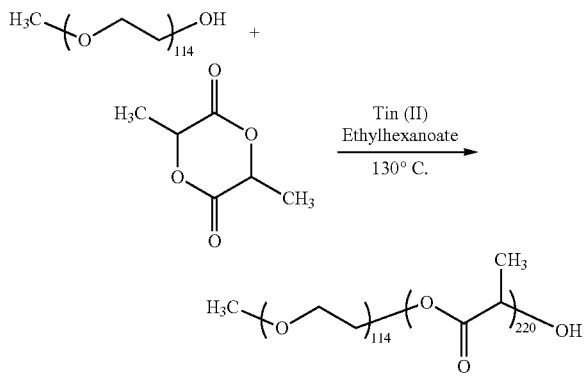

The polymer is purified by dissolving the polymer in dichloromethane, and precipitating it in a mixture of hexane and diethyl ether. The polymer recovered from this step shall be dried in an oven.

Example 2

Nanoparticle Preparation—Emulsion Process

An organic phase is formed composed of a mixture of docetaxel (DTXL) and polymer (homopolymer, co-polymer, and/or co-polymer with ligand). The organic phase is mixed with an aqueous phase at approximately a 1:5 ratio (oil phase:aqueous phase) where the aqueous phase is composed of a surfactant and some dissolved solvent. In order to achieve high drug loading, about 30% solids in the organic phase is used. The primary, coarse emulsion is formed by the combination of the two phases under simple mixing (stir bar) or through the use of a rotor stator homogenizer. The primary emulsion is then formed into a fine emulsion through the use of a high pressure homogenizer. Generally 1-3 passes through a 100 micron Z-chamber at 9000 psig is used to produce an emulsion with the target particle size.

The fine emulsion is then quenched by addition to deionized water at a given temperature under mixing. In the quench unit operation, the emulsion is added to a cold aqueous quench under agitation. This serves to extract a significant portion of the oil phase solvents, effectively hardening the nanoparticles for downstream filtration. The quench:emulsion ratio is approximately 5:1.

A solution of 35% (wt %) of Tween 80 is added to the quench to achieve approximately 4% Tween 80 overall After the emulsion is quenched a solution of Tween-80 is added which acts as a drug solubilizer, allowing for effective removal of unencapsulated drug during filtration.

The temperature must remain cold enough with a dilute enough suspension (low enough concentration of solvents) to remain below the $T_g$ of the particles. If the Q:E ratio is not high enough, then the higher concentration of solvent plasticizes the particles and allows for drug leakage. Conversely, colder temperatures allow for high drug encapsulation at low Q:E ratios (to ~3:1), making it possible to run the process more efficiently.

The nanoparticles are then isolated through a tangential flow filtration process to concentrate the nanoparticle suspension and buffer exchange the solvents, unencapsulated drug, and drug solubilizer from the quench solution into water. A regenerated cellulose membrane is used with a molecular weight cutoffs (MWCO) of 300. A constant volume diafiltration (DF) is performed to remove the quench solvents, free drug and Tween-80. To perform a constant-volume DF, buffer is added to the retentate vessel at the same rate the filtrate is removed.

The filtered nanoparticle slurry is then thermal cycled to an elevated temperature during workup. A small portion (typically 5-10%) of the encapsulated drug is released from the nanoparticles very quickly after its first exposure to 25° C. Because of this phenomenon, batches that are held cold during the entire workup are susceptible to free drug or drug crystals forming during delivery or any portion of unfrozen storage.

After the filtration process the nanoparticle suspension is passed through a sterilizing grade filter (0.2 μm absolute). Pre-filters are used to protect the sterilizing grade filter in order to use a reasonable filtration area/time for the process. The filters normally used are Pall SXMPDD1404 (KS50P/EKSP double layer, (0.1-0.3 μm Nominal); Pall Life Sciences Supor EKV 0.65/0.2 micron sterilizing grade PES filter.

0.2 m² of filtration surface area per kg of nanoparticles for depth filters and 1.3 m² of filtration surface area per kg of nanoparticles for the sterilizing grade filters can be used.

Example 3

Differential Scanning Calorimetry of Polymers

The glass transition temperatures of the nanoparticles and their polymeric components were measured using either a TA Instruments Q200 or a TA Instruments Q2000 Heat Flux DSC equipped with the Tzero ($T_o$) technology. The sample pan (containing either 20-70 μL nanoparticle suspension or 3-10 mg polymer) and reference pans (comprised of an empty sample pan) were heated between 4° C. and 70° C. at a ramp rate of 10° C. (or 20° C.) per minute. High purity dry nitrogen was used to purge the furnace during analysis.

In conventional Heat Flux DSC, two thermocouples, one each for the sample and reference pans are used. When the furnace temperature is ramped at a constant heating rate (for example 10° C. per minute), the sample temperature ($T_s$) lags behind the reference temperature ($T_r$) to an extent equal to the heat capacity of the sample provided the sample and reference pan masses are identical. The temperature difference, $\Delta T = T_s - T_r$, is recorded as a function of furnace block temperature. Typically, the instrument output consists of the heat flow rate per unit mass plotted against heating block temperature. The heat flow rate per unit mass in Watt/g (y-axis), consists of $\Delta T/R$, where R is the thermal resistance of the Constantan bridge that connects (and supports) the reference and sample pans. Thus, when the experiment is started, the DSC signal shifts from zero to a steady state value $(T_s-T_r)/R$, establishing the experimental baseline. When a glass transition is encountered either on a heating cycle or cooling cycle, the steady state value shifts as a result of increase in the sample heat capacity above the sample $T_g$. Typically, the temperature at half height of the heat capacity change, ½ $\Delta Cp$ is defined as the sample $T_g$.

In Heat Flux DSC's equipped with $T_0$ technology, a third thermocouple measures the temperature ($T_0$) of the Constantan bridge that connects (and supports) the reference and sample pans and the heat flow equation consists of three additional terms, one to account for the different resistances of the sample and reference cells and one each for the differences in thermal capacitance and heating rates. All DSC data presented below was acquired on instruments equipped with $T_0$ technology. Additionally, the data was processed using the "T4 mode", i.e., using the four term heat flow equation. For some experiments, the "T4P mode" was used. In this mode, a correction for differences between sample and reference pan weights was used in addition to those described for the T4 mode.

Solid polymer samples, including poly(D,L-lactide)-block-poly(ethylene glycol) (PLA-PEG, Mn PLA block=16 kDa; Mn PEG block=5 kDa), poly(D,L-lactide) (PLA, Mn=6 kDa), and poly(D,L-lactide) (PLA, Mn=75 kDa) were analyzed using hermetically sealed pans, and instrument constants were determined using the T4 mode. The DSC results obtained are shown in FIGS. 3 through 7 where the glass transition temperature was assigned using the point of inflexion method ($T_g$=point of largest slope).

Figure 3:
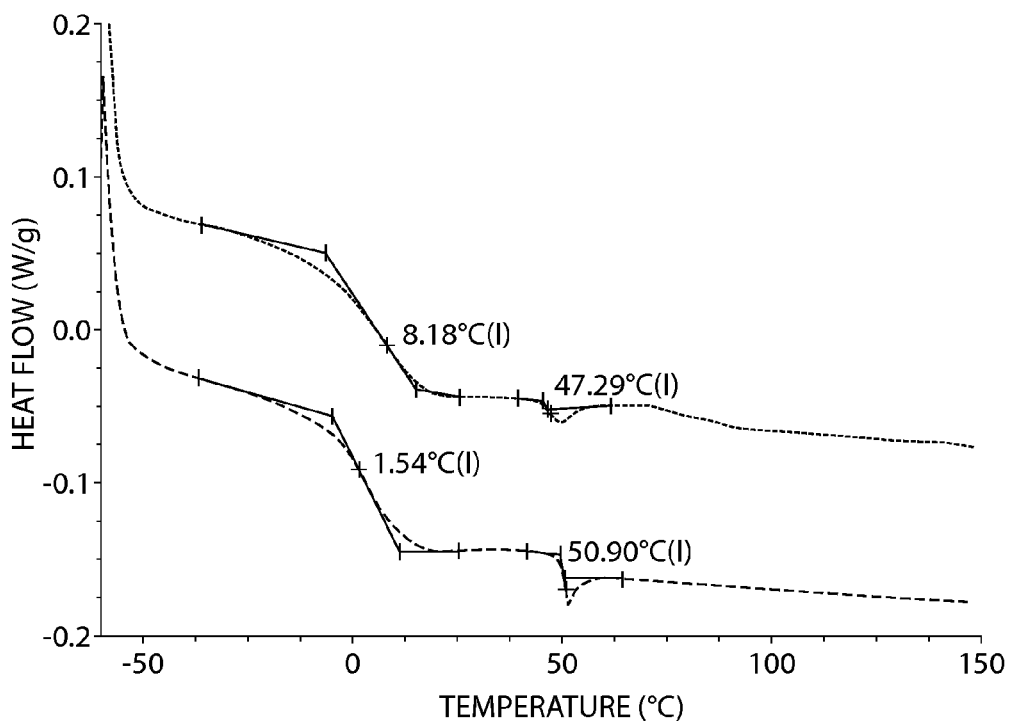
FIG. 3 is a DSC curve of poly(D,L-lactide)-block-poly (ethylene glycol) (PLA-PEG, Mn PLA block=16 kDa; Mn PEG block=5 kDa) when recovered from a melt polymerization and having been cooled at an unknown cooling rate.

FIG. 3 shows the DSC curve of poly(D,L-lactide)-block-poly(ethylene glycol) (PLA-PEG, Mn PLA block=16 kDa; Mn PEG block=5 kDa) when recovered from a melt polymerization and having been cooled at an unknown cooling rate. The DSC measurement was repeated. The top curve is the first heat, and the bottom curve is the second heat. Two distinct transitions are observed in the DSC curve of PLA-PEG (16 kDa-5 kDa) block copolymer. The transition between 1 and 10° C. is a $T_g$ of the mixed PEG and PLA phases, while the transition between 40 and 50° C. is a melting peak of a PEG rich phase. Homopolymer PEG of similar molar masses typically exhibit $T_g$'s between −50 and −25° C., while PLA homopolymer of similar molar mass exhibits a $T_g$ in the 30-50° C. range. The observed $T_g$ lies between that expected for a pure PEG homopolymer and a pure PLA homopolymer indicating that this copolymer sample is comprised of a mixed phase containing both PEG and PLA.

Figure 4A:
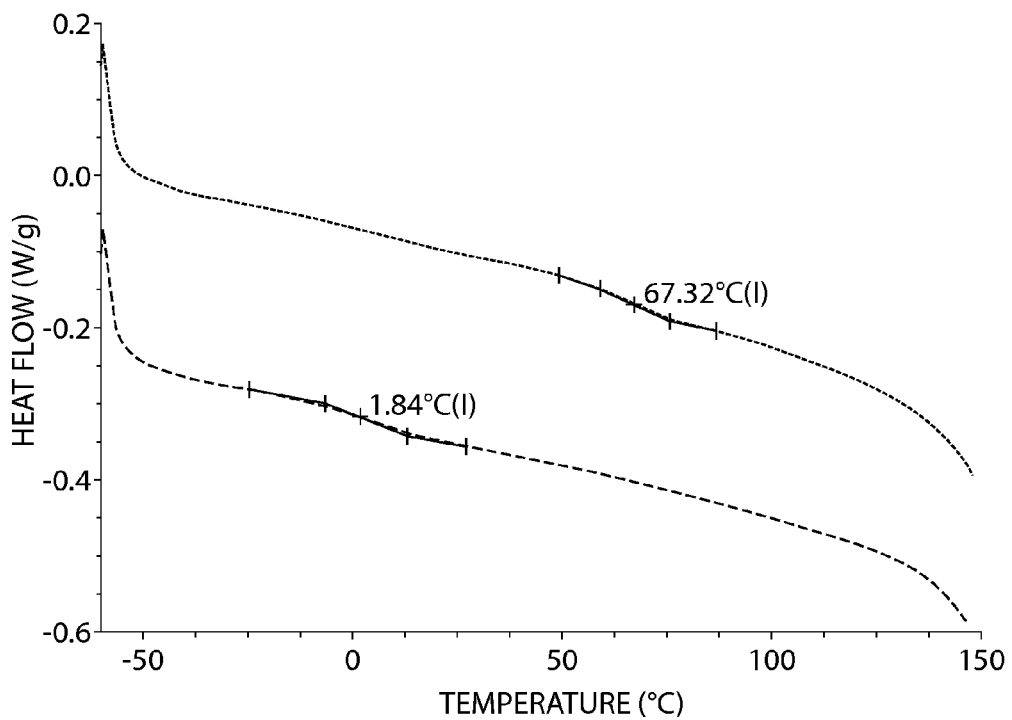
FIG. 4A is a DSC curve of poly(D,L-lactide)-block-poly (ethylene glycol) (PLA-PEG, Mn PLA block=16 kDa; Mn PEG block=5 kDa) when recovered from a precipitation of polymer solution (100 mg/mL in dichloromethane) into a binary non-solvent mixture (diethyl ether/hexane=70/30 (v/v)

FIG. 4A shows the DSC curve of poly(D,L-lactide)-block-poly(ethylene glycol) (PLA-PEG, Mn PLA block=16 kDa; Mn PEG block=5 kDa) when recovered from a precipitation of polymer solution (100 mg/mL in dichloromethane) into a binary non-solvent mixture (diethyl ether/hexane=70/30 (v/v). The DSC measurement was repeated. The top curve is the first heat, and the bottom curve is the second heat. The block copolymer exhibits a $T_m$ between 60 and 70° C. in the first heat indicating presence of a crystalline PEG polymer phase. After cooling, the resulting polymer melts at a rate of 10° C. per minute, the second heating curve exhibits a low temperature $T_g$ indicating a single PEG and PLA mixed phase similar to that observed in FIG. 3 for PLA-PEG block copolymer recovered from a polymer melt.

Results shown in FIGS. 3 and 4A suggest that the number and type of glass transitions observed in block copolymer systems, as well as the values of the observed $T_g$, vary widely depending upon the sample's history. The experimental route to the polymer sample (melt versus precipitation) alters its phase behavior, thereby leading to distinct glass transition behavior. The thermal history (such as cooling rate after a melt cycle) also significantly alters phase structure and thermal behavior.

Figure 4B:
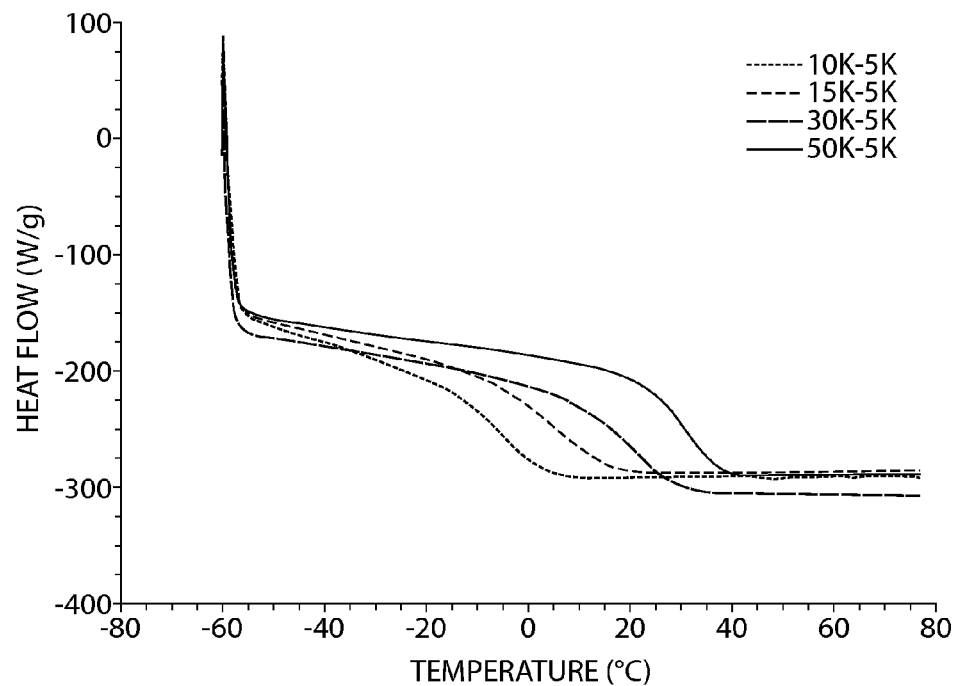
FIG. 4B are DSC curves showing glass transitions observed in PLA-PEG block copolymers of increasing molecular weights. PLA block number average molecular weight, Mn=10 KDa (lower curve), 15 KDa, 30 KDa and 50 KDa.
Figure 4C:
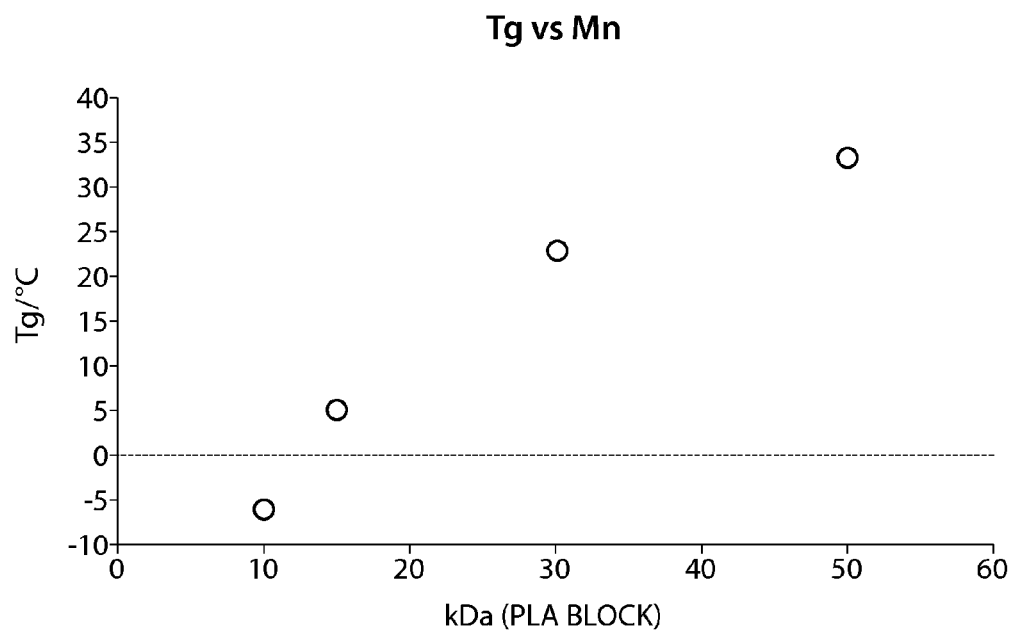
FIG. 4C shows the dependence of Tg on the molecular weight ($M_n$) of PLA in PLA-PEG block copolymers.

FIG. 4B shows the DSC curves of four PLA-PEG copolymers wherein the PEG block consists of number average molecular weight of 5 KDa and the PLA block number average molecular weight is 10, 15, 30 and 50 KDa, respectively. As observed above, heating a polymer sample above its $T_g$ (and/or $T_m$ if applicable) erases the effects of thermal history and allows direct comparison of samples that now have a similar thermal history (i.e. have been cooled from a melt at a fixed cooling rate e.g., 10° C./minute). Thus, only second heat data for each system is shown in FIG. 4B and the position of the inflection point ($T_g$ value) of the mixed PLA and PEG phases increase from −6° C. to 33° C. as PLA number average molecular weight increase from 10 to 50 KDa. FIG. 4C shows the trend observed within the molecular weight range tested and indicates a strong dependence of $T_g$ on polymer molecular weight.

Figure 5:
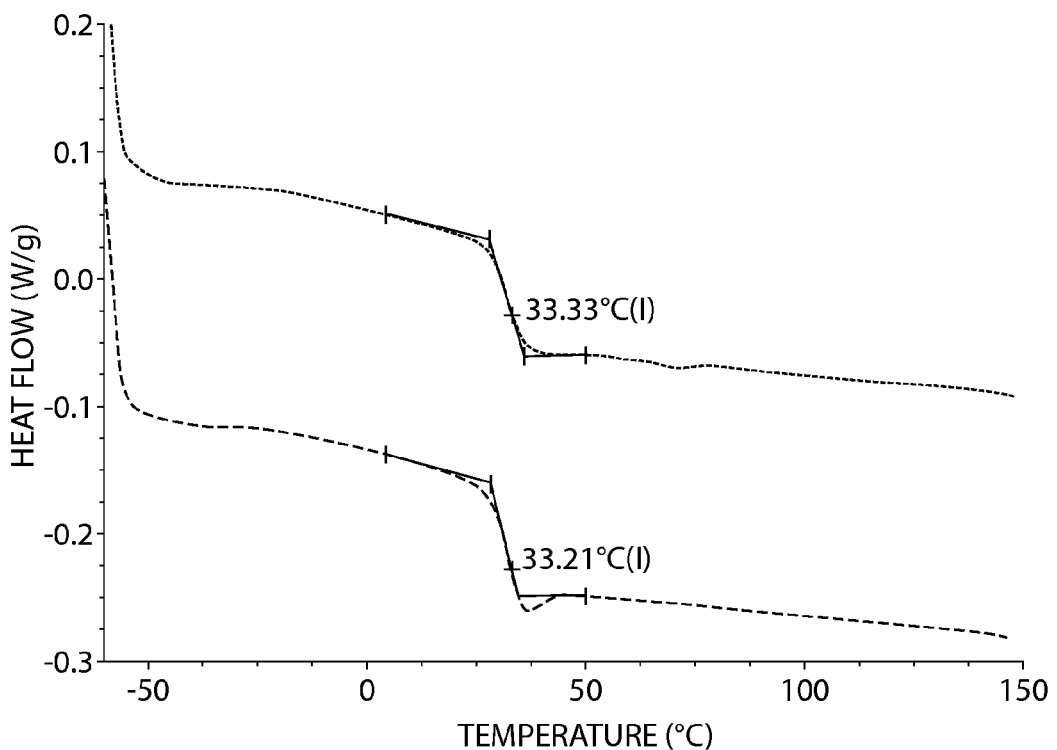
FIG. 5 is a DSC curve of poly(D,L-lactide) (PLA, Mn=6 kDa) when recovered from a precipitation process.

FIG. 5 shows the DSC curve of poly(D,L-lactide) (PLA, Mn=6 kDa) when recovered from a precipitation process. The DSC measurement was repeated. The top curve is the first heat, and the bottom curve is the second heat. FIG. 5 shows a glass transition between 30 and 35° C. in both first and second heat cycles. As expected for homopolymers, no difference in the $T_g$ is observed despite the different routes (precipitation versus melt) to the polymer sample since no phase separation is possible.

Figure 6A:
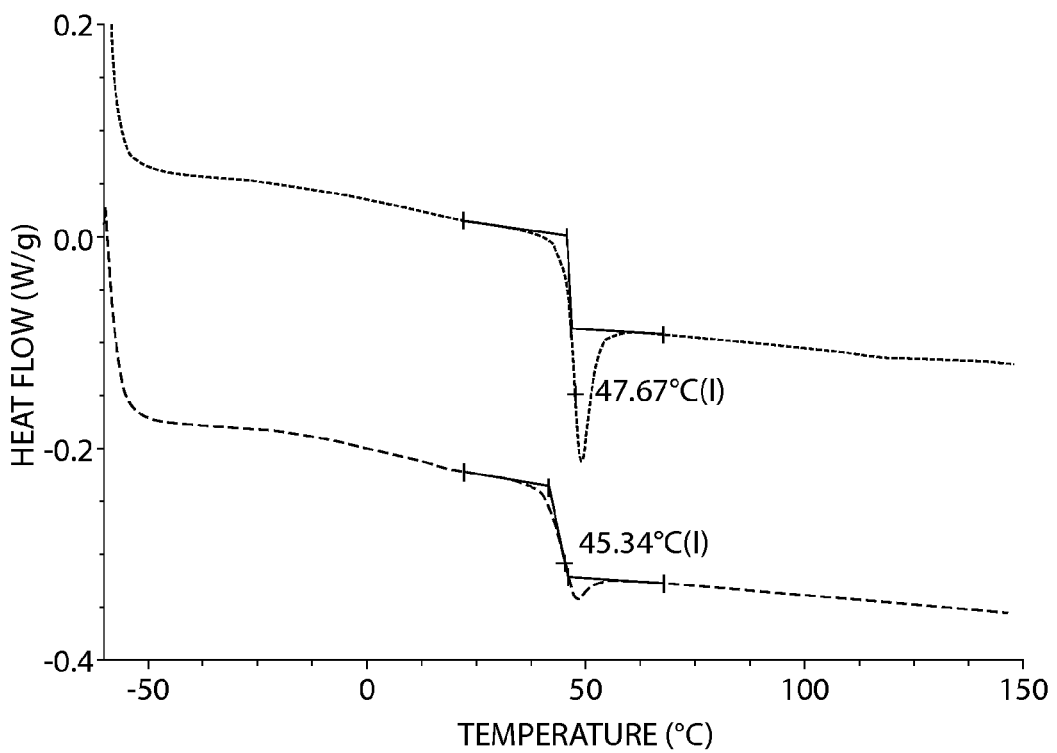
FIG. 6A depicts a DSC curve of poly(D,L-lactide) (PLA, Mn=75 kDa) when recovered from a precipitation process.

FIG. 6A shows the glass transition between 45 and 50° C. observed in poly(D,L-lactide) (PLA, Mn=75 kDa). The DSC measurement was repeated. The top curve is the first heat, and the bottom curve is the second heat. The higher $T_g$ value of this PLA sample, relative to the lower molar mass PLA shown in FIG. 5, indicates the expected increase in $T_g$ with increasing polymer molecular weight. The first heat cycle in FIG. 6A shows an endothermic hysteresis peak on the high temperature side of the glass transition indicating that this polymer sample was annealed below its $T_g$ or cooled (from a melt) at a rate slower than 10° C. per minute (the heating rate used in this heat cycle)

Figure 6B:
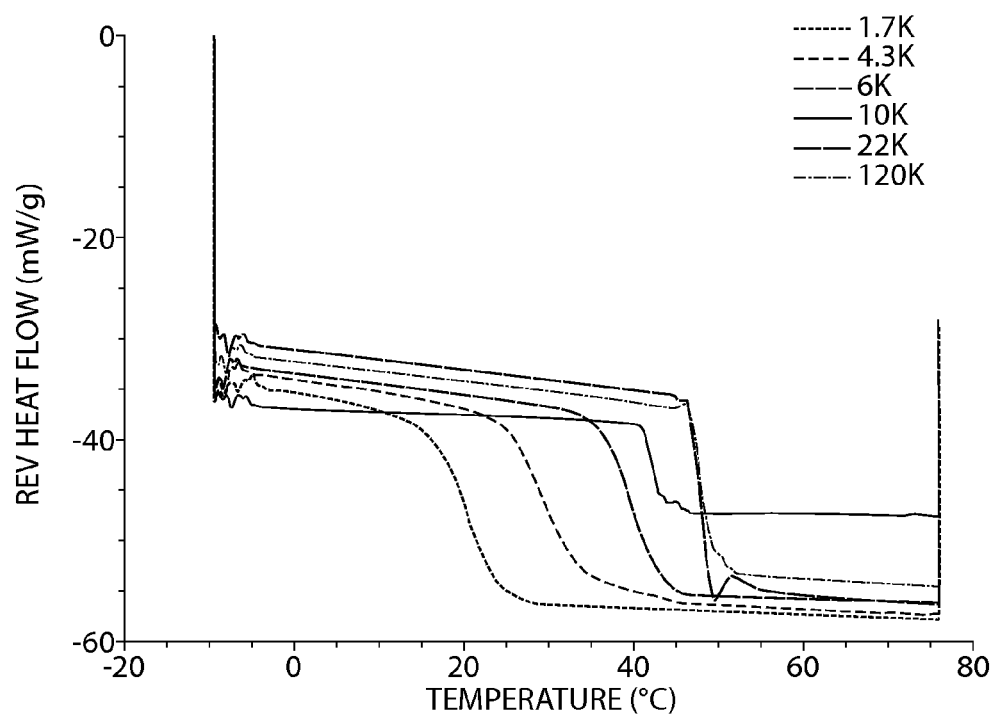
FIG. 6B depicts modulated DSC curves showing the glass transition temperatures in homopolymer poly(D,L-lactide) of number average molecular weights ($M_n$) 1.7 KDa (lower), 4.3 KDa, 6 KDa, 10 KDa, 22 KDa, and 120 KDa.
Figure 6C:
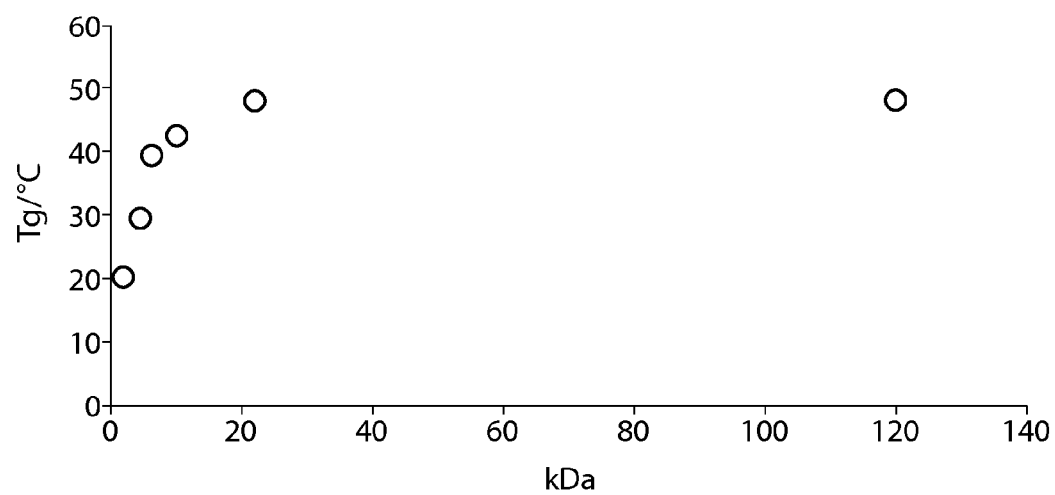
FIG. 6C shows the dependence of Tg on the number average molecular weight ($M_n$) of PLA homopolymers

Accurate determination of $T_g$ values is difficult when enthalpic relaxation events occur close to glass transition temperature as observed for the 75 KDa PLA sample shown in FIG. 6A. FIG. 6B shows the reversing heat component of the total heat flow measured in modulated DSC experiments for several PLA homopolymers. The number average molecular weights of the PLA samples analyzed range between 2K and 120 KDa. The data indicates that the $T_g$ values increase with molecular weight in the 2 KDa to 22 KDa molecular weight range and then plateau upon further increase in molecular weight as shown in FIG. 6C.

Example 4

Emulsion Preparation of Drug-Containing Nanoparticles

A general emulsion procedure for the preparation of drug loaded nanoparticles in aqueous suspension (in 30 wt. % sucrose, 3-6 wt. % polymeric nanoparticles containing about 10 wt. % drug with respect to particle weight) is summarized as follows. An organic phase is formed composed of 30% solids (wt %) including 24% polymer and 6% docetaxel (DTXL). The organic solvents are ethyl acetate (EA) and benzyl alcohol (BA), where BA comprises 21% (wt %) of the organic phase. The organic phase is mixed with an aqueous phase at approximately a 1:2 ratio (oil phase:aqueous phase) where the aqueous phase is composed of 0.5% sodium cholate, 2% BA, and 4% EA (wt %) in water. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to a chilled quench (0-5° C.) of deionized water under mixing. The quench:emulsion ratio is approximately 10:1. Then, a solution of 35% (wt %) of Tween-80 is added to the quench to achieve approximately 4% Tween-80 overall. The nanoparticles are then isolated and concentrated through ultrafiltration/diafiltration.

In an exemplary procedure to make fast-releasing nanoparticles with suppressed $T_g$, 50% of the polymer is polylactide-poly(ethylene glycol) diblock copolymer (PLA-PEG; 16 kDa-5 kDa) while 50% of the polymer is poly(D,L-lactide) (PLA; 6.5 kDa Mn). The resulting nanoparticles have an onset of the glass transition below 37° C., and thus a relatively rapid diffusional-based release at physiological temperature.

In an exemplary procedure to make normal-releasing nanoparticles with augmented $T_g$, 100% of the polymer is polylactide-poly(ethylene glycol) diblock copolymer (PLA-PEG; 16 kDa-5 kDa). The resulting nanoparticles have an onset of $T_g$ at about 37° C.

In an exemplary procedure to make slow-releasing nanoparticles with augmented $T_g$, 50% of the polymer is polylactide-poly(ethylene glycol) diblock copolymer (PLA-PEG; 16 kDa-5 kDa) while 50% of the polymer is poly(D,L-lactide) (PLA; 75 kDa). The resulting nanoparticles have an onset of $T_g$ above 37° C., and thus a relatively slow diffusional-based release at physiological temperature.

Example 5

Methods for Determining Nanoparticle Size and Drug Content

Particle size was analyzed by two techniques—dynamic light scattering (DLS) and laser diffraction (LD). DLS was performed using a Brookhaven ZetaPals instrument at 25° C. in dilute aqueous suspension using a 660 nm laser scattered at 90° and analyzed using the Cumulants (typical) and NNLS methods. Laser diffraction was performed with a Horiba LS950 instrument in dilute aqueous suspension using both a HeNe laser at 633 nm and an LED at 405 nm, scattered at 90°, or an Accusizer SPOS, and analyzed using the Mie optical model.

Drug load was calculated by dividing the docetaxel content of the nanoparticle slurry by the overall solid content of the slurry. Docetaxel content was determined by extracting the drug from the nanoparticles using acetonitrile and analyzing samples on a C8 reverse phase column (Waters X-Bridge C8) using a gradient from 20% acetonitrile (0.016% TFA) to 100% acetonitrile (0.016% TFA). The eluent absorbance was monitored at 230 nm. Docetaxel eluted with about 40% acetonitrile. The gradient was increased to 100% acetonitrile to elude the hydrophobic nanoparticle polymeric components, PLA-PEG and PLA-PEG-GL2. The quantitation limit of docetaxel is around 0.5 μg/mL. The solid content of the slurry is determined gravimetrically by removing water from the suspension using vacuum and heat.

The particle size and drug loading of the slow, normal, and fast releasing batches described in Example 4 is summarized in Table 5 below:

TABLE 5

Nanoparticle size and drug content of docetaxel loaded nanoparticles

| Description | Diameter via DLS | Median via LD | Drug load |
|---|---|---|---|
| "Fast" Release | 120.1 nm | Not determined | 9.7% |
| "Normal" Release | 103.2 nm | 77.6 nm | 9.6% |
| "Slow" Release | 99.7 nm | 73.8 nm | 8.0% |

Example 6

Determination of $T_g$ for Nanoparticles in Aqueous Suspension

The glass transition temperature ($T_g$) of nanoparticles in aqueous suspension was determined using heat flux DSC. The samples were heated between 4° C. and 70° C. at a constant heating rate of either 10° C. per minute or 20° C. per minute. Due to the relatively high vapor pressure of water in most of this temperature range, the analysis was conducted in hermetically sealed pans to prevent leakage of water vapor.

FIGS. 8 through 11 show the DSC curves of nanoparticle samples in an aqueous suspension. The nanoparticle samples analyzed were typically stored frozen at −20° C. The stored samples were first thawed by placing them into an ambient temperature water bath and subsequently concentrating them using an ultracentrifugation method. About 4 mL of nanoparticle suspension (30-50 mg/mL nanoparticles) was placed into a Millipore Amicon centrifugal filtration device having polypropylene housing and a regenerated cellulose membrane filter with a 100 kDa molecular weight cut-off limit. The sample was concentrated by centrifugation at 4000×g for 1 hour to reduce the retentate volume three to four fold. The retentate (now about 120-150 mg/mL nanoparticles) was transferred to a glass scintillation vial and frozen by placing into a −20° C. freezer. This thermal treatment was identical to that used after nanoparticle fabrication and involved temperatures below the glass transition temperature of the nanoparticles. Thus, this treatment did not alter the thermal history of the particles relative to their condition following the nanoparticle fabrication process.

Figure 7:
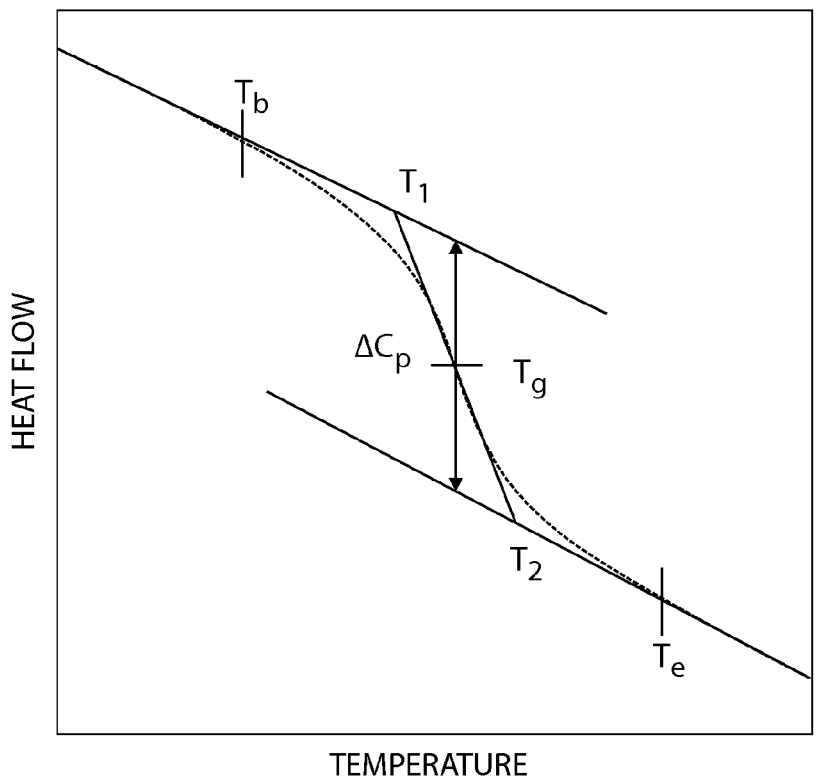
FIG. 7 is an illustration of the five points used to define the endothermic transitions observed in the DSC analysis of nanoparticles.

The endothermic transitions shown in FIGS. 8 through 11 were defined by selection of five points to identify the glass transition temperature as shown in FIG. 7. These include a $T_b$, the beginning of the deviation of the DSC curve from linearity; $T_1$, the extrapolated onset temperature of the glass transition; $T_2$, the extrapolated end temperature of the glass transition; and $T_e$, the end temperature of the glass transition. The glass transition temperature is defined in one of two possible ways: as the temperature at half height of the increase in heat capacity (½ $\Delta C_p$) (as shown in FIG. 7) or as the point of inflexion.

Figure 8:
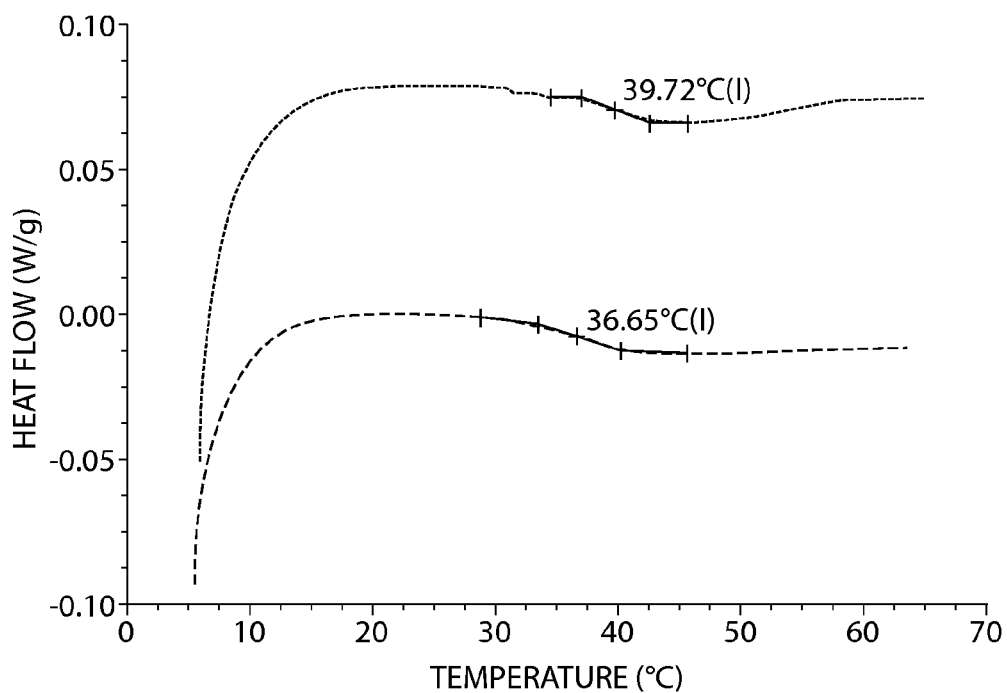
FIG. 8 is a DSC curve showing the endothermic glass transition observed in nanoparticles composed of a mixture of PLA-PEG (Mn PLA block=16 kDa; Mn PEG block=5 kDa) and low molecular weight PLA homopolymer (Mn=6.5 kDa).

The DSC curves in FIG. 8 show the endothermic transition exhibited by a nanoparticle suspension wherein the particles are made from a 50/50 (by weight) mixture of PLA-PEG (16 kDa-5 kDa) copolymer and low molecular weight PLA homopolymer (Mn=6.5 kDa) when heated between 4° C. and 70° C. at a heating rate of 10° C. per minute. The nanoparticle sample analyzed contained about 10 wt % encapsulated docetaxel. Analysis was performed using a TA Instrument Q200 Heat Flux DSC. The DSC measurement was repeated. The $T_b$ and $T_g$ values observed are at 37° C. and 39.7° C., respectively for the first heat cycle (top curve). The sample was subsequently cooled at rate of 10° C. per minute to 4° C. and heated again to 70° C. (at a 10° C. per minute heating rate) in a second heat cycle. The bottom curve of FIG. 8 shows the endothermic transition observed in the second heat cycle. The $T_b$ and $T_g$ values now shift to 33° C. and 36.7° C., respectively. In use for intravenous injection, nanoparticles would only be exposed to physiological temperature. Thus, only the data in the first heat cycle is of relevance when predicting their drug release behavior.

Figure 9:
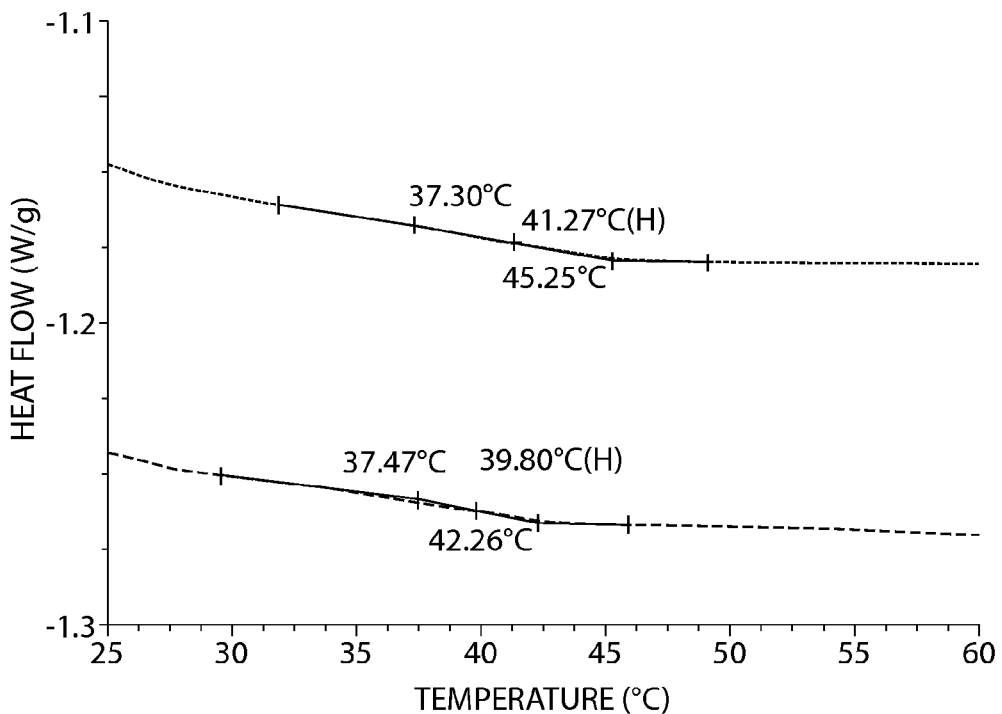
FIG. 9 is a DSC curve showing the endothermic glass transition observed in nanoparticles composed of PLA-PEG (Mn PLA block=16 kDa; Mn PEG block=5 kDa) as the only polymeric component of the particle.

The DSC curves in FIG. 9 show the endothermic transition exhibited by a nanoparticle suspension where the particles are made from PLA-PEG (16 kDa-5 kDa) copolymer as the only polymeric component in the formulation. The suspension was heated between 4° C. and 70° C. at a heating rate of 20° C. per minute. The nanoparticle sample analyzed contained about 10 wt % encapsulated docetaxel. Analysis was performed using a TA Instrument Q2000 Heat Flux DSC. The DSC measurement was repeated. The $T_b$ and $T_g$ values observed are at 37.3° C. and 41.3° C., respectively, for the first heat cycle shown as the top curve in FIG. 9. The bottom curve shows a duplicate run of a fresh sample of nanoparticle suspension, and resulted in $T_b$ and $T_g$ values of 37.5° C. and 39.8° C., respectively.

Figure 10:
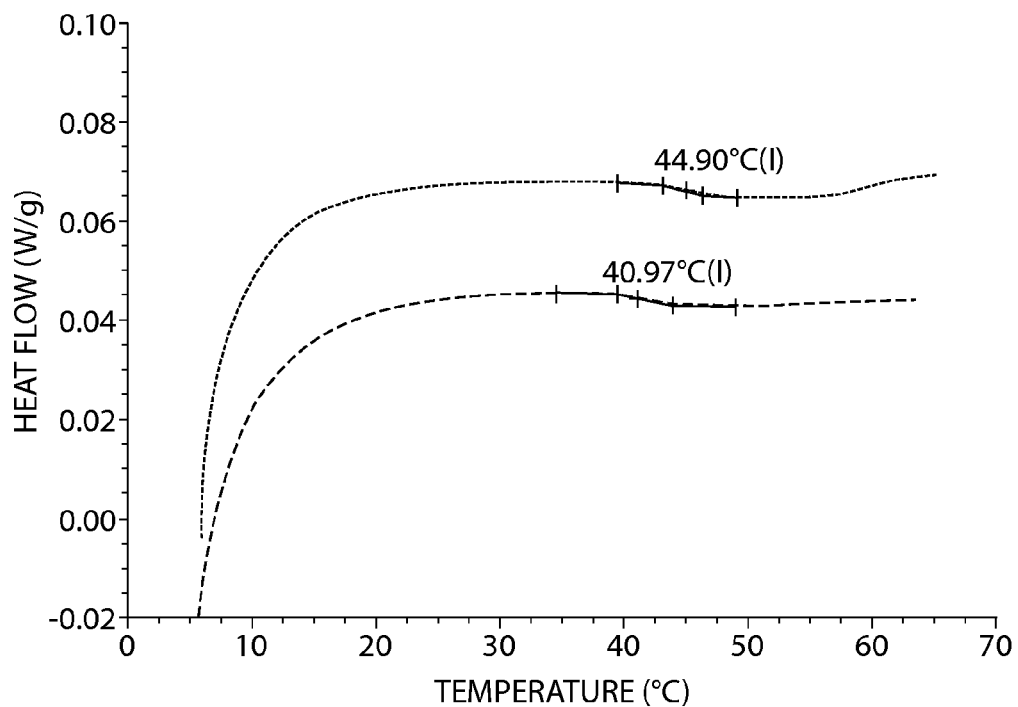
FIG. 10 is a DSC curve showing the endothermic glass transition observed in nanoparticles composed of a mixture of PLA-PEG (Mn PLA block=16 kDa; $M_n$ PEG block=5 kDa) and high molecular weight PLA homopolymer ($M_n$=75 kDa).

The DSC curves in FIG. 10 show the endothermic transition exhibited by a nanoparticle suspension wherein the particles are made from a 50/50 (by weight) mixture of PLA-PEG (16 kDa-5 kDa) copolymer and high molecular weight PLA homopolymer (Mn=75 kDa) when heated between 4° C. and 70° C. at a heating rate of 10° C. per minute. The nanoparticle sample analyzed contained about 10 wt % encapsulated docetaxel. Analysis was performed using a TA Instrument Q200 Heat Flux DSC. The DSC measurement was repeated. The $T_b$ and $T_g$ values observed are at 43° C. and 44.9° C., respectively, for the first heat cycle (top curve). The sample was subsequently cooled at rate of 10° C. per minute to 4° C. and heated again to 70° C. (at a 10° C. per minute heating rate) in a second heat cycle. The bottom curve shown in FIG. 10 shows the endothermic transition observed in the second heat cycle. The $T_b$ and $T_g$ values shifted to 39° C. and 41° C., respectively.

Figure 11A:
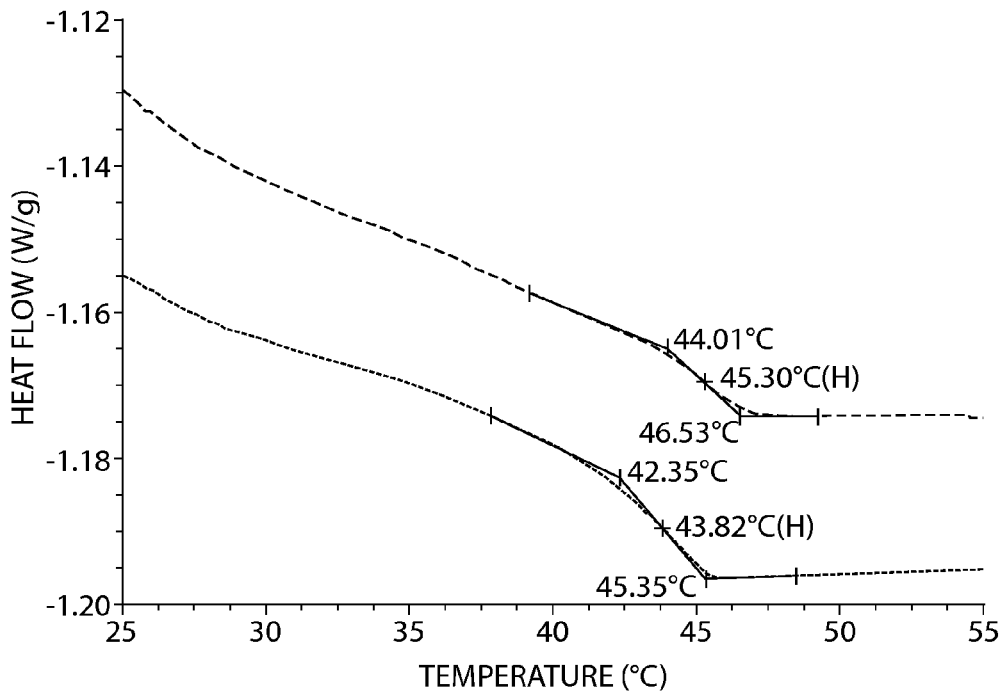
FIG. 11A shows a DSC curve showing the endothermic glass transition observed in nanoparticles composed of a mixture of PLA-PEG (16 kDa-5 kDa) and high molecular weight PLA homopolymer ($M_n$=75 kDa).

The DSC curves in FIG. 11A show the endothermic transition exhibited by a nanoparticle suspension wherein the particles are made from a 50/50 (by weight) mixture of PLA-PEG (16 kDa-5 kDa) copolymer and high molecular weight PLA homopolymer (Mn=75 kDa) when heated between 4° C. and 70° C. at a heating rate of 20° C. per minute. The nanoparticle sample analyzed contained about 10 wt % encapsulated docetaxel. Analysis was performed using a TA Instrument Q2000 Heat Flux DSC. The DSC measurement was repeated. The $T_b$ and $T_g$ values observed are at 44° C. and 45.3° C., respectively, for the first heat cycle. The bottom curve shows a duplicate run of a fresh sample of nanoparticle suspension, and gave $T_b$ and $T_g$ values of 42.4° C. and 43.8° C., respectively.

Table 6A summarizes the endothermic transitions observed in the DSC studies on the nanoparticles described above.

TABLE 6A

Summary of Endothermic Transitions Observed in the First Heat Cycle of Nanoparticle Suspensions

| Figure | Description | Instrument used and mode | Heating rate ° C./min. | $T_b$ (° C.) | $T_g$ (° C.) | $T_e$ (° C.) |
|---|---|---|---|---|---|---|
| FIG. 8 | PLA-PEG and 6.5 kDa PLA | TA Q200-T4 | 10 | 35* | 39.7 | 42.5 |

TABLE 6A-continued

Summary of Endothermic Transitions Observed in the First Heat Cycle of Nanoparticle Suspensions

| Figure | Description | Instrument used and mode | Heating rate °C./min. | $T_b$ (°C.) | $T_g$ (°C.) | $T_e$ (°C.) |
|---|---|---|---|---|---|---|
| FIG. 9 | PLA-PEG only | TA Q2000-T4P | 20 | 37.3 | 41.3 | 45.3 |
| FIG. 10 | PLA-PEG and 75 kDa PLA | TA Q200-T4 | 10 | 43 | 44.9 | 46.3 |
| FIG. 11 | PLA-PEG and 75 kDa PLA | TAQ2000-T4P | 20 | 44 | 45.3 | 46.5 |

*In all cases, the $T_b$, $T_g$ and $T_e$ values correspond to the cross-bars on the DSC curves with the exception of FIG. 8, where the baseline deviation begins at 32° C.. Due to another step seen at about 34° C., the cross-bars do not reflect the $T_b$ value accurately. Thus, a $T_b$ value of 35° C. was assigned to account for the deviation.

To confirm the glass transition temperatures of docetaxel containing nanoparticles, a different batch of particles of the same composition as those shown in FIGS. 8 through 11 (and Table 6A) were tested using modulated DSC (MDSC). The nanoparticle sample preparation methods used were described above to those describe above. The modulated DSC experiment was conduced using a sinusoidal temperature oscillation of amplitude 0.5° C. and period of 60 seconds superimposed on a 2° C./minute linear ramp rate. FIG. 11B shows the reversing heat flow component of the total heat flow. These Nanoparticle batches also showed a similar dependence of nanoparticle glass transition temperature on the nanoparticle composition as that seen in FIGS. 8 through 11.

Figure 11B:
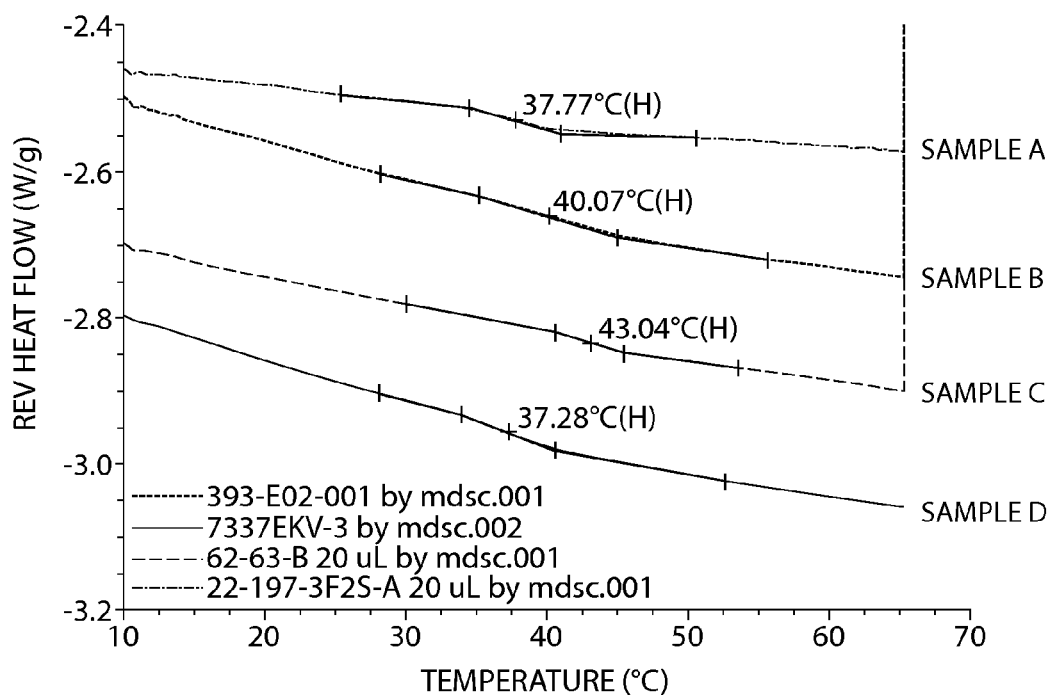
FIG. 11B shows DSC curves for a series of nanoparticles showing the reversing heat flow component of the total heat flow.

In FIG. 11B, the top M-DSC curve shows a $T_g$ at 37.8° C. exhibited by nanoparticles (Sample A) wherein the particles are made from a 50/50 (by weight) mixture of PLA-PEG (16 kDa-5 kDa) copolymer and low molecular weight PLA homopolymer (Mn=6.5 kDa) and contain about 10 wt. % encapsulated docetaxel. The second M-DSC curve shows a $T_g$ at 40.1° C. exhibited by nanoparticles (Sample B) where the particles are made from PLA-PEG (16 kDa-5 kDa) copolymer as the only polymeric component in the formulation and contain about 10 wt. % encapsulated docetaxel. The third M-DSC curve shows a $T_g$ at 43.0° C. exhibited by nanoparticles (Sample C) where wherein the particles are made from a 50/50 (by weight) mixture of PLA-PEG (16 kDa-5 kDa) copolymer and high molecular weight PLA homopolymer (Mn=75 kDa) and contain about 10 wt. % encapsulated docetaxel. The bottom M-DSC curve shows a $T_g$ at 37.3° C. exhibited by nanoparticles (Sample D) where the particles are made from PLA-PEG (16 kDa-5 kDa) copolymer as the only polymeric component and contain no encapsulated docetaxel.

Table 6B summarizes the endothermic glass transitions observed in the Modulated DSC study of the nanoparticles described above.

TABLE 6B

Summary of Glass Transitions observed in Modulated DSC analysis of nanoparticle suspensions

| FIG. | Description | Encapsulated drug | Instrument used and mode | $T_g$ (°C.) |
|---|---|---|---|---|
| FIG. 11B Sample A | PLA-PEG and 6.5 kDa PLA | Docetaxel | TA Q2000-T4P | 37.8 |
| FIG. 11B Sample B | PLA-PEG only | Docetaxel | TA Q2000-T4P | 40.1 |
| FIG. 11B | PLA-PEG and | Docetaxel | TA Q2000-T4P | 43.0 |
| Sample C FIG. 11C Sample D | 75 kDa PLA PLA-PEG and 75 kDa PLA | None | TAQ2000-T4P | 37.3 |

Example 7

Rate of Drug Release from Nanoparticle Samples

The rate of drug released from nanoparticles was determined in vitro under sink conditions with respect to drug (docetaxel) solubility in water. The experiment was conducted at physiological pH and ionic strength using a phosphate buffer saline (PBS) solution containing hydroxypropyl-β-cyclodextrin (HP-βCD) as a drug solubilizer as the release medium.

Docetaxel loaded nanoparticle samples containing about 5 mg/mL drug were first diluted with deionized water to a final concentration of 250 μg/mL (in docetaxel). For example, a batch containing 1 ml of 5 mg/mL DTXL was diluted with 19 mL of cold DI-water to give a total of 20 mL nanoparticle suspension containing 250 μg/mL drug.

The release medium (2.5% HP-βCD in PBS (w/w)) was prepared by dissolving PBS (Sigma PBS P-5368) into deionized water to obtain a phosphate buffer solution containing 0.01 M phosphate buffered saline (NaCl: 0.138 M; KCl: 0.0027 M). Hydroxypropyl βCD (Trapsol), 100 g, was dissolved into 3900 g of PBS solution to obtain 2.5% HP-βCD in PBS. 120 ml, of this release medium was transferred into Qorpak wide mouth bottles (16194-290 VWR #, 7983 Qorpak #) using a graduated cylinder.

The nanoparticle slurry (3 mL) was added to 120 mL release medium in the Qorpak bottle. The bottle was capped and mixed by swirling by hand. Time zero (T=0) control samples were withdrawn. The first non centrifuged samples were obtained by withdrawing 900 μL of sample immediately after the nanoparticle slurry was mixed with the release medium and transferring it to a HPLC vial containing an equal volume (900 μL) of acetonitrile. A centrifuged sample (second sample), that underwent centrifugation treatment analogous to that received by samples drawn at later time points, was obtained by withdrawing a 4 mL sample from the Qorpak bottle and transferring it to a centrifuge tube (Beckman coulter, Capacity 4 mL, #355645). The sample was subsequently centrifuged at 50,000 rpm (236,000 g) for 1 hour at 4° C. on an Ultracentrifuge Optima MAX-XP (P/N 393552AB, TZO8H04, Cat #393315) using a fixed angle rotor MLA 55 (S/N 08U411). 900 μL of supernatant from the upper part of the centrifuged samples was withdrawn without causing turbulence to avoid re-suspending the nanoparticle pellet at the centrifuge tube bottom. This 900 μL aliquot was transferred to 900 μL of acetonitrile in an HPLC vial. Docetaxel found in the supernatant represents the amount of drug released, since any drug still encapsulated within the nanoparticles was pelletized (with the nanoparticles) upon centrifugation.

The release samples in the Qorpac bottles were continually stirred at 75 rpm using a waterbath shaker held at 37° C. to maintain continuous mixing conditions. 4 mL samples are drawn at pre-determined time points and treated as described above to obtain HPLC samples for analysis of docetaxel content. Samples were typically drawn at 0, 1, 2, 4, and 24 hours, and the time points were modified as necessary to account for significantly faster or slower releasing batches.

Figure 12:
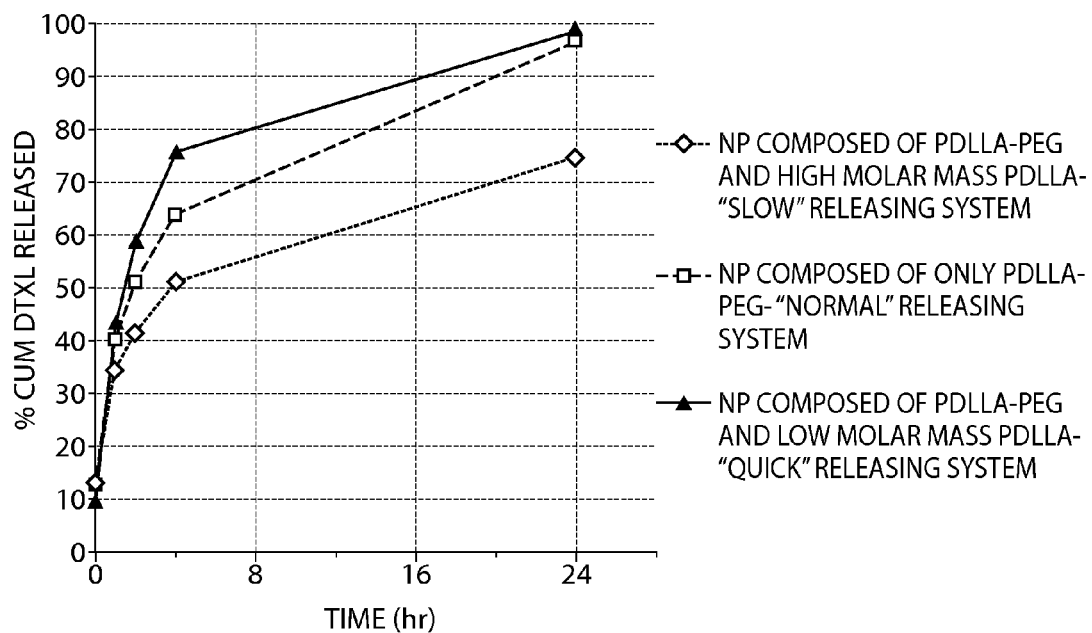
FIG. 12 is a comparison of docetaxel (DTXL) release rates from nanoparticles based on different polymeric components as detailed in the plot legend.

FIG. 12 shows the rate of docetaxel released (as percent total encapsulated docetaxel) at 37±0.5° C. from nanoparticles comprised of different polymeric materials. The solid line (top) corresponds to drug release rate from a "quick" releasing system composed of a 1:1 (w/w) mixture of PLA-PEG (16 kDa-5 kDa) and low molecular weight (Mn=6.5 kDa) PLA homopolymer. The dashed line (middle) corresponds to the drug release rate from a "normal or intermediate" releasing system composed of only PLA-PEG (16 kDa-5 kDa). The dotted line (bottom) corresponds to drug release rate from a "slow" releasing system composed of a 1:1 (w/w) mixture of PLA-PEG (16 kDa-5 kDa) and high molecular weight (Mn=75 kDa) PLA homopolymer.

The rate of docetaxel released from the nanoparticles at 37° C. as shown in FIG. 12 indicates a strong dependence on the nanoparticle composition. Nanoparticles made from a mixture of PLA-PEG (16 kDa-5 kDa) and PLA ($M_n$=6.5 kDa) exhibited a "quick" release profile with about 75% of the encapsulated drug being released within the first 4 hours of being exposed to the release medium. In contrast, when the nanoparticles were made from only PLA-PEG (16 kDa-5 kDa), about 65% encapsulated drug was released over a similar period. This effect was further amplified when the nanoparticles were made from a mixture of PLA-PEG (16 kDa-5 kDa) and high molecular weight PLA ($M_n$=75 kDa). In this system, only about 50% of the drug was released in the first 4 hours.

As seen in Table 7A, the endothermic glass transitions observed in the three nanoparticle systems indicates that the temperature corresponding to the point at which the DSC curve begins to deviate from linearity ($T_b$) is a key parameter in determining the particles' drug release rate. In the "quick" releasing system, the endothermic transition begins at 35° C. The observed release behavior in this system indicates that the onset of segmental motion and consequent increase in the rate of drug diffusion within the nanoparticle core permits drug to reach the particle-water interface at a rate higher than that observed in systems where $T_b$>37° C. The "normal" releasing system exhibits a $T_b$=37.3° C., and the rate of drug release is correspondingly slower. The "slow" releasing system similarly exhibits an even higher $T_b$ (43° C.).

The significantly different rates of release observed when $T_b$ is below, at or above 37° C. is indicative of the strong effect of segmental motion on the rate of drug diffusion and release from the nanoparticle. The $T_g$ and $T_e$ values reported in Table 6 (glass transition temperature and point at which the DSC curve is linear again) also systematically increase between the "fast," "normal," and "slow" releasing systems. This increase is in agreement with the correlation between polymer segmental motion and drug release rates and confirms that the glass transition temperature of a given nanoparticle system under suspension conditions provides a means to predict the relative rate of drug release. The absolute rate of release additionally depends on other factors including the polymer-drug miscibility, drug solubility in water, drug molecular size, and drug phase structure (amorphous or crystalline) within the nanoparticle.

The reversing heat component of the total heat flow observed in MDSC experiments is free from artifacts resulting from enthalpic relaxations occurring close to the endothermic glass transition. As such, MDSC provides a more accurate determination of the $T_g$ value when compared to conventional DSC. MDSC analysis (data shown in Table 6B) illustrates that nanoparticles made from a mixture of PLA-PEG (16 kDa-5 kDa) and PLA ($M_n$=6.5 kDa) that exhibit a Tg at 37.8° C. also exhibit a "quick" release profile with about 75% of the encapsulated drug being released within the first 4 hours of being exposed to the release medium. This indicates that when nanoparticle glass transition temperatures are close to 37° C. (physiological temperature), high degree of segmental motion leads to relatively fast release of encapsulated drug. When the nanoparticles composed of PLA-PEG (16 kDa-5 kDa) only, about 65% encapsulated drug was released over a similar period of time. Lower degree of segmental motion in this higher $T_g$ (40.1° C.) sample results in correspondingly slower release of encapsulated drug. This trend continues in nanoparticles made from a mixture of PLA-PEG (16 kDa-5 kDa) and high molecular weight PLA ($M_n$=75 kDa), where a even higher $T_g$ (=43.0° C.) leads to a correspondingly slower release of encapsulated drug with only about 50% of the drug being released in the first 4 hours. Entry 4 (Table 6B) shows that the glass transition temperature of a polymeric nanoparticle composed of PLA-PEG (16 kDa-5 kDa) with no encapsulated drug. Comparison with a drug containing nanoparticle of similar polymer composition (entry 1, Table 6B) that contains encapsulated drug illustrates that docetaxel measureably impacts the glass transition temperature of a polymeric nanoparticle. In this case, about 10 wt. % encapsulated docetaxel increases the Tg value by 0.5° C. This body of data indicates that $T_g$ values of drug containing nanoparticles provide a means to accurately predict the corresponding drug release rates. Other measurements such as glass transition temperature of the polymeric components and/or their physical mixtures with drugs can provide general trends, for instance the effect of change in polymer molecular weight. However, such measurements fail to enable classification of a specific drug bearing nanoparticle as fast, moderate or slow releasing.

DSC data shown in FIGS. 3 through 7 for PLA-PEG recovered from a melt or precipitation and low ($M_n$=6.5 kDa) or high ($M_n$=75 kDa) molar mass PLA illustrates the strong dependence of the thermal behavior of these polymeric nanoparticle components on their thermal history as well as on the route of polymer processing prior to analysis. Thus, the glass transitions observed for polymeric components do not directly correlate to the thermal characteristics of nanoparticles. The process of nanoparticle fabrication imparts a specific thermal history to component polymers and additionally imparts specific morphological and phase characteristics to block copolymers such as PLA-PEG.

The thermal behavior of the polymer components affects the glass transition temperature in a predictable manner. For example, nanoparticles made from a 1:1 (w/w) mixture of low molecular weight PLA ($M_n$=6.5 kDa) and PLA-PEG (16 kDa-5 kDa) exhibit a lower $T_g$ than that exhibited by nanoparticles made from a similar mixture except with high molecular weight PLA (75 kDa). This result is based upon $T_g$ (75 kDa PLA) being greater than $T_g$ (6.5 kDa PLA) by about 20° C. The difference in $T_g$ permits selection of nanoparticle compositions to modulate the rate of drug release. However, the actual transition temperatures of nanoparticles made form such polymeric components cannot be predicted from $T_g$ values of polymeric components.

Example 8

Effect of Temperature on the Rate of Drug Release

To further test the role of nanoparticle glass transition temperature in the "fast," "normal," and "slow" releasing systems, the rates of drug release were tested at three temperatures other than 37° C. These temperatures included 32° C., i.e., 3-5° C. below the lowest onset temperature ($T_b$), and 52° C., a similar increment above the highest transition end temperature ($T_e$). In addition, the rate of release was determined at 25° C. to check the behavior at a temperature considerably below the $T_g$'s of all three nanoparticle systems.

Figure 13:
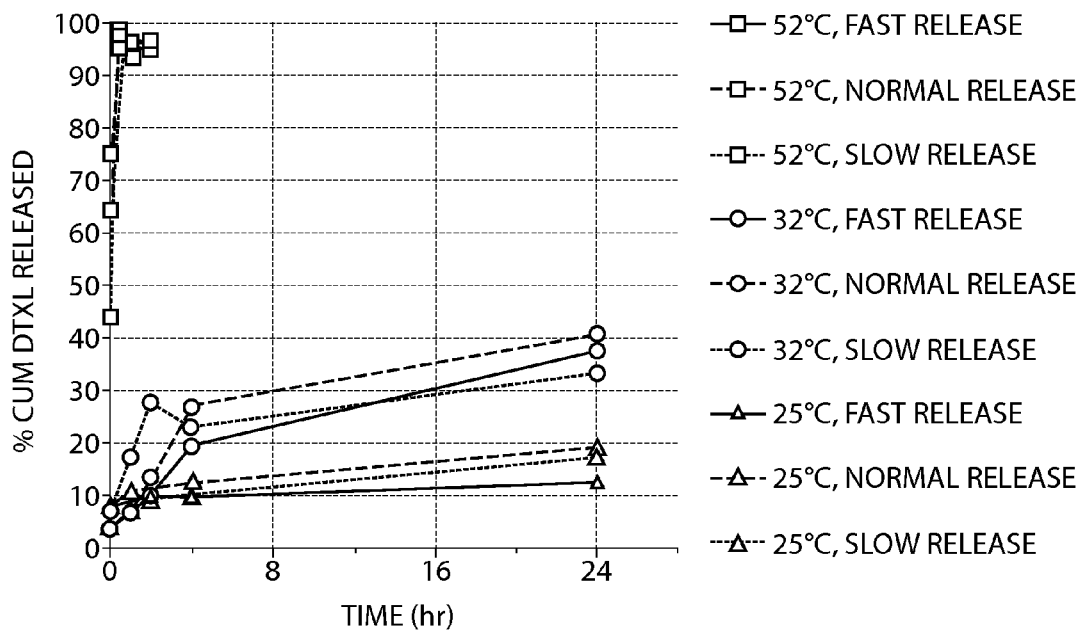
FIG. 13 is a graph showing the effect of temperature on drug release rates over 24 hours from nanoparticle systems that exhibit different glass transition temperatures.
Figure 14:
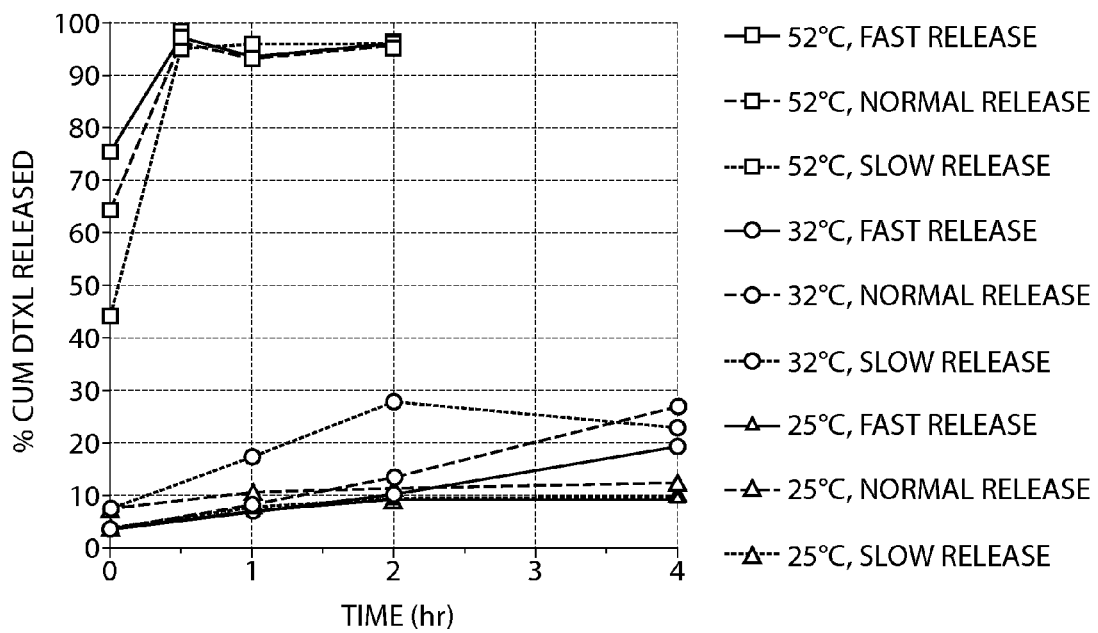
FIG. 14 is a graph showing an expansion of the 1-4 hour time period of the study given in FIG. 13.

The results are shown in FIG. 13, with an expansion of the 1-4 hour time period shown in FIG. 14. At 25° C., all three nanoparticle systems, despite their different onset of glass transition ($T_b$) temperatures, exhibited a similar rate of drug release (see data points shown as triangles in FIGS. 13 and 14). This observation confirms that at temperatures well below the $T_g$'s of all three systems, segmental motion is limited in all cases such that rates of drug transport and release are similar and relatively slow.

At 52° C., all three nanoparticle systems exhibit an accelerated rate of drug release confirming that at temperatures well above their glass transition temperatures, the nanoparticle cores are equally plastic (rubbery). Thus, drug diffusion rates are comparable and release rates become nearly identical with almost all drug being released within the first 30 minutes at 52° C. (see data shown as squares in FIGS. 13 and 14). The burst release observed for the three nanoparticle systems at 52° C. mirrors the trends observed at 37° C., with "slow", "normal" and "fast" systems releasing 45%, 65%, and 75% of their drug content immediately.

At 32° C., the release rates are similar but higher (for all systems) than those observed at 25° C. (see data shown as circles in FIGS. 13 and 14). These results suggest a temperature dependence of drug diffusion coefficient in the polymeric core and water solubility, with both parameters increasing at higher temperature and leading to the observed increase in drug release rates.

Example 9

Docetaxel Nanoparticles

Docetaxel nanoparticles comprising various PLA-PEG copolymers are prepared using the following formulation: 10% (w/w) theoretical drug and 90% (w/w) polymer-PEG (16-5, 30-5, 50-5, or 80-5 PLA-PEG). % total solids=20%. Solvents used are 21% benzyl alcohol and 79% ethyl acetate (w/w). For a 1 gram batch size, 100 mg of drug is mixed with 900 mg of polymer-PEG (16-5, 30-5, 50-5, or 80-5 PLA-PEG).

Docetaxel nanoparticles are produced as follows. In order to prepare a drug/polymer solution, appropriate amounts of docetaxel, and polymer are added to a glass vial along with appropriate amounts of ethyl acetate and benzyl alcohol. The mixture is vortexed until the drug and polymer are completely dissolved.

An aqueous solution is prepared. The aqueous phase for the 16-5 PLA-PEG formulation contains 0.5% sodium cholate, 2% benzyl alcohol, and 4% ethyl acetate in water. The 30-5 PLA-PEG formulation contains 5% sodium cholate, 2% benzyl alcohol, and 4% ethyl acetate in water, % total solids=20%. The aqueous phase for the 50-5 PLA-PEG formulation contains 5% sodium cholate, 2% benzyl alcohol, and 4% ethyl acetate in water, % total solids=20%. The aqueous phase for the 80-5 PLA-PEG formulation contains 5% sodium cholate, 2% benzyl alcohol, and 4% ethyl acetate in water, % total solids=20%. When higher molecular weight polymer-PEG is used (i.e. 30-5, 50-5, or 80-5 PLA-PEG), the concentration of sodium cholate surfactant in the water phase is increased from 0.5% to 5% in order to obtain nanoparticles with sizes similar to those particles comprising 16-5 PLA-PEG. Specifically, appropriate amounts of sodium cholate and DI water are added to a bottle and mixed using a stir plate until they are dissolved. Subsequently, appropriate amounts of benzyl alcohol and ethyl acetate are added to the sodium cholate/water mixture and mixed using a stir plate until all are dissolved.

An emulsion is formed by combining the organic phase into the aqueous solution at a ratio of 5:1 (aqueous phase:oil phase). The organic phase is poured into the aqueous solution and homogenized using hand homogenizer at room temperature to form a coarse emulsion. The solution is subsequently fed through a high pressure homogenizer (110S) to form a nanoemulsion.

The emulsion is quenched into cold DI water at <5° C. while stirring on a stir plate. The ratio of Quench to Emulsion is 8:1. Tween 80 in water is then added to the quenched emulsion at a ratio of 25:1 (Tween 80:drug).

The nanoparticles are concentrated through tangential flow filtration (TFF) followed by diafiltration to remove solvents, unencapsulated drug and Tween 80 (solubilizer). A quenched emulsion is initially concentrated through TFF using a 300 KDa Pall cassette (Two 0.1 m² membranes) to an approximately 100 mL volume. This is followed by diafiltration using approximately 20 diavolumes (2 L) of cold DI water. The volume is minimized before collecting, then 100 mL of cold water is added to the vessel and pumped through the membrane for rinsing. Approximately 100-180 mL of material in total are collected in a glass vial. The nanoparticles are further concentrated using a smaller TFF to a final volume of approximately 10-20 mL.

In order to determine the solids concentration of unfiltered final slurry, a volume of final slurry is added to a tared 20 mL scintillation vial and dried under vacuum on lyo/oven. Subsequently the weight of nanoparticles is determined in the volume of the dried down slurry. Concentrated sucrose (0.666 g sucrose/g total) is added to the final slurry sample to attain a final concentration of 10% sucrose.

In order to determine the solids concentration of a 0.45 µm filtered final slurry, a pre-determined volume of the final slurry sample is filtered before the addition of sucrose using a 0.45 µm syringe filter. A volume of the filtered sample is then added to a tared 20 mL scintillation vial, dried under vacuum on lyo/oven, and the weight determined gravimetrically. The remaining sample of unfiltered final slurry is frozen with sucrose.

Table A provides the particle size and drug load of the docetaxel nanoparticles produced as described above.

TABLE A

| Polymer | Load DTXL % | Size (nm) |
| --- | --- | --- |
| 16/5 PLA/PEG | 4.05 | 110.70 |
| 30/5 PLA/PEG | 1.48 | 129.00 |
| 50/5 PLA/PEG | 2.75 | 170.60 |
| 80/5 PLA/PEG | 3.83 | 232.00 |

As shown in Table A, docetaxel nanoparticles comprising 50-5 PLA-PEG and 80-5 PLA-PEG result in a drug load of about 2.75% and 3.83%, respectively.

Figure 15:
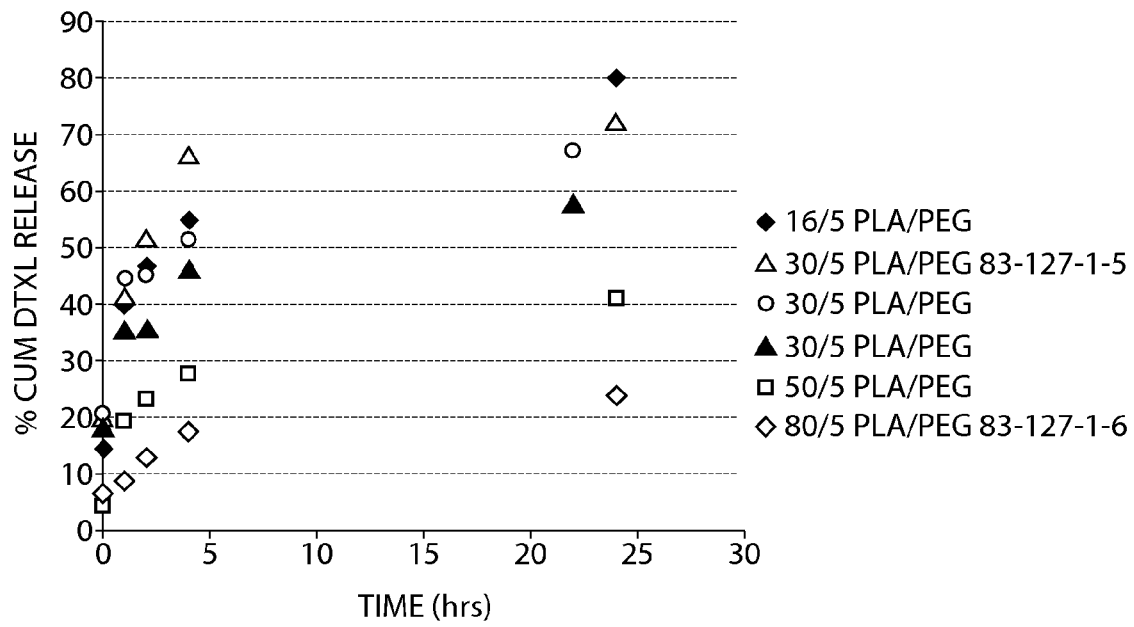
FIG. 15 depicts in vitro release of docetaxel of various nanoparticles disclosed herein.

In vitro release test is performed on the above described docetaxel nanoparticles. As depicted in FIG. 15, nanoparticles fabricated using 50-5 PLA-PEG or 80-5 PLA-PEG slowed down the release of docetaxel from the nanoparticles compared with nanoparticles having lower molecular PLA-PEG.

Example 10

Bortezomib Nanoparticles

Bortezomib nanoparticles comprising various PLA-PEG copolymers are prepared using the following formulation: 30% (w/w) theoretical drug and 70% (w/w) polymer-PEG (16/5, 30-5, 50-5, 65-5, or 80-5 PLA-PEG). % Total solids=20%. Solvents used are 21% benzyl alcohol and 79% ethyl acetate (w/w). For a 1 gram batch size, 300 mg of drug is mixed with 700 mg of polymer-PEG (16/5, 30-5, 50-5, 65-5, or 80-5 PLA-PEG).

Bortezomib nanoparticles are prepared using a protocol similar to the protocol described above for docetaxel nanoparticles.

Table B provides the particle size and drug load of the bortezomib nanoparticles produced as described above.

TABLE B

| Polymer | Load BTZ % | Size (nm) |
| --- | --- | --- |
| 16/5 PLA/PEG | 3 | 107 |
| 30/5 PLA/PEG | 1 | 108 |
| 50/5 PLA/PEG | 2.7 | 106 |
| 65/5 PLA/PEG | 0.2 | 155 |
| 80/5 PLA/PEG | 0.67 | 149 |

Figure 16:
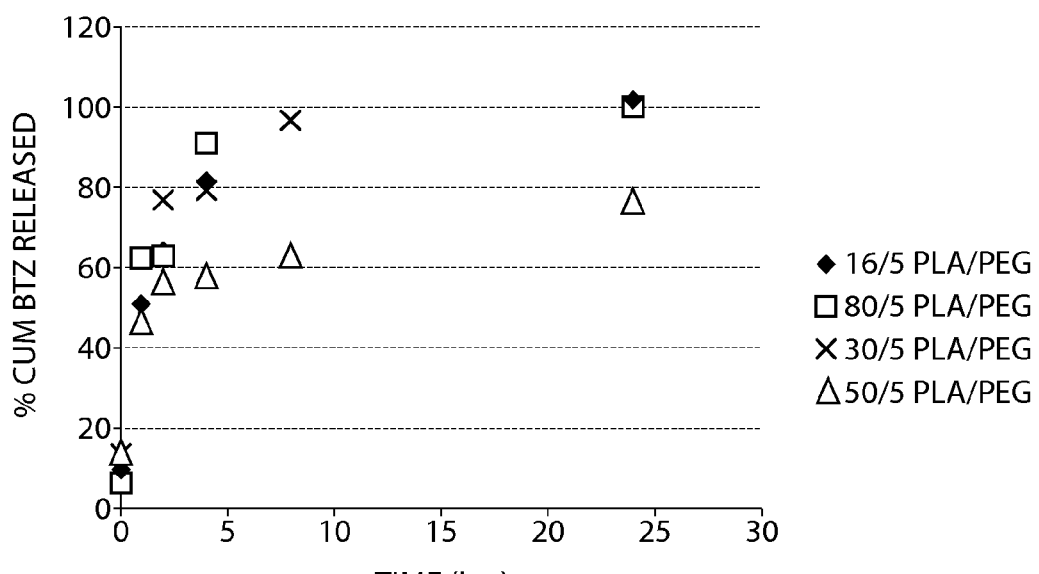
FIG. 16 depicts in vitro release of bortezomib of various nanoparticles disclosed herein.

In vitro release test is performed on the above described bortezomib nanoparticles. As depicted in FIG. 16, incorporation of 50-5 PLA-PEG slowed down the release of bortezomib from the nanoparticles.

Example 11

Vinorelbine Nanoparticles

Vinorelbine nanoparticles comprising either 16-5 or 50-5 PLA-PEG copolymer are prepared using the following formulation: 20% (w/w) theoretical drug and 80% (w/w) polymer-PEG (16/5 or 50-5 PLA-PEG). For nanoparticles comprising 16-5 PLA-PEG: % Total solids=20%; for nanoparticles comprising 50-5 PLA-PEG: % Total solids=30%. For all nanoparticles: solvents used are 21% benzyl alcohol and 79% ethyl acetate (w/w).

Vinorelbine nanoparticles are prepared using a protocol similar to the protocol described above for docetaxel nanoparticles.

Table C provides the particle size and drug load of the vinorelbine nanoparticles produced as described above.

TABLE C

| Polymer | Drug Load % | Size (nm) |
| --- | --- | --- |
| 16/5 PLA/PEG | 10 | 101 |
| 50/5 PLA/PEG | 8.4 | 109 |

Figure 17:
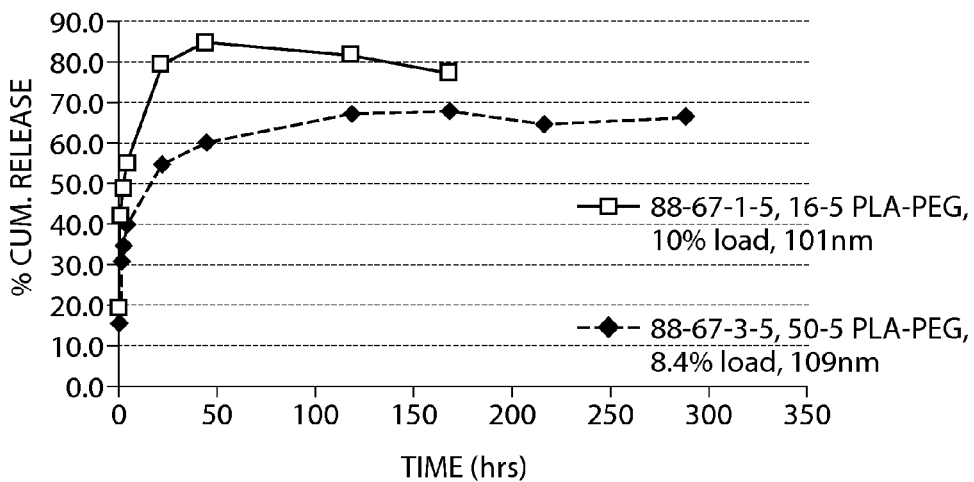
FIG. 17 depicts in vitro release of vinorelbine of various nanoparticles disclosed herein.

In vitro release test is performed on the above described vinorelbine nanoparticles. As depicted in FIG. 17, nanoparticles made using 50-5 PLA-PEG resulted in slower release of vinorelbine from the nanoparticles compared to nanoparticles made with 16-5 PLA-PEG.

Example 12

Vincristine Nanoparticles

Vincristine nanoparticles comprising either 16-5 or 50-5 PLA-PEG copolymer are prepared using the following formulation: 20% (w/w) theoretical drug and 80% (w/w) polymer-PEG (16/5 or 50-5 PLA-PEG). For nanoparticles comprising 16-5 PLA-PEG: % Total solids=40%; for nanoparticles comprising 50-5 PLA-PEG: % Total solids=20%. For all nanoparticles: solvents used are 21% benzyl alcohol and 79% ethyl acetate (w/w).

Vincristine nanoparticles are prepared using a protocol similar to the protocol described above for docetaxel nanoparticles.

Table D provides the particle size and drug load of the vinorelbine nanoparticles produced as described above.

TABLE D

| Polymer | Drug Load % | Size (nm) |
| --- | --- | --- |
| 16/5 PLA/PEG | 2.9 | 103 |
| 50/5 PLA/PEG | 2.8 | 122 |

Figure 18:
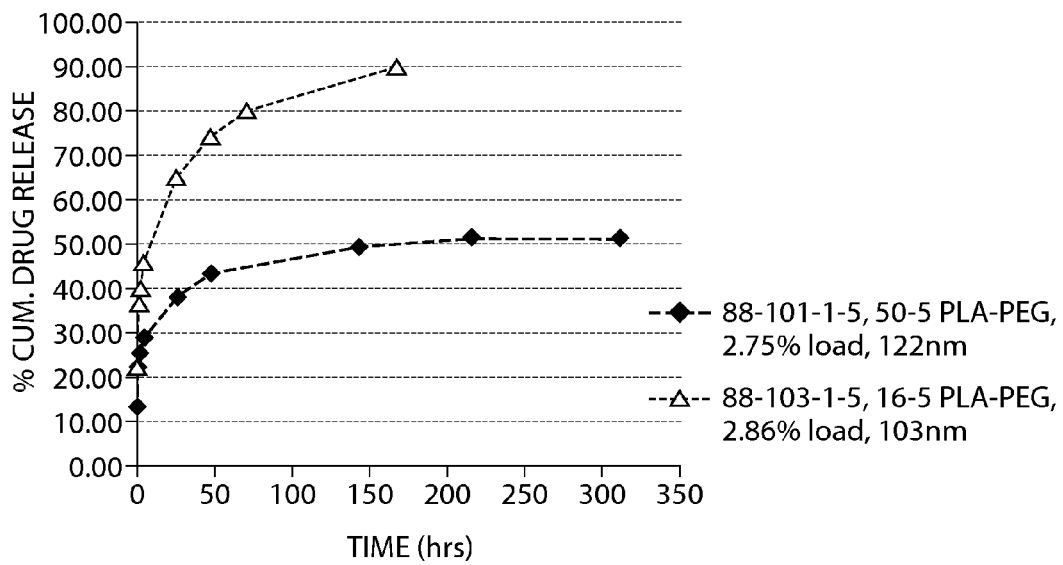
FIG. 18 depicts in vitro release of vincristine of various nanoparticles disclosed herein.

In vitro release test is performed on the above described vincristine nanoparticles. As depicted in FIG. 18, incorporation of 50-5 PLA-PEG slowed down the release of vincristine from the nanoparticles.

Example 13

Bendamustine Nanoparticles

Bendamustine HCl nanoparticles comprising either 16-5 or 50-5 PLA-PEG copolymer are prepared using the following formulation: 17% (w/w) theoretical drug and 83% (w/w) polymer-PEG (16/5 or 50-5 PLA-PEG) at 20% (w/w) polymer concentration in methylene chloride. Bendamustine HCl is complexed with sodium tetraphenylborate at a 1:1 ratio. % Total solids=40%. Solvents used are 32% benzyl alcohol and 68% methylene chloride (w/w).

Bendamustine nanoparticles are prepared using a protocol similar to the protocol described above for docetaxel nanoparticles, with an additional step in which the methylene chloride is removed from the emulsion on a rotovapor by pulling vacuum while the emulsion is rotating in an ice bath for 10 minutes.

Table E provides the particle size and drug load of the vinorelbine nanoparticles produced as described above.

TABLE E

| Polymer | Drug Load % | Size (nm) |
| --- | --- | --- |
| 16/5 PLA/PEG | 3.5 | 97 |
| 50/5 PLA/PEG | 2.1 | 202 |

Figure 19:
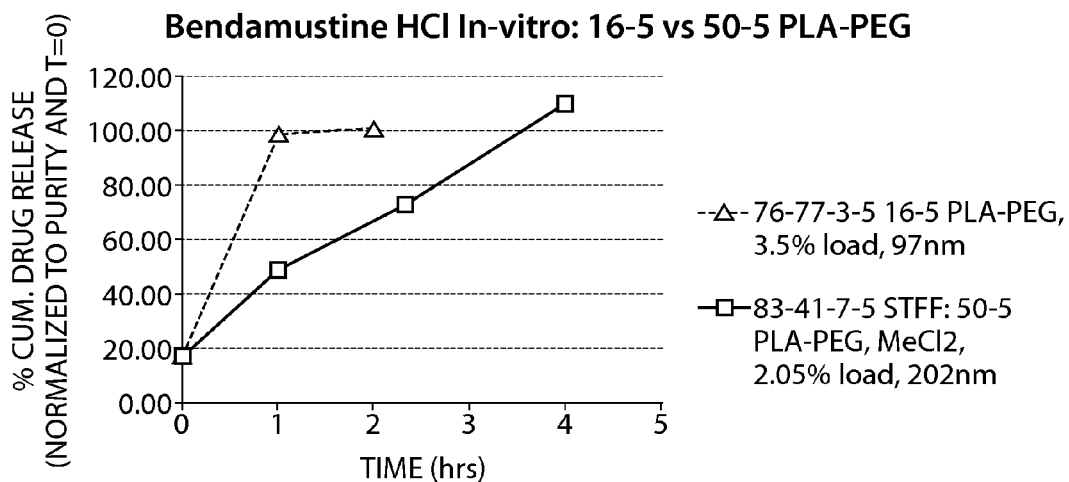
FIG. 19 depicts in vitro release of bendamustine HCl of various nanoparticles disclosed herein.

In vitro release test is performed on the above described bendamustine nanoparticles. As depicted in FIG. 19, nanoparticles made using 50-5 PLA-PEG demonstrated slower release of bendamustine from the nanoparticles compared to nanoparticles made using 16-5 PLA-PEG.

Example 14

Nanoparticle Preparation with Epothilone

Epothilone B nanoparticles were produced using the following formulations:
  10% (w/w) theoretical drug
  90% (w/w) Polymer-PEG, 16-5 PLA-PEG or 50-5 PLA-PEG
  % Total Solids=20%

Solvents: 21% benzyl alcohol, 79% ethyl acetate (w/w)

For a 1 gram batch size, 100 mg of drug was mixed with 900 mg of Polymer-PEG: 16-5 or 50-5 PLA-PEG.

Epothilone B nanoparticles were produced as follows. In order to prepare a drug/polymer solution, 100 mg of epothilone B was added to a 7 mL glass vial along with 3.16 g of ethyl acetate. The mixture was vortexed until the drug was mostly dissolved. Subsequently, 0.840 g of benzyl alcohol was added to the glass vial and vortexed until the drug was completely dissolved. Lastly, 900 mg of polymer-PEG was added to the mixture and vortexed until everything was dissolved.

An aqueous solution for either a 16-5 PLA-PEG formulation or a 50-5 PLA-PEG formulation was prepared. The aqueous solution of the 16-5 PLA-PEG formulation contained 0.1% Sodium Cholate, 2% Benzyl Alcohol, and 4% Ethyl acetate in water. Specifically, 1 g of sodium cholate and 939 g of DI water were added to a 1 L bottle and mixed using a stir plate until they were dissolved. Subsequently, 20 g of benzyl alcohol and 40 g of ethyl acetate were added to the sodium cholate/water mixture and mixed using a stir plate until all were dissolved. The aqueous solution for the 50-5 PLA-PEG formulation contained 5% Sodium Cholate, 2% Benzyl Alcohol, and 4% Ethyl acetate in water. Specifically, 50 g sodium cholate and 890 g of DI water were added to a 1 L bottle and mixed using a stir plate until they were dissolved. Subsequently, 20 g of benzyl alcohol and 40 g of ethyl acetate were added to the sodium cholate/water mixture and mixed using a stir plate until all were dissolved.

An emulsion was formed by combining the organic phase into the aqueous solution at a ratio of 5:1 (aqueous phase:oil phase). The organic phase was poured into the aqueous solution and homogenized using a handheld homogenizer for 10 seconds at room temperature to form a coarse emulsion. The solution was subsequently fed through a high pressure homogenizer (110S). For the 16-5 PLA-PEG formulation, the pressure was set to 9000 psi for two discreet passes to form the nanoemulsion. For the 50-5 PLA-PEG formulation, the pressure was set to 45 psi on gauge (9900 psi) for two discreet passes and then increased to 60 psi on gauge (13200 psi) for two additional passes.

The emulsion was quenched into cold DI water at <5° C. while stirring on a stir plate. The ratio of Quench to Emulsion was 8:1.35% (w/w) Tween 80 in water was then added to the quenched emulsion at a ratio of 25:1 (Tween 80:drug).

The nanoparticles were concentrated through tangential flow filtration (TFF) followed by diafiltration to remove solvents, unencapsulated drug and solubilizer. A quenched emulsion was initially concentrated through TFF using a 300 KDa Pall cassette (Two 0.1 m² membranes) to an approximately 100 mL volume. This was followed by diafiltration using approximately 20 diavolumes (2 L) of cold DI water. The volume was minimized before collection, then 100 mL of cold water was added to the vessel and pumping through the membrane for rinsing. Approximately 100-180 mL of material was collected in a glass vial. The nanoparticles were further concentrated using a smaller TFF to a final volume of approximately 10-20 mL.

In order to determine the solids concentration of unfiltered final slurry, a volume of final slurry was added to a tared 20 mL scintillation vial and dried under vacuum on lyo/oven.

Subsequently the weight of nanoparticles was determined in the volume of the dried down slurry. Concentrated sucrose (0.666 g sucrose/g total) was added to the final slurry sample to attain a final concentration of 10% sucrose.

In order to determine the solids concentration of 0.45 μm filtered final slurry, a portion of the final slurry sample was filtered before the addition of sucrose using a 0.45 μm syringe filter. A volume of the filtered sample was then added to a tared 20 mL scintillation vial and dried under vacuum on lyo/oven. The remaining sample of unfiltered final slurry was frozen after dissolving sucrose (10 wt) in it.

Particle size was analyzed by two techniques—dynamic light scattering (DLS) and laser diffraction. DLS was performed using a Brookhaven ZetaPals instrument at 25° C. in dilute aqueous suspension using a 660 nm laser scattered at 90° and analyzed using the Cumulants and NNLS methods (TP008). Laser diffraction was performed with a Horiba LS950 instrument in dilute aqueous suspension using both a HeNe laser at 633 nm and an LED at 405 nm, scattered at 90° and analyzed using the Mie optical model (TP009).

Table F gives the particle size and drug load of the particles described above.

TABLE F

| Formulation | Description | EpoB Load (%) | Particle Size (nm) |
|---|---|---|---|
| 16/5 PLA/PEG | 20% solids, 2 passes at 9900 psi | 2.3 | 91 |
| 50/5 PLA/PEG | 20% solids, 2 passes at 9900 psi and 2 passes at 13200 psi | 1.6 | 174 |

Example 15

In vitro Release

To determine the in vitro release of epothilone B from the nanoparticles, the nanoparticles were suspended in PBS release media and incubated in a water bath at 37° C. Samples were collected at specific time points. An ultracentrifugation method was used to separate released drug from the nanoparticles.

Figure 20:
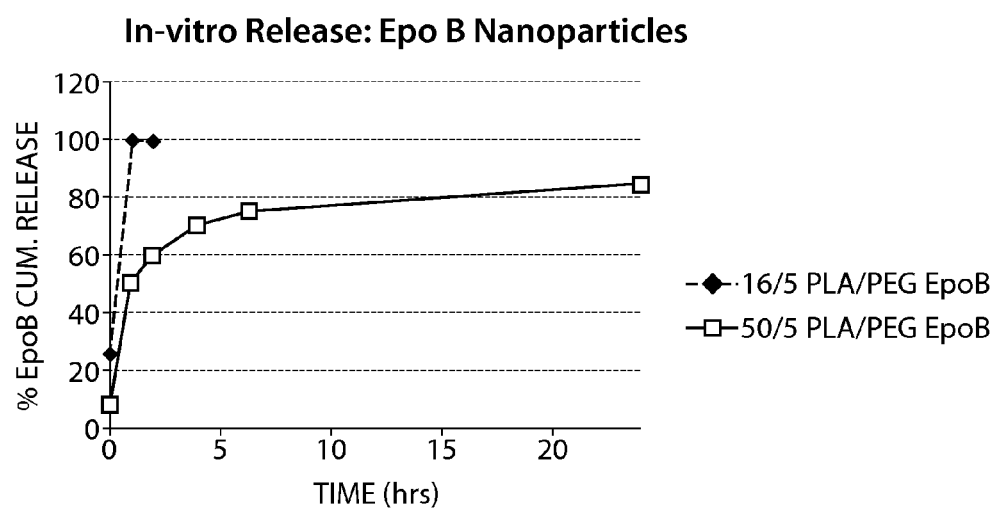
FIG. 20 depicts in-vitro release of epothilone B of various nanoparticles disclosed herein.

FIG. 20 shows the results of an in vitro release study on the 16-5 PLA-PEG and 50/5 PLA/PEG formulations. Data shows 100% release of Epo B from the 16/5 PLA/PEG formulation after one hour. The 50/5 PLA/PEG formulation is a slower releasing formulation with 50% release at 1 hour, 60% release at 2 hours, 70% release at 4 hours, and greater than 80% drug release at 24 hours. The two formulations demonstrate the ability to encapsulate epothilone B into nanoparticles and the ability to impact in vitro release through the selection of the polymer type used in the formulation.

Example 16

Nanoparticle Preparation—Budesonide

All budesonide batches were produced as follows, unless noted otherwise. Drug and polymer (16/5 PLA-PEG) constituents were dissolved in the oil phase organic solvent system, typically 70% ethyl acetate (EA) and 30% benzyl alcohol (BA), at 20% or 30 wt % [solids]. The aqueous phase consisted mainly of water, pre-saturated with 2% benzyl alcohol and 4% ethyl acetate, with sodium cholate (SC) as surfactant. The coarse O/W emulsion was prepared by dumping the oil phase into the aqueous phase under rotor stator homogenization at an oil: aqueous ratio of 1:5 or 1:10. The fine emulsion was then prepared by processing the coarse emulsion through a Microfluidics high pressure homogenizer (generally M110S pneumatic) at 9000 psi through a 100 μm Z-interaction chamber. The emulsion was then quenched into a cold DI water quench at 10:1 or 5:1 quench:emulsion ratio.

Polysorbate 80 (Tween 80) was then added as a process solubilizer to solubilize the unencapsulated drug. The batch was then processed with ultrafiltration followed by diafiltration to remove solvents, unencapsulated drug and solubilizer. This process is depicted pictorially in FIGS. 1 and 2.

The particle size measurements were performed by Brookhaven DLS and/or Horiba laser diffraction. To determine drug load, slurry samples were submitted for HPLC and [solids] analysis. The slurry retains were then diluted with sucrose to 10% before freezing. All ratios listed are on a w/w basis, unless specified otherwise. Tween 80 may be used post quench to remove unencapsulated drug.

An in vitro release method is used to determine the initial burst phase release from nanoparticles at both ambient and 37° C. conditions. Nanoparticles are placed into sink conditions for the API and mixed in a water bath. Released and encapsulated drug are separated by using an ultracentrifuge.

The centrifugal system is run as follows: 3 mL slurry of budesonide nanoparticles (approx 250 μg/mL budesonide PLGA/PLA nanoparticles) in DI-water is placed into glass bottles containing 130 ml release media (2.5% hydroxyl beta cyclodextrin in 1×PBS), which is continually stirred at 150 rpm using a shaker. At pre-determined time points, aliquot of samples (4 mL) were withdrawn. Samples are centrifuged at 236,000 g for 60 minutes and the supernatant is assayed for budesonide content to measured released budesonide.

Particle size is analyzed by two techniques—dynamic light scattering (DLS) and laser diffraction. DLS is performed using a Brookhaven ZetaPals instrument at 25° C. in dilute aqueous suspension using a 660 nm laser scattered at 90° and analyzed using the Cumulants and NNLS methods. Laser diffraction is performed with a Horiba LS950 instrument in dilute aqueous suspension using both a HeNe laser at 633 nm and an LED at 405 nm, scattered at 90° and analyzed using the Mie optical model (TP009).

Example 17

Nanoparticles with various drug loads were prepared by varying the following parameters: vary Q:E ratio (5:1, 15:1 and 30:1); increase [solids] to 30% by reducing initial [budesonide] to 10%; increase particle size by reducing surfactant to 0.5%.

A single emulsion was made at 30% solids, 10% drug, and emulsion was split into three different quenches at Q:E ratios of 5:1, 15:1 and 30:1. The particle size was 137 nm and drug load ranged from 3.4% to 4%. The increased drug load may be due to increased [solids] and particle size, while varying Q:E ratio did not seem to have a significant effect on drug load.

A 10 g batch was made for scale up using the formulation and process of Example 16, using 30% solids and 10% Microfluidics M110EH electric high pressure homogenizer was used to make this batch at 900 psi using a 200 μm Z-chamber. Particle size was 113 nm and drug load was 3.8% (Batch 55-40, control).

Example 18

Nanoparticles

Various batches on nanoparticles were prepared using the general procedure of Example 16, and using the following parameters 16/5 PLA-PEG with mid MW PLA (IV (inherent viscosity)=0.3) at 40% solids:
  Batch #52-198

16/5 PLA-PEG with 40%[solids]; 10% drug, using 60/40 of ethyl acetate/benzyl
  alcohol Batch: #58-27-1

16/5 PLA-PEG with 40% [solids] and 5% [drug]: Batch #58-27-2

16/5 PLA-PEG with high MW PLA (IV=0.6-0.8) at 40% solids: Batch #41-171-A

High MW PLA (IV=0.6-0.8) with DSPE-PEG (2 k): Batch #41-171-B & 61-8-B

16/5 PLA-PEG with high MW PLA (IV=0.6-0.8) at 75% solids: Batch #41-176

16/5 PLA-PEG with doped high MW PLA (IV=0.6-0.8) at 75% and 50% solids: Batch #41-183-A&B Mid MW PLA was obtained from Surmodics (aka Lakeshore (LS)), with an inherent viscosity of 0.3. 16/5 PLA-PEG was obtained from Boehringer Ingelheim (batch 41-176) or Polymer Source (batch 41-183). High MW PLA with a $M_n$ of 80 kDa, $M_w$ of 124 kDa was obtained from Surmodics.

Table G indicates the size and drug load of the nonoparticle batches:

| Batch No# | Description | Size (nm) | Drug Load |
|---|---|---|---|
| 52-198 | Doped mid MW PLA | 120 | 7.08% |
| 58-27-1 | Higher [solids] | 153 | 4.28% |
| 58-27-2 | Higher [solids] and lower initial [drug] | 101 | 1.92% |
| 41-171-A | Doped high MW PLA | 117 | 4.21% |
| 41-171-B | High MW PLA with DSPE-PEG | 224 | 6.11% |
| 41-176 | Doped high MW PLA @ 75% | 181 | 5.14% |
| 41-183-A | Doped high MW PLA @ 75% | 176 | 1.90% |
| 41-183-B | Doped high MW PLA @ 50% | 125 | 1.72% |
| 61-8-B | High MW PLA with DSPE-PEG | 168 | 3.2% |

Figure 21:
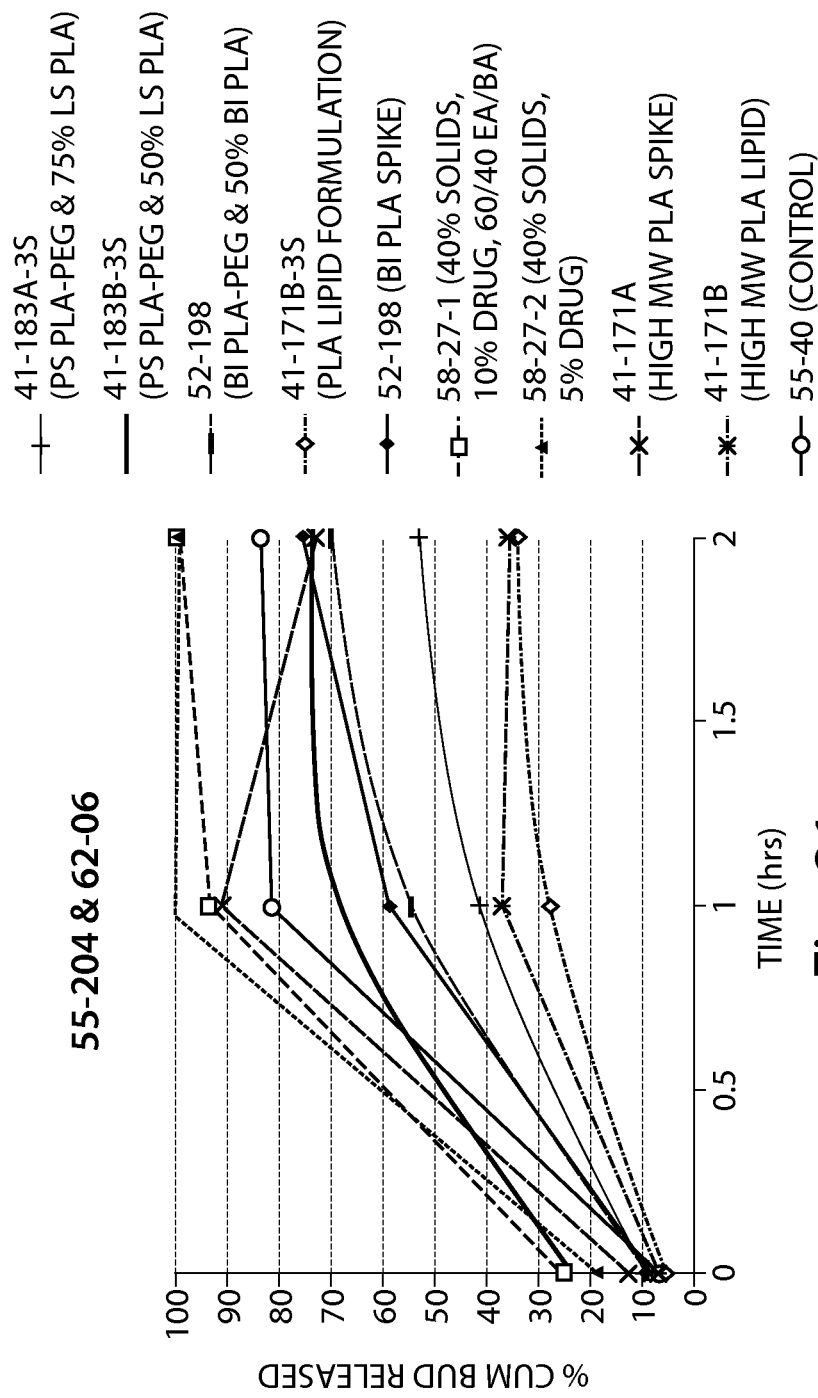
FIG. 21 depicts in-vitro release of budesonide of various nanoparticles disclosed herein.

In vitro release of each batch is depicted in FIG. 21. Note: Batch 41-171-A at 1 hour time point is an outlier caused by one of the uncentrifuged samples reading extraordinarily low. Both batches 41-171-B (lipid formulation) and 41-183-A (high MW PLA) showed drug release≦50% at 2 hours while the other formulations had released between 70-100% within 2 hours.

Example 19

Batch for Animal Study

A 10 g batch was made to confirm the drug load and release seen in batches 41-176 and 41-183-A as well as to provide material for animal studies. Particle size was 183 nm and drug load was 5.03%. Formulation and process parameters were scaled linearly with the exception of water phase [surfactant]. Table H below details the major differences between the batches:

TABLE H

| Parameter or attribute | 41-176 | 41-183A | 62-30 |
|---|---|---|---|
| Scale | 1 g | 1 g | 10 g |
| 16/5 Polymer supply | Boehringer Ingelheim | Polymer Source | Boehringer Ingelheim |
| Sodium cholate | 2% | 5% | 2.5% |
| Homogenizer | M110S | M110S | M110EH |
| Drug load | 5.14% | 1.73% | 5.03% |
| PSD | 181 | 176 | 183 |

Figure 22:
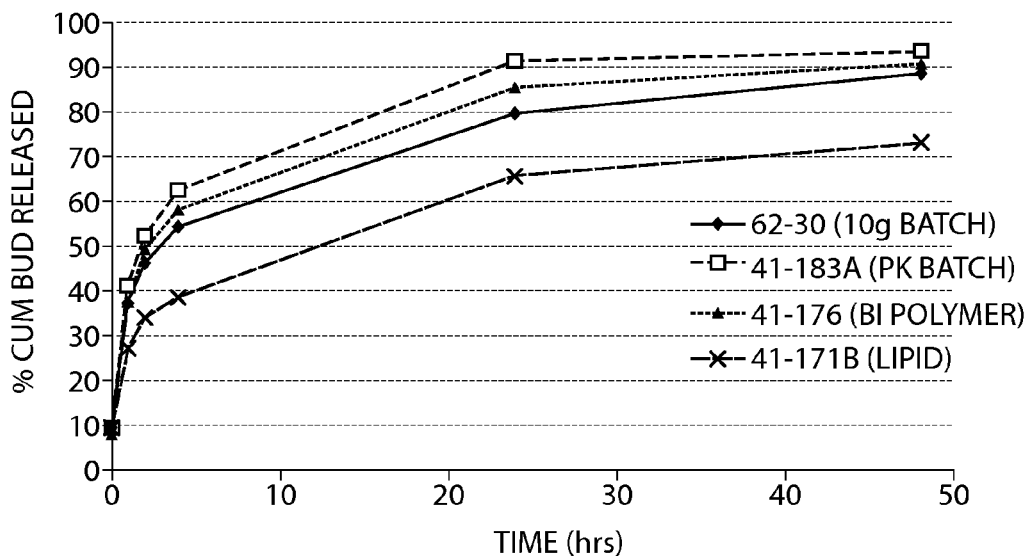
FIG. 22 depicts in-vitro release of budesonide of various nanoparticles disclosed herein.

The 10 g batch, batch no. 62-30, was chosen for the PK study and was first tested for drug release to ensure the release was similar to 41-176 and 41-183-A, as shown in FIG. 22.

Example 20

Rat Study: Pharmacokinetics

Figure 23:
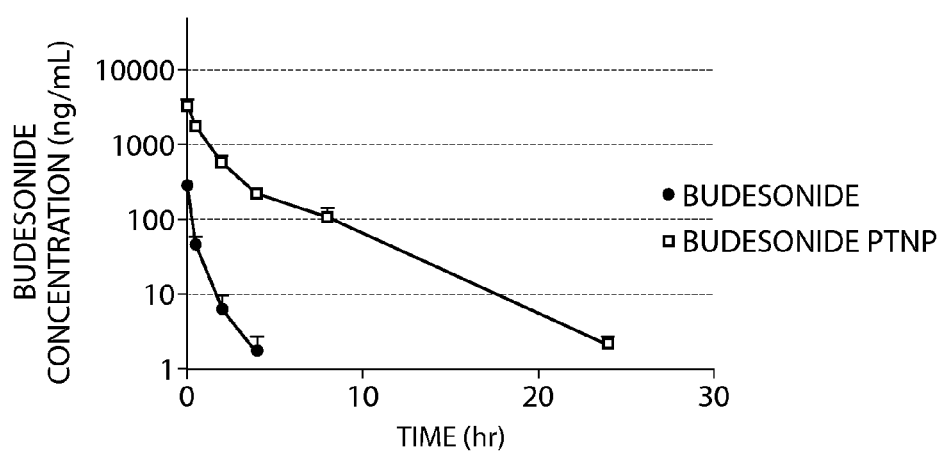
FIG. 23 depicts pharmacokinetics of budesonide and budesonide nanoparticles following a singe intravenous dose (0.5 mg/kg).

Rats (male Sprague Dawley, approximately 300 g with jugular cannulae) were given a single intravenous dose of 0.5 mg/kg of budesonide or passively targeted nanoparticles (PTNP) encapsulating budesonide (prepared as in Example 16) at time=0. At various times after dosing, blood samples were collected from the jugular cannulae into tubes containing lithium heparin, and plasma was prepared. Plasma levels were determined by extraction of the budesonide from plasma followed by LCMS analysis. The results from this PK study are shown in FIG. 23.

Encapsulation of budesonide in co-polymer nanoparticles resulted in an 11-fold increase in the maximum plasma concentration (Cmax), a 4-fold increase in half-life ($t_{1/2}$) and a 36-fold increase in the area under the concentration—time curve (AUC). Budesonide encapsulation also reduces the volume of distribution (Vz) by 9-fold and reduces the clearance from plasma (Cl) by 37-fold. Each of these parameter changes indicates that nanoparticle encapsulation of budesonide promotes plasma localization of budesonide at the expense of tissue distribution of the steroid. Table I outlines the pharmacokinetic analyses of budesonide and budesonide PTNP.

Figure 24:
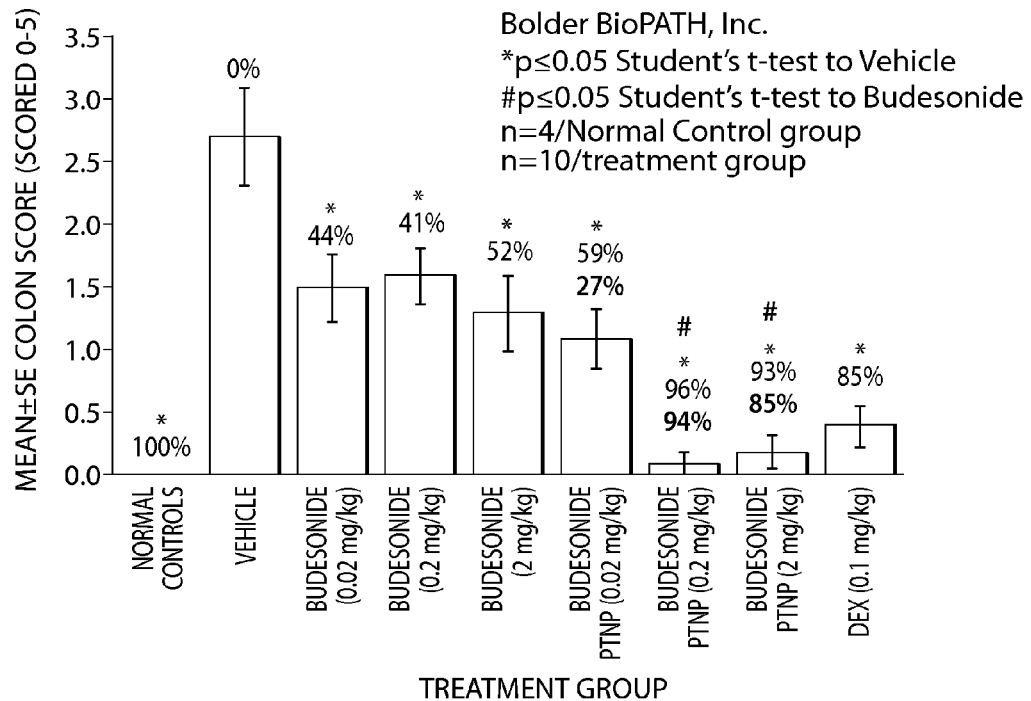
FIG. 24 indicates disease scores in rat intestines in a model of IBD after treatment with budesonide, budesonide PTNP and dexamethasone.
Figure 25:
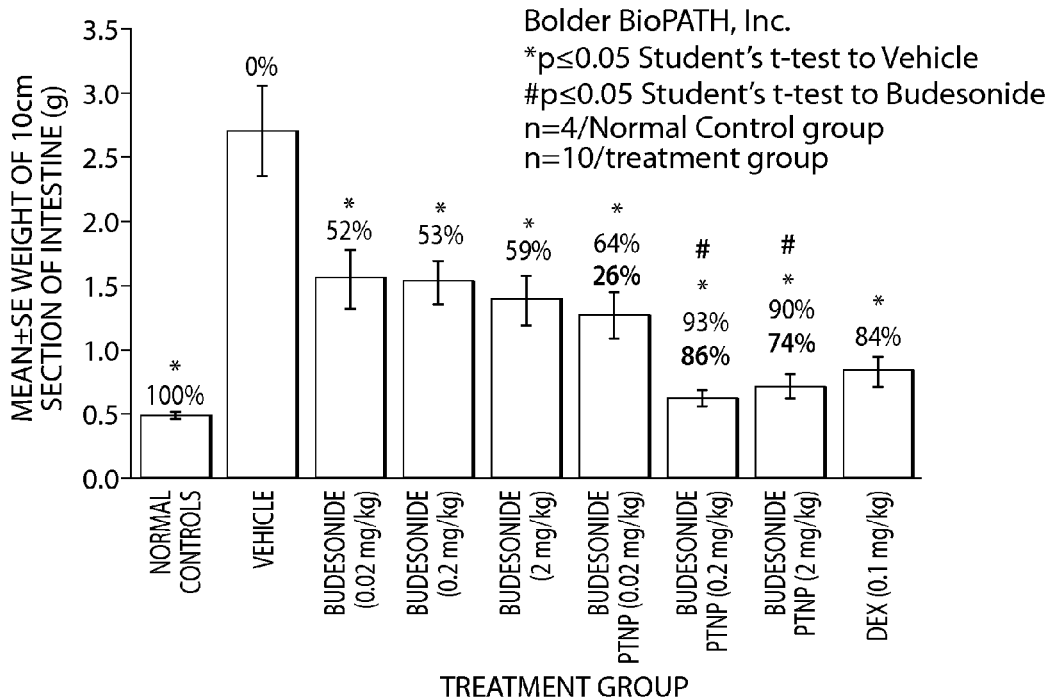
FIG. 25 indicates rat intestinal weights in a Model of IBD after Treatment with budesonide, budesonide PTNP and dexamethasone.

Using a disease scoring system in which a score of 0 is normal, and a score of 5 indicates death due to IBD symptoms, normal rats have an average score of 0, and an average intestinal weight of 0.488 g. In contrast, vehicle treated controls with indomethacin-induced IBD had an average clinical score of 2.7 (FIG. 24) and intestinal weight of 2.702 g (FIG. 25). Intestinal scores were significantly decreased towards normal after treatment with budesonide at doses of 0.02 mg/kg (52% decrease), 0.2 mg/kg (53% decrease) and 2 mg/kg (59% decrease; FIG. 24). In the same way, intestinal scores were significantly decreased towards normal after treatment with budesonide PTNP at doses of 0.02 mg/kg (59% decrease), 0.2 mg/kg (96% decrease) and 2 mg/kg (93% decrease; FIG. 24). Small intestine scores were also significantly decreased by treatment with 0.2 mg/kg budesonide PTNP (94%) or 2 mg/kg budesonide PTNP (85%) compared to animals treated with the same dose of budesonide free-drug (FIG. 25).

Small intestine weights were significantly decreased toward normal following treatment with budesonide at doses of 0.02 mg/kg (52% decrease), 0.2 mg/kg (53% decrease) or 2 mg/kg (59% decrease; FIG. 8). In the same way, intestinal weights were significantly decreased towards normal after treatment with budesonide PTNP at doses of 0.02 mg/kg (64% decrease), 0.2 mg/kg (93% decrease) and 2 mg/kg (90% decrease; FIG. 25). Small intestine weights were also significantly decreased by treatment with 0.2 mg/kg budesonide PTNP (86%) or 2 mg/kg budesonide PTNP (74%) compared to animals treated with the same dose of budesonide free-drug

TABLE I

| Group 1: Budesonide | | | | | | | | |
|---|---|---|---|---|---|---|---|---|
| | Rat 1-1 | Rat 1-2 | Rat 1-3 | Rat 1-4 | Rat 1-5 | Rat 1-6 | Avg | sd |
| Cmax (ng/mL) | 324 | 241 | 226 | 337 | 306 | 279 | 286 | 45 |
| $t_{1/2}$ (hr) | 0.73 | 0.75 | 0.74 | 0.69 | 0.70 | 0.87 | 0.75 | 0.06 |
| $AUC_{inf}$ (hr * ng/mL) | 159 | 126 | 108 | 161 | 159 | 173 | 148 | 25 |
| Vz (mL/kg) | 3311 | 4291 | 4937 | 3104 | 3191 | 3627 | 3744 | 727 |
| Cl (mL/hr/kg) | 3136 | 3966 | 4611 | 3104 | 3151 | 2892 | 3477 | 668 |

| Group 2: Budesonide PTNP | | | | | | | | |
|---|---|---|---|---|---|---|---|---|
| | Rat 2-1 | Rat 2-2 | Rat 2-3 | Rat 2-4 | Rat 2-5 | Rat 2-6 | Avg | sd |
| Cmax (ng/mL) | 3180 | 3750 | 4140 | 3330 | 2800 | 2260 | 3243 | 669 |
| $t_{1/2}$ (hr) | 2.66 | 2.95 | 3.18 | 3.00 | 2.98 | 2.8 | 2.9 | 0.2 |
| $AUC_{inf}$ (hr * ng/mL) | 5614 | 6666 | 5760 | 4686 | 4299 | 5245 | 5378 | 839 |
| Vz (mL/kg) | 341 | 319 | 398 | 463 | 501 | 383 | 400.8 | 70.0 |
| Cl (mL/hr/kg) | 89 | 75 | 87 | 107 | 116 | 95 | 94.8 | 14.7 |

Example 21

Rat Model of Inflammatory Disease

Budesonide and Budesonide PTNP were compared in a model of inflammatory bowel disease (IBD) as an efficacy model of inflammation. In this model, female rats were given two subcutaneous doses of 8 mg/kg indomethacin at 24 hour intervals to induce lesions resembling those occurring in Crohn's disease in the small intestine. Intravenous daily treatment with vehicle, budesonide (0.02, 0.2 or 2 mg/kg) or budesonide PTNP (0.02, 0.2 or 2 mg/kg) or oral daily treatment with Dexamethasone (0.1 mg/kg) was initiated one day before indomethacin treatment (day −1) and continued for 5 total days (days −1 to 3). Animals were euthanized on day 4, and a 10 cm area at risk in the small intestine was scored for gross pathology and weighed.

(FIG. 24). Results of this study indicate that daily intravenous treatment with budesonide or budesonide PTNP significantly inhibited the clinical parameters associated with indomethacin induced inflammatory bowel disease in rats, with budesonide PTNP treatment having a significant beneficial effect over treatment with budesonide at corresponding dose levels.

Example 22

Particles with Alternate Co-polymers

Following the general procedure of Example 16, nanoparticles were formed from budesonide with PLA-PEG co-polymers as follows:

50/5 PLA-PEG: (PLA Mw=50; PEG Mw=5); Batch #55-106-A

50/5 PLA-PEG and high MW (75 Mn PLA: Batch #55-106-B

80/10 PLA-PEG: Batch #55-106-A
80/10 PLA-PEG and high MW PLA: 55-106-B
Batches B and D had high MW 75 Mn PLA doped at 50% of total polymer.

Table J shows drug loading weight percent:

| Batch # | Description | Drug Load |
|---|---|---|
| 55-106-A | 50/5 PLA-PEG | 2.30% |
| 55-106-B | 50/5 PLA-PEG with high MW PLA doped | 3.10% |
| 55-106-C | 80/10 PLA-PEG | 1.40% |
| 55-106-D | 80/10 PLA-PEG with high MW PLA doped | 1.50% |

Figure 26:
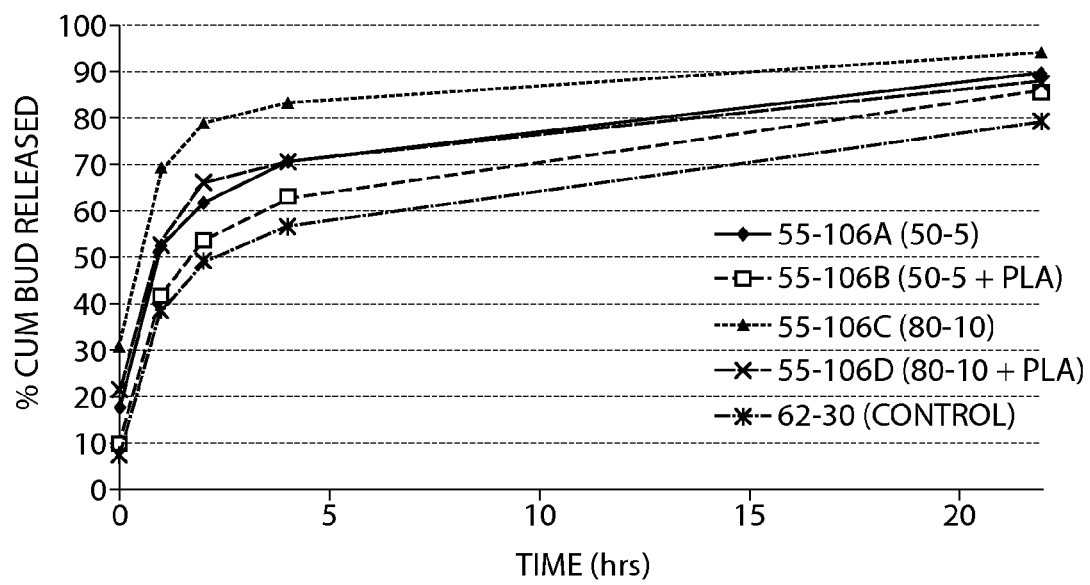
FIG. 26 depicts in vitro release of budesonide in various nanoparticles.

A drug release study was performed to see whether changing copolymer MW had an effect on slowing down drug release. FIG. 26 shows batch #55-106-B, i.e. 50/5 PLA-PEG doped with high MW PLA, appears similar to the control formulation, 62-30.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. A method for identifying therapeutic polymeric nanoparticle compositions with a desired therapeutic agent release rate profile, comprising:
   a) separately preparing a plurality of first aqueous suspensions each comprising polymeric nanoparticles, wherein the nanoparticles comprise i) about 3 to about 40 weight percent of a therapeutic agent, and ii) about 40 to about 90 weight percent of a block copolymer having at least on hydrophobic portion, wherein the block copolymer is poly(D,L-lactic) acid-poly(ethylene)glycol or poly(lactic) acid-co-poly(glycolic) acid-poly(ethylene)glycol; wherein each first aqueous suspension is in a separate compartment;
   b) determining the nanoparticle glass transition temperature of each of the first aqueous suspensions;
   c) varying the amount or molecular weight of the hydrophobic portion of the block copolymer in each of the first aqueous suspensions, if the glass transition temperature of step b) is below 37° C.;
   d) repeating steps b) and c) until a second aqueous suspension with a glass transition temperature of between about 37° C. and about 50° C. and the desired therapeutic agent release rate profile is obtained.

2. The method of claim 1, wherein the method further comprises:
   e) confirming the determined drug release rate from the second aqueous suspension using an in vitro dissolution test.

3. The method of claim 1, wherein the therapeutic agent is a taxane agent.

4. The method of claim 3, wherein the taxane agent is docetaxel.

5. The method of claim 1, wherein the poly(D,L-lactic) acid portion of the block copolymer has a weight average molecular weight of about 16 kDa, and the poly(ethylene) glycol portion of the block copolymer has a weight average molecular weight of about 5 kDa.

6. The method of claim 1, wherein the desired drug release rate of the therapeutic agent from the therapeutic polymeric nanoparticle composition is less than about 50% as determined in an in vitro dissolution test at a 4 hour time point.

7. The method of claim 1, wherein the desired drug release rate of the therapeutic agent from the therapeutic polymeric nanoparticle composition is between about 70 to about 100% as determined in an in vitro dissolution test at a 4 hour time point.

8. The method of claim 1, wherein the glass transition temperature is determined by modulated differential scanning calorimetry.

9. The method of claim 1, wherein the glass transition temperature is determined by differential scanning calorimetry.

10. The method of claim 2, wherein the in vitro dissolution test comprises suspension and centrifuge.

11. The method of claim 1, wherein the therapeutic agent is selected from the group consisting of vinca alkaloids, nitrogen mustard agents, mTOR inhibitors, and boronate esters or peptide boronic acid compounds.

12. A method for screening nanoparticle suspensions to identify a suspension having a specific release rate, comprising:
   a) separately preparing a plurality of suspensions having nanoparticles comprising:
   a therapeutic agent,
   about 40 to about 99 weight percent block copolymer having: at least one hydrophobic portion selected from poly (D,L-lactic) acid or poly(lactic) acid-co-poly(glycolic) acid, and a poly(ethylene)glycol portion, and optionally a homopolymer selected from poly(D,L-lactic) acid or poly(lactic) acid-co-poly(glycolic) acid; wherein each suspension is in a separate compartment, each suspension comprises a pre-determined molecular weight of the block copolymer and if present, a pre-determined molecular weight of the homopolymer;
   b) determining the glass transition temperature of each of the suspensions;
   c) identifying the suspension having a pre-determined glass transition temperature thereby identifying a suspension with the specific release rate, wherein the pre-determined glass transition temperature is between about 37° C. and about 39.5° C.

* * * * *